(12) United States Patent
Russwurm

(10) Patent No.: US 8,765,371 B2
(45) Date of Patent: Jul. 1, 2014

(54) METHOD FOR THE IN VITRO DETECTION AND DIFFERENTIATION OF PATHOPHYSIOLOGICAL CONDITIONS

(75) Inventor: Stefan Russwurm, Jena (DE)

(73) Assignee: Analytik Jena AG, Jena (DE)

(*) Notice: Subject to any disclaimer, the term of this patent is extended or adjusted under 35 U.S.C. 154(b) by 0 days.

(21) Appl. No.: 12/933,169

(22) PCT Filed: Mar. 16, 2009

(86) PCT No.: PCT/EP2009/053042
§ 371 (c)(1),
(2), (4) Date: Dec. 14, 2010

(87) PCT Pub. No.: WO2009/115478
PCT Pub. Date: Sep. 24, 2009

(65) Prior Publication Data
US 2011/0098195 A1      Apr. 28, 2011

(30) Foreign Application Priority Data
Mar. 17, 2008   (DE) .................. 10 2008 000 715

(51) Int. Cl.
C12Q 1/68      (2006.01)
C07H 21/02     (2006.01)

(52) U.S. Cl.
USPC .......................................... 435/6.1; 536/23.1

(58) Field of Classification Search
None
See application file for complete search history.

(56) References Cited

U.S. PATENT DOCUMENTS

| | | |
|---|---|---|
| 2008/0070235 A1 | 3/2008 | Russwurm et al. |
| 2009/0075831 A1 | 3/2009 | Russwurm et al. |
| 2009/0325152 A1 | 12/2009 | Russwurm et al. |
| 2010/0086909 A1 | 4/2010 | Russwurm et al. |
| 2010/0184608 A1 | 7/2010 | Russwurm et al. |
| 2010/0203534 A1 | 8/2010 | Russwurm |

FOREIGN PATENT DOCUMENTS

| | | |
|---|---|---|
| EP | 2107911 | 8/2008 |
| WO | 2005/118878 | 12/2005 |
| WO | 2006/113529 | 10/2006 |

OTHER PUBLICATIONS

Berner et al., Elevated gene expression of interleuken-8 in cord blood is a sensative marker for neonatal infection, Eur J Pediatr (2000) 159: 2-5-210.*

Landre, J., Towards transcription based sepsis diagnosis—recent prognosis. Oct. 24, 2006, SIRS Lab GmbH Workshop, Prague.

SIRS Lab GmbH, Microarray expression profiling: Towards an application in sepsis diagnostics, 6th World Congress on Trauma, Shock, Inflammation and Sepsis? Pathophysiology, Immune Consequences and Therapy, Mar. 4, 2004, XP002327554.

* cited by examiner

Primary Examiner — James Ketter
Assistant Examiner — Reza Ghafoorian
(74) Attorney, Agent, or Firm — Lewis Kohn & Fitzwilliam LLP; David M. Kohn; Kari Moyer-Henry

(57) ABSTRACT

The invention relates to a method for the in vitro detection and/or differentiation and/or progress observation of pathophysiological conditions with the aid of sample nucleic acids, including determination of gene activities by means of a plurality of polynucleotides, determination of gene activities of at least one internal reference gene, and formation of an index value from the single determined normalized gene activities of a multigene biomarker indicating the pathophysiological condition.

3 Claims, 17 Drawing Sheets

(1st cont.)

Legend:

| Gene symbol | Corresponding SeqID | Gene symbol | Corresponding SeqID |
|---|---|---|---|
| MME | 443,444,445,446 | KIAA0146 | 261 |
| CCR2 | 529,530 | TLR5 | 431 |
| CD59 | 571,572,573,574 | CLU | 575,576 |
| NSMAF | 527 | C4orf18 | 611,612 |
| IL7R | 541 | BZRP | 601,602 |
| HLA-DPA1 | 613 | CD82 | 470,471 |
| FGL2 | 615 | IGKC | 401 |
| CPVL | 619,620 | EPC1 | 280 |
| MON2 | 248 | | |

Figure 11
(2nd cont.)

METHOD FOR THE IN VITRO DETECTION AND DIFFERENTIATION OF PATHOPHYSIOLOGICAL CONDITIONS

CROSS REFERENCES

This application is a United States National Stage Application claiming priority under 35 U.S.C. 371 from International Patent Application No. PCT/EP09/53042 filed Mar. 16, 2009, which claims the benefit of priority from German Patent Application Serial No. 102008000715.3 filed Mar. 17, 2008, the entire contents of which are herein incorporated by reference.

The present invention relates to a method for the in vitro detection and/or differentiation and/or progress observation of pathophysiological conditions, the use of a plurality of polynucleotides and/or the gene loci thereof and/or the transcripts thereof for forming at least one multigene biomarker for producing a multiplex assay, the use of at least one polynucleotide and/or the gene loci thereof and/or the transcripts thereof for producing an assay, as well as a kit for carrying out the method.

In particular, the present invention relates to the use of polynucleotides for the detection of gene activities of at least one multigene biomarker, for producing a diagnostic aid for patients with certain pathophysiological conditions such as, e.g., sepsis and sepsis-type conditions, having similar features as an "In Vitro Diagnostic Multivariate Index Assay" (IVDMIA).

Sepsis ("blood poisoning") is a life-threatening infection which affects the entire organism. It is associated with high mortality, occurs increasingly often, and affects persons at any age in life. Sepsis endangers medical progress in many areas of high performance medicine and uses up a major part of resources in health care. Mortality due to severe sepsis did not improve decisively over the past decades. The last two innovation leaps after the introduction of blood culture (about 1880) were the introduction of antibiotics more than 60 years ago and the beginning of intensive care medicine about 50 years ago. In order to achieve similarly decisive treatment progresses at the present day, it is necessary to provide novel diagnostics.

Sepsis is caused by infectious agents. As a specialized therapy against sepsis does not exist as yet, success of the treatment largely depends on successfully fighting the causal infection and on the quality of intensive care medical treatment. What is decisive for survival is the timely administration of an antibiotic which moreover successfully fights the causal pathogens [Kumar et. al., 2006]. Deficits in sepsis diagnostics do, however, delay the therapy begin and the selection of a suitable antibiotic. As the identification of the sepsis pathogen by the current methods of culturing blood is successful only in less than 25% of sepsis cases, with findings being available only after 2-3 days in the case of pathogen identification, the initial selection of an antibiotic or antimycotic (substances directed against fungi) must be made in a "calculated" manner, i.e., by conjecture. In 20-30% of cases this selection is incorrect.

Further causes delaying therapy reside in an erroneous interpretation of disease symptoms and laboratory values. Improved diagnostics simplifying and accelerating sepsis diagnosis can contribute to considerably reduce sepsis mortality and shorten its treatment duration. Specialized medical companies confirm the deficits of previous sepsis diagnostics in polls among Northern American and European intensive care practitioners [Marshall et. al., 2003]. The self-help initiative "Deutsche Sepsis Hilfe e.V." and the Deutsche Sepsis-Gesellschaft deplore the deficits.

In the course of the development of marketable in vitro diagnostics from the field of molecular diagnostics, a draft guideline by the Food and Drug Administration (FDA) of the United States of America was published on Jul. 26, 2007. This guideline provides recommendations, definitions, and hints for the development and approval process. In addition, specifications for the new class of "In-Vitro Diagnostic Multivariant Index Assays (IVDMIA)" are proposed. Characteristics of these assays are:

1) The combination of several single values by means of an interpretation step in order to obtain a single, patient-specific output value in the form of an index, score, or classification. This value may be utilized for diagnostic statements, for damage control, treatment, or prophylaxis against a disease.

2) The achieved result is derived from the measurement values in a way which does not allow any conclusions regarding the measurement data itself. The result can therefore not be confirmed or duplicated by the end user.

3) In conclusion, it is necessary to provide the user with all of the information for an interpretation of the test result.

The present invention concerns in particular genes and/or fragments thereof and their use for preparing multigene biomarkers which are specific for a condition and/or diagnostic problem.

The invention further concerns PCR primers and probes derived from the marker genes for hybridization or reproduction methods.

As before, sepsis is one of the most difficult clinical pictures in modern intensive care medicine, with not only the therapy but also the diagnosis representing a challenge for the clinically working physician. Notwithstanding progresses in pathophysiological understanding and supportive treatment of intensive care patients, generalized inflammatory conditions such as SIRS and sepsis are diseases occurring very frequently in patients in intensive care units and contributing to mortality in a considerable degree [Marshal et al., 2003; Alberti et al., 2003]. Mortality is approx. 20% for SIRS, approx. 40% for sepsis, and rises to as much as 70-80% with the development of multiple organ dysfunctions [Brun-Buisson et al., 1995; Le-Gall et al., 1995; Brun-Buisson et al., 2003]. The contribution of SIRS and sepsis to morbidity and lethality is of interdisciplinary clinical-medical importance, for they increasingly endanger the treatment successes of the most advanced therapy methods in numerous medial fields (e.g., traumatology, neurosurgery, heart/lung surgery, visceral surgery, transplantation medicine, hematology/oncology, etc.) which harbor, without exception, an increased disease risk of SIRS and sepsis. This also finds an expression in the continuous rise in the frequency of sepsis: between 1979 and 1987, a rise by 139% was recorded, i.e., from 73.6 to 176 cases per 100,000 hospital patients [MMWR Morb Mortal Wkly Rep 1990]. A reduction of the morbidity and lethality of a large number of severely afflicted patients is therefore tied in with a concurrent progress in prophylaxis, treatment, and in particular in the recognition and progress observation of sepsis and severe sepsis.

The connotation of the term sepsis has undergone a considerable change over the course of time. An infection or the urgent suspicion of an infection even today form an essential part of current definitions of sepsis. In the framework of inflammatory host reaction, however, particular consideration is given to the description of organ dysfunctions that are remote from the location of an infection. In international literature, the criteria of the consensus conference of the "American College of Chest Physicians/Society of Critical Care Medicine Consensus Conference (ACCP/SCCM)" from the year 1992 have meanwhile found the widest acceptance for a definition of the term sepsis [Bone et al., 1992]. In accordance with these criteria, the clinically defined degrees of severity of "systemic inflammatory response syndrom" (SIRS), "sepsis", "severe sepsis", and "septic shock" are being differentiated. SIRS is here defined as the systemic response of the inflammatory system to a non-infectious stimulus. In this regard, at least two of the following clinical criteria have to be met: fever >38° C. or hypothermia <36° C., leucocytosis >12 g/l or leucopenia <4 g/l, or a shift to the left in the differential hemogram, a heart rate of more than 90/min, tachypnoea >20 breaths/min or $PaCO_2$ (partial pressure of carbon dioxide in arterial blood) <4.3 kPa. This definition offers high sensitivity but low specificity. It is of little help where intensive care medicine is concerned, for as a general rule every intensive care patient meets the SIRS criteria at least for a short period of time.

Sepsis is defined as clinical conditions in which the SIRS criteria are met and an infection is shown to be causal or at least highly likely. An infection is defined as a pathological process brought about by an intrusion of pathogens or of potentially pathogenic organisms into a normally sterile tissue. Unless the body succeeds in confining this infection to the location of origin, the pathogens or their toxins induce an inflammation in organs or body tissues that are remote from the site of infection. Immediate intensive care medical treatment, specific administration of antibiotics, and surgical therapy of the focus of infection are necessary in order to achieve convalescence. A severe sepsis is characterized by the additional occurrence of organ dysfunctions. Frequent organ dysfunctions are changes in the state of awareness, oliguria, lactacidosis, or sepsis-induced hypotension with a systolic blood pressure of less than 90 mmHg or a pressure drop by more than 40 mmHg from the initial value. If such a hypotension can not be alleviated by administration of crystalloids and/or colloids and the patient comes to additionally require catecholamines, this is referred to as septic shock. The latter is ascertained in about 20% of all sepsis patients.

There is agreement among many medical professionals that the consensus criteria according to [Bone et al., 1992] do not correspond to a specific definition of sepsis. Thus, a survey carried out by the European Society of Intensive Care Medicine (ESICM) showed that despite extensive clinical experience, 71% of questioned physicians admitted to a lack of confidence in diagnosing sepsis [Poeze et al., 2003]. The attempt to enforce a unified terminology found varied acceptance in clinical practice. Particularly the advances in understanding the pathophysiology of sepsis caused various experts to search for a corresponding modification of the former definitions. The definitions of sepsis, severe sepsis, and septic shock were confirmed and evaluated as being useful for clinicians and researchers. Nevertheless, the diagnostic criteria of sepsis were expanded considerably in order to do justice to the clinical aspect of warding off infections. The International Sepsis Conference 2001 moreover proposed a novel concept (termed PIRO) for the description of sepsis, which is composed of the criteria of predisposition, infection, immune response (response), and organ dysfunction [Levy et al., 2003]. Despite a new definition of SIRS/sepsis having the acronym PIRO [Opal et al., 2005], the ACCP/SCCM consensus conference from the year 1992 is still being used in most studies [Bone et al., 1992] for a classification of their patients.

Several approaches for diagnosing SIRS and sepsis have been developed. These approaches can be classified into 3 groups.

The first group contains score systems such as, e.g., APACHE, SAPS and SIRS, which can stratify the patients on the basis of a multiplicity of physiological indices. While a diagnostic potential for the APACHE II score could be demonstrated in several studies, other studies have shown that APACHE II and SAPS II are not capable of differentiating between sepsis and SIRS [Carrigan et al., 2004].

The second group contains protein markers which are detected from plasma and serum. These are, for example, CA125, S100B, copeptin, glycine-N-acyl transferase (GNAT), protachykinin and/or fragments thereof, aldose 1-epimerase (mutarotase), Chp, carbamoyl phosphate synthetase 1, LASP-1 (Brahms Diagnostika GmbH Deutschland), IL-1 Ra, MCP-1, MPIF-1, TNF-R1, MIG, BLC, HVEM, IL-15, MCP-2, M-CSF, MIP-3b, MMP-9, PARC, ST-2; IL-6, sIL-2R, CD141, MMP-9, EGF, ENA-78, EOT, Gra-beta, IL-1b, leptin, MIF, MIP-1a, OSM, protein C, P-selectin, and HCC4 (Molecular Staging, Inc., USA) or CD 14 antigen, lipopolysaccharide-binding sites on the proteins alkaline phosphatase and inter-alpha-trypsin inhibitor (Mochida Pharm Co, Ltd. Japan). Notwithstanding the great number of patented biomarkers, only few could find acceptance in everyday clinical work. Among these, procalcitonin (PCT, BRAHMS) and the C-reactive protein (CRP, Eli Lilly) appear to be the markers best suited for differentiating between infectious and non-infectious causes of SIRS.

Procalcitonin is a peptide having a length of 116 aminoacids which plays a role in inflammation reactions. Over time, this marker has increasingly been used as a new infection marker in intensive care units [Sponholz et al., 2006]. This marker is considered to be an infection marker and serves for determining the degree of severity of sepsis, with the dynamics of values being more important than the absolute values, for instance in order to differentiate between infectious and non-infectious complication in heart surgery patients [Sponholz et al., 2006]. Despite the far-reaching acceptance of the biomarker PCT, it could be demonstrated in international studies that the achieved sensitivities and specificities of the sepsis marker PCT are still insufficient, particularly for differentiating a systemic bacterial SIRS, i.e. sepsis, from non-bacterial SIRS [Ruokonen et al., 1999; Suprin et al. 2000; Ruokonen et al., 2002; Tang et al., 2007a]. The meta-analysis by Tang and colleagues [Tang et al., 2007a] relating to 18 studies shows that PCT is only poorly suited for discriminating between SIRS and sepsis. In addition, the authors stress that PCT has a very low diagnostic accuracy at an odd ratio (OR) of 7.79. The authors state as a rule that an OR <25 is not meaningful, is helpful between 25 and 100, and is highly accurate in cases of more than 100 [Tang et al., 2007a].

C-reactive protein (CRP) is a protein having a length of 224 amino acids which plays a role in inflammatory reactions. The measurement of CRP is to serve for observing the progress of the disease as well as the effectivity of the selected therapy.

It was described in several reports that PCT is suited better as a diagnostic marker than CRP in the field of intensive care medicine [Sponholz et al., 2006; Kofoed et al., 2007]. In addition, PCT is considered to be suited better than CRP for differentiating non-infectious versus infectious SIRS as well as bacterial versus viral infection [Simon et al., 2004].

The third group contains biomarkers or profiles that were identified on the transcriptome level. These molecular parameters are said to enable better correlation of the molecular inflammatory/immunological host response with the degree of severity of the sepsis, but also statements concerning the individual prognosis. Various scientific groups and commercial organizations are currently taking pains to search for such biomarkers such as, for example, changes in the cytokine concentrations in blood caused by bacteria cell wall constituents such as lipopolysaccharides [Mathiak et al., 2003], or the use of gene expression profiles in a blood sample for identifying differences in surviving and non-surviving sepsis patients [Pachot et al., 2006]. Gene expression profiles or classifiers are suited for determining the degree of severity of sepsis [WO 2004/087949], differentiating between local or systemic infection [non-published DE 10 2007 036 678.9], identification of the source of infection [WO 2007/124820] or of gene expression signatures for a differentiation between several etiologies and pathogen-associated signatures [Ramilo et al., 2007]. Owing to the insufficient specificity and sensitivity of the consensus criteria according to [Bone et al., 1992], of the currently available protein markers, and the time required for detecting the cause of infection by culturing blood there is, however, an urgent demand for new methods doing justice to the complexity of the disorder. Many gene expression studies using either single genes and/or combinations of genes named as classifiers, as well as numerous descriptions of statistical methods for deriving a score and/or index [WO03084388; U.S. Pat. No. 6,960,439] can be found in the prior art.

There is nowadays agreement to the effect that a meaningful description of complex diseases is possible through a plurality of parameters only.

Molecular signatures are increasingly being introduced into clinical diagnostics, in particular in cases of complex disorders that can not be detected with the aid of conventional biomarkers, but also for the evaluation of risks to the patients and for the identification of responders in the use of drugs and therapies. The following enumeration is intended to accentuate the current status and the fields of application of gene expression diagnostics.

1) The microarray-based signature including 70 genes by the name of MammaPrint (Agendia, NL) allows to give a prognosis concerning the risk of recurrence and developing metastases in women afflicted with breast cancer. This is an investigation whether the risk of developing remote metastases in the following years may be classified as high or low, and whether chemotherapy would be beneficial. The approval of these tests by the FDA resulted in the development of guidelines for a new class of diagnostic tests, the so-called IVDMIA (In Vitro Diagnostic Multivariate Index Assay Index Assay). The MammaPrint signature is measured and calculated on a microarray at the manufacturer's laboratories.

2) Formaldehyde-fixated tissue samples are used to assess, by means of the Oncotype DX-Multigen Assay (Genomic Health, USA), the probability of the recurrence of breast cancer in female patients, and to examine the response of the female patients to chemotherapy. 21 genes are combined into a "recurrence score." The measurement takes place at the facilities of the company, with TaqMan-PCR technology also being employed.

3) The AlloMap gene expression test by the company XDx (USA) is utilized for monitoring possible rejection reactions in heart transplantation patients, which occur in approx. 30% of the patients within one year. Several biopsies had hitherto been necessary for a diagnosis. The test is based on 11 quantitative PCR assays (additionally 9 controls and references) by making use of the TaqMan technology (Hoffman-La Roche) at the manufacturer's facilities. The sample material is blood. As early as two months following transplantation, the measurement results are reliable and predict the absence of rejection reactions for the next 80 days.

One point common to these tests is that the addressed diagnostic problem allows examination periods of several days before the result is available. In diagnostic tests for the indication of sepsis, on the other hand, the information must be available within a single workday.

Several uses of gene expression profiles are known in the prior art.

Pachot and colleagues demonstrate the usefulness of expression signatures for evaluating the progress of patients with septic shock. Here, molecular differences are found which reflect the restoration of a functional immune system in the survivors. Within the first day following the diagnosis of septic shock, 28 marker genes having functions in the innate immune system indicate with high sensitivity (100%) and specificity (88%) whether the immune paralysis is reversible and thus allows the patient's survival. In the study the group of patients was, however, too small (38) for drawing up a robust profile, and a validation of this set of data by an independent set of data has not been carried out so far. The prior art contains numerous studies for the identification of gene expression markers [Tang et al., 2007b] or gene expression profiles for ascertaining a systemic infection [Johnson et al., 2007].

Tang and colleagues [Tang et al., 2007b] searched within a specific blood cell population—the neutrophils—for a signature enabling a differentiation of SIRS and sepsis patients. 50 markers from this cell population are sufficient to represent the immune response to a systemic infection and to enable new insights concerning pathophysiology and the signal paths involved.

The classification of patients with and without sepsis succeeds with high certainty (PPV 88% and 91%, respectively, in training and test data set). Applicability for clinical diagnosis is, however, limited through the fact that in blood, this signature may be superposed by signals from other blood cell types. As regards applicability, the preparation of this blood cell population is accompanied by increased complexity. Nevertheless, the significance for practical applications of the results made public in this study is limited because the selection of patients was highly heterogeneous. The study had included patients exhibiting highly different accompanying illnesses such as, e.g., 11% to 16% tumor disorders, or had been subjected to highly different therapeutic measures (e.g., 27% to 64% vasopressor therapy), which had a strong influence on the gene expression profiles.

Johnson and colleagues [Johnson et al., 2007] describe on a group of trauma patients that the characteristics of a sepsis may be measured as early as 48 hours prior to a clinical diagnosis by way of molecular changes. The trauma patients were examined over several days. Some of the patients developed sepsis. Non-infectious SIRS patients were compared to pre-septic patients. The identified signature from 459 transcripts is composed of markers for the immune response and inflammation markers. The sample material was full blood, with analyses being carried out on a microarray. It is not clear whether or not this signature may also be extended to other groups of septic or pre-septic patients. A classification and the diagnostic usefulness of this signature were not described.

In the prior art there are furthermore descriptions of other signatures, for instance the host's response to an infection.

The specificity of the host response to different pathogens has previously been examined in several experimental systems. None of the studies did, however, contain gene expression profiles and/or signatures of sepsis patients.

The aim of Feezor and colleagues [Feezor et al., 2003] was to identify differences between infections with gram-negative and gram-positive pathogens. Blood samples of three different donors were stimulated ex vivo with *E. coli*-LPS and thermally inactivated *S. aureus*. Gene expression studies were carried out by means of microarray technology. The study group found both genes that were up-regulated following *S. aureus* stimulation and down-regulated following LPS stimulation, and genes that were more highly expressed after LPS treatment than after the addition of thermally inactivated *S. aureus* germs. At the same time, many genes were up-regulated in a same degree by gram-positive and gram-negative stimulation. This is true, e.g., for the cytokines TNF-α, IL-1β and IL-6. Unfortunately, the differentially expressed genes were not identified by name in the publication, thus enabling only an indirect comparison with other results. Besides gene expression, Feezor et al. also examined the plasma concentrations of several cytokines. In this case the gene expression data did not necessarily correlate with the plasma concentrations. In gene expression, the quantity of mRNA is measured which is, however, subject to post-transcriptional regulation in protein synthesis, which may account for the observed differences.

The most interesting publication in connection with this topic was published by a Texan research group headed by Ramilo [Ramilo et al., 2007]. Here, too, gene expression studies were carried out on human blood cells, which uncovered differences in the molecular host reaction to various pathogens. To this end, pediatric patients with acute infections such as, e.g., acute respiratory tract disorders, urinary tract disorders, bacteriaemias, local abscesses, bone and joint infections, as well as meningitis were examined. Microarray experiments were carried out with RNA samples which had been isolated from peripheral mononuclear blood cells from ten patients each with *E. coli* and *S. aureus* infection. The identification of the pathogen took place with the aid of blood culture. Throughout this training data set, 30 genes were identified, the use of which allowed to diagnose the causal pathogenic germs with high accuracy.

Despite the numerous published studies and the individual signatures described in them on which the prior art is founded, none of them allow a diagnostic statement as to sepsis and/or sepsis-type conditions. None of these publications offers the reliability, accuracy, and robustness of the presently disclosed invention. These studies have the focus of identifying the "best" multigene biomarker (classifier) under a scientific viewpoint, however not—as in the present invention—the optimum multigene biomarker for a specific clinical problem [Simon at al., 2005].

It is thus an object of the present invention to provide a test system allowing a quick and reliable statement concerning a pathophysiological condition, e.g., sepsis.

In terms of method, this object is achieved through the features of claim 1.

With regard to use, the object is achieved through the features of claims 4 and 11.

A kit according to claim 14 equally achieves the object.

In a general form, the present invention relates to a system including the following elements:
set of gene activity markers
reference genes as an internal control for the normalization of the gene activity marker signals in full blood
detection mainly by way of real-time PCR or other amplification methods or hybridization methods
use of an algorithm for transforming the individual results of the gene activity markers into a common numerical value, index, or also score
representation of this numerical value on a correspondingly graded scale
calibration, i.e., grading of the scale in accordance with the intended application through earlier validation experiments.

The system provides a solution to the problem of determining disease conditions such as, e.g., the differentiation of infectious and non-infectious multiple organ failure, but also for other applications and problems relevant in this context.

In particular, the present invention relates to a method for the in vitro detection and/or differentiation and/or progress observation of pathophysiological conditions selected from the group consisting of: SIRS, sepsis, and their degrees of severity; sepsis-type conditions; septic shock; infectious/non-infectious multiple organ failure; survival probability in sepsis; focus of an infection; responders/non-responders to a particular therapy; causes of a pathophysiological condition, in particular classification of an infection by gram-positive and/or gram-negative bacteria; the method including the following steps:
a) isolating sample nucleic acids from a sample originating from a patient;
b) determining gene activities by means of a plurality of polynucleotides selected from the group consisting of SEQ ID NO: 1 to SEQ ID NO: 669 and/or their gene loci and/or their transcripts and/or fragments thereof for forming at least one multigene biomarker that is characteristic for the detection and/or differentiation and/or the progress of a patient's pathophysiological conditions;
c) determining gene activities of at least one internal reference gene to which the gene activities determined under b) are related, in particular normalized;
d) forming an index value indicating the pathophysiological condition from the single determined normalized gene activities of the multigene biomarker.

In a preferred method, the at least one reference gene is a housekeeping gene, wherein the housekeeping gene is selected in particular from polynucleotides of the group consisting of SEQ ID NO: 676 to SEQ ID NO: 686 and/or their gene loci and/or their transcripts and/or fragments thereof.

In a preferred manner, gene loci, sense and/or antisense strands of pre-mRNA and/or mRNA, small RNA, in particular scRNA, snoRNA, micro RNA, siRNA, dsRNA, ncRNA or transposable elements are used as polynucleotide sequences.

The index is preferably determined by means of statistical methods such as monitored classification methods from the field of automated and static learning such as, e.g., (diagonal, linear, quadratic) discriminant analysis, super vector machines, generalized partial least squares, k next neighbors, random forests, k-next neighbor. For a linear discriminant analysis it is possible to use, for example, the following formula:

$$f_{LD}(x_1, \ldots, x_p) = \sum_{i=1}^{p} w_i x_i - w_0$$

The invention further relates to the use of a plurality of polynucleotides selected from the group consisting of SEQ ID NO: 1 to SEQ ID NO: 669 and/or their gene loci and/or their transcripts and/or fragments thereof for forming at least one multigene biomarker for producing a multiplex assay as an aid for an evaluation whether a pathophysiological condition is present in a patient, and/or for determining the degree of severity and/or the progress of the pathophysiological condition.

In a preferred manner, the multigene biomarker is a combination of several polynucleotide sequences, in particular gene sequences, the gene activities of which are used to perform a classification and/or form an index or score with the aid of an interpretation function.

For the purposes of the present invention it was found to be advantageous if the gene activities are detected by means of enzymatic methods, in particular amplification methods, preferably polymerase chain reaction (PCR), preferably real-time PCR; and/or by means of hybridization methods, in particular those on microarrays.

Differential expression signals of the polynucleotide sequences contained in the multigene biomarker, which occur during detection of the gene activities, may advantageously and unambiguously be associated to a pathophysiological condition, a progress, and/or therapy monitoring.

From the single determined gene activities an index is typically formed which, following corresponding calibration, is a measure for the degree of severity and/or the progress of the pathophysiological condition, in particular of the sepsis or sepsis-type condition.

This index or score may be indicated on a scale allowing easy interpretation so as to provide a fast diagnostic aid to the treating physician.

In an advantageous embodiment of the invention, the obtained gene activity data is employed for producing software for the description of at least one pathophysiological condition and/or a diagnostic problem and/or as an aid for diagnostic purposes and/or for patient data management systems.

In order to produce the gene activity data, specific gene loci, sense and/or antisense strands of pre-mRNA and/or mRNA, small RNA, in particular scRNA, snoRNA, micro RNA, siRNA, dsRNA, ncRNA or transposable elements, genes and/or gene fragments are advantageously used which exhibit a sequence homology of at least approx. 10%, in particular approx. 20%, preferably approx. 50%, in a particularly preferred manner approx. 80%, with the polynucleotide sequences according to SEQ ID NO: 1 to SEQ ID NO: 669.

The invention further relates to the use of at least one polynucleotide selected from the group consisting of SEQ ID NO: 1 to SEQ ID NO: 152 and/or their gene loci and/or their transcripts and/or fragments thereof for producing an assay for an evaluation whether a pathophysiological condition is present in a patient, and/or for determining the degree of severity and/or the progress of the pathophysiological condition.

The pathophysiological condition is advantageously selected from the group consisting of: SIRS, sepsis, and their degrees of severity; sepsis-type conditions; septic shock; infectious/non-infectious multiple organ failure; local/systemic infection; improvement/worsening of a pathophysiological condition, in particular sepsis; responders/non-responders to a particular therapy; focus of an infection; causes of a pathophysiological condition, in particular classification by gram-positive and/or gram-negative.

In accordance with the invention it is preferred if the sample nucleic acid is RNA, in particular total RNA or mRNA, or DNA, in particular cDNA.

The invention further relates to a kit for carrying out the method of the invention, containing at least one multigene biomarker including a plurality of polynucleotide sequences which are selected from the pool of SEQ ID NO: 1 to SEQ ID NO: 669 and/or their gene loci and/or their transcripts and/or fragments thereof, and/or primers and/or probes and/or antisense nucleotides herefor, the multigene biomarker being specific for a patient's pathophysiological condition of a and encompassing conditions which are selected from the group consisting of: SIRS, sepsis, and their degrees of severity; sepsis-type conditions; septic shock; infectious/non-infectious multiple organ failure; survival probability in sepsis; local/systemic infection; responders/non-responders to a particular therapy; focus of an infection; causes of a pathophysiological condition, in particular classification of an infection by gram-positive or gram-negative pathogens.

The polynucleotide sequences of the kit preferably also include gene loci, sense and/or antisense strands of pre-mRNA and/or mRNA, small RNA, in particular scRNA, snoRNA, micro RNA, siRNA, dsRNA, ncRNA, or transposable elements.

The polynucleotide sequences having the SEQ IDs indicated in Tables 11 and 16 are preferably utilized as multigene biomarkers for the differentiation of SIRS/sepsis or of infectious/non-infectious multiple organ failure. The polynucleotide sequences having the SEQ IDs indicated in Tables 20 and 21 are preferably utilized as multigene biomarkers for the differentiation of causes of a pathophysiological condition, in particular classification by gram-positive and/or gram-negative bacteria.

As part of an integrated system (In Vitro Diagnostic Multivariate Index Assay, IVDMIA), the present invention allows to assess a potential infectious complication in patients with SIRS or possible sepsis. This system includes the selection of the patients and the determination of their gene expression signals in an interpretable index which may be used by the physician as a diagnostic aid.

This system combines the measured gene expression data of defined sequence groups selected from SEQ ID NO: 1 to SEQ ID NO: 669 and/or their gene loci and/or their transcripts and/or fragments thereof, as well as of housekeeping genes. In a preferred embodiment of the present invention, specific genes and/or gene fragments which exhibit a sequence homology of at least approx. 10%, in particular approx. 20%, preferably approx. 50%, in a particularly preferred manner approx. 80% with the polynucleotide sequences according to SEQ ID NO: 1 to SEQ ID NO: 669 or with the housekeeping genes are used for producing the gene activity data.

Table 32 shows the highly relevant sequence pool which is important for various clinical problems.

Tables 8, 11, and 16 show a preferred selection of sequences which, when integrated into the above-mentioned system, are essential for the differentiation between SIRS and sepsis.

The selection of the sequences from the highly relevant sequence pool depends on the clinical problem.

The applicant developed a method which utilizes large sequence pools in order to determine and/or differentiate conditions or provide answers to defined diagnostic problems. Examples may be found in the following patent specifications: Unterscheidung zwischen SIRS, Sepsis und sepsis-ähnlichen Zuständen (Differentiation between SIRS, sepsis, and sepsis-type conditions) [WO 2004/087949; WO 2005/083115], Erstellung von Kriterien zur Vorhersage des Krankheitsverlaufs bei Sepsis (Drawing up criteria for the prediction of the progress of the disease in sepsis [WO 05/106020], Unterscheidung zwischen infektiösen/nichtinfektiösen Ursachen eines Multiarganversagens (Differentiation between non-infectious and infectious causes of a multiple organ failure) [WO 2006/042581], in vitro Klassifizierung von Genexpressionsprofilen von Patienten mit infektiösen/nichtinfektiösem Multiorganversagen (In vitro classification of gene expression profiles of patients with infectious/non-infectious multiple organ failure) [WO 2006/100203], Feststellung der lokalen Ursachen eines Fiebers unklarer Genese (Determination of the local causes of a fever of unclear origin) [WO 2007/144105], Polynukleotide zur Erfassung von Genaktivitäten für die Unterscheidung zwischen lokaler und systemischer Infektion (Polynucleotides for the detection of gene activities for the differentiation between local and systemic infection) [DE 10 2007 036 678.9].

The invention relates to polynucleotide sequences, a method, and moreover kits for preparing multigene biomarkers exhibiting features of an "In Vitro Diagnostic Multivariate Index Assay" (IVDMIA) in one and/or several modules.

Definitions:

For the purposes of the present invention the following definitions are being used:

Condition: The clinically defined degrees of severity "systemic inflammatory response syndrom" (SIRS), "sepsis", "severe sepsis", and "septic shock", as defined in [Bone et al., 1992] and the PIRO concept [Levy at al., 2003].

Multiple organ failure: What is referred to as multiple organ failure is a failure of two or more vital organ systems taking place concurrently or in rapid temporal succession. The multiple organ dysfunction syndrome (MODS) precedes the MOF (multiple organ failure) as an initial organ insufficiency [Zeni et al., 1997]. The term multiple organ failure is nowadays used if two or more organs simultaneously or successively exhibit dysfunctions while a chronically persisting organ failure may be excluded. Prognosis of the MOF is closely related with the number of organ systems involved. Mortality in the case of failure of an organ is 22% within the first 24 hours and 41% after 7 days. In cases of three organ systems failing, mortality rises to 80% on the first day and to 100% after 4 days [Knaus et al., 1985].

One important pathomechanism for the genesis of MODS and MOF is the development of a systemic inflammation syndrome (SIRS, [Bone et al., 1992]. The origins of MODS and MOF may be of both the infectiological and the non-infectiological type.

Fever of unknown origin: Fever of unknown origin (FUO) is clinically defined as a fever where the temperature is higher than 38.8° C. over a period of more than 3 weeks, without a clear diagnosis of the cause being available after a one-week examination period. Four classes of FUO were described as a function of origin: FUO of classical, nosocomial, immune-deficient or HIV-related origin [Roth and Basello, 2003]. FUO was also reported as "a rather known disease of unusual phenotype as a rare disorder" [Amin and Kauffman, 2003].

An infection is documented in only 10% of patients with post-operative fever [Pile et al., 2006]. In most cases the patient's temperature returns to normal within four days after the surgery. Nevertheless some patients develop an infection on or after the fifth post-operative day, which is pneumonia in 12% of cases. Likewise, Pile and colleagues report that there is a high probability of a fever occurring two days after surgery to be an infection such as, e.g., an infection of the urinary tract and/or of the internal abdomen (peritonitis), pneumonia, or an infection brought about by an intravenous catheter.

Diagnostic problem: A clinically relevant question which is important for a patient's treatment, for example: prediction of the progress of the disease, therapy monitoring, focus of the infection, chances of survival, predisposition, etc.

A systemic infection is an infection where the pathogens have been spread to the entire organism via the bloodstream.

SIRS: Systemic Inflammatory Response Syndrome: according to Bone [Bone et al., 1992] and Levy [Levy et al., 2003] a generalized, inflammatory, non-infectious condition of a patient.

Sepsis: According to Bone [Bone et al., 1992] and Levy [Levy et al., 2003] a generalized, inflammatory infectious condition of a patient.

Biological fluid: Biological fluids within the meaning of the invention are understood to be any body fluids of mammals including man.

Gene: A gene is a section on the desoxyribonucleic acid (DNA) that contains the basic information for the production of a biologically active ribonucleic acid (RNA) as well as regulatory elements which activate or inactivate such production. Genes within the meaning of the invention are furthermore understood to be any derived DNA sequences, partial sequences, and synthetic analoga (e.g., peptido-nucleic acids (PNA)). The description of the invention relating to determination of the gene expression on the RNA level thus expressly does not constitute a limitation but only an exemplary application.

Gene locus: Gene locus is the position of a gene in the genome. Where the genome consists of several chromosomes, this refers to the position within the chromosome on which the gene is located. Various expressions or variants of this gene are termed alleles which are all situated in the same location on the chromosome, namely, the gene locus. The term "gene locus" thus encompasses the pure genetic information for a specific gene product on the one hand, and on the other hand any regulatory DNA sections as well as any additional DNA sequences that are in any functional context with the gene at the gene locus. The latter connect to sequence regions which are situated in the immediate vicinity (1 Kb) but outside of the 5' and/or 3' end of a gene locus. Specification of the gene locus takes place by way of the accession number and/or RefSeq ID des RNA main product originating from this locus.

Gene activity: Gene activity is understood to be the measure of the capability of a gene to be transcribed and/or to form translation products.

Gene expression: The process of forming a gene product and/or expression of a genotype into a phenotype.

Multigene biomarker: A combination of several gene sequences whose gene activities form a combined overall result (e.g., a classification and/or an index) by means of an interpretation function. This result is specific for a condition and/or a diagnostic problem.

Hybridization conditions: Physical and chemical parameters that are well-known to the person having skill in the art and that are capable of influencing the establishment of a thermodynamic equilibrium of free and bound molecules. In the interest of optimum hybridization conditions, duration of the contact of probe and sample molecules, cation concentration in the hybridization buffer, temperature, volume, as well as concentrations and concentration ratios of the hybridizing molecules must be harmonized with each other.

Amplification conditions: Constant or cyclically changing reaction conditions which allow the reproduction of the starting material having the form of nucleic acids. In the reaction mixture the single components (deoxynucleotides) for the nucleic acids to be formed are present, just like short oligonucleotides which may attach to complementary regions in the starting material, as well as a nucleic acid synthesis enzyme termed polymerase. Cation concentrations, pH value, volume, and the duration and temperature of the single reaction steps that are well-known to the skilled person are of importance for the progress of the amplification.

Primer: What is called a primer in the present invention is an oligonucleotide serving as a starting point for nucleic acid-replicating enzymes such as, e.g., DNA polymerase. Primers may be made up both of DNA and RNA (Primer3; cf., e.g., http://frodo.wi.mit.edu/cgi-bin/primer3/primer3_www.cgi of the MIT)

Probe: In the present application, a probe is a nucleic acid fragment (DNA or RNA) which may be provided with a molecular label (e.g., fluorescence labels, in particular Scorpion®, molecular beacons, Minor Groove Binding probes, TaqMan® probes, isotope labeling, etc.) and that is employed for the sequence-specific detection of target DNA molecules and/or target RNA molecules.

PCR: is the abbreviation for the English-language term "Polymerase Chain Reaction." The polymerase chain reaction is a method for reproducing DNA in vitro outside of a living organism with the aid of a DNA-dependent DNA polymerase. PCR is employed, in particular in accordance with the present invention, in order to reproduce short portions—up to about 3,000 base pairs—of a DNA strand of interest. This may be a gene or only part of a gene, or also non-coding DNA sequences. The person having skill in the art is well aware that a number of PCR methods, all of which are encompassed by the expression "PCR", are known in the prior art. This is in particular true for "real-time PCR" (also cf. the explanations given further below).

PCR primer: A PCR typically requires two primers in order to fix the starting point for DNA synthesis on the respective two single strands of the DNA, whereby the region to be reproduced is limited from both sides. Such primers are well-known to the person having skill in the art, for example from the web site "Primer3"; cf., e.g., http://frodo.wi.mit.edu/cgi-bin/primer3/primer3_www.cgi of MIT.

Transcript: For the purposes of the present application, a transcript is understood to be any RNA product that is produced with the aid of a DNA template.

small RNA: Small RNAs in general. Representatives of this group are in particular, however not exclusively:

a) scRNA (small cytoplasmatic RNA), which is one from among several small RNA molecules in the cytoplasm of a eukaryote.

b) snRNA (small nuclear RNA), one of the many small RNA forms that occur only in the cell core. Some of the snRNAs play a role in splicing or in other RNA-processing reactions.

c) small non-protein-coding RNAs, which include the so-called small nucleolar RNAs (snoRNAs), microRNAs (miRNAs), short interfering RNAs (siRNAs) and small double-stranded RNAs (dsRNAs), which enable gene expression on many levels, including the chromatin architecture, RNA editing, RNA stability, translation, and possibly also transcription and splicing. In general, these RNAs are processed via multiple paths from the introns and exons of longer primary transcripts, including protein-coding transcripts. Although only about 1.2% of the human genome codes proteins, a large part is nevertheless transcribed. As a matter of fact, about 98% of the transcripts found in mammals and humans are made up of non-protein-coding RNAs (ncRNA) from introns of protein-coding genes and from the exons and introns of non-protein-coding genes, including many which are antisense to protein-coding genes or overlap with these. Small nucleolar RNAs (snoRNAs) regulate the sequence-specific modification of nucleotides in target RNAs. Here two types of modifications occur, namely, 2'-O-ribose methylation and pseudouridylation, which are regulated by two large snoRNA families referred to as box C/D-snoRNAs on the one hand and box H/ACA snoRNAs on the other hand. Such snoRNAs exhibit a length of about 60 to 300 nucleotides. miRNAs (microRNAs) and siRNAs (short interfering RNAs) are even smaller RNAs generally including 21 to 25 nucleotides. miRNAs originate from endogenous short hairpin precursor structures and usually employ other loci having similar—not, however, identical—sequences as a target of translational repression. siRNAs form from longer double-stranded RNAs or long hairpins, frequently of exogenous origin. They usually target homolog sequences on a same locus or in some other location in the genome where they are involved in the so-called gene silencing, a phenomenon also referred to as RNAi. The borders between miRNAs and siRNAs are, however, fluid.

d) In addition, the expression "small RNA" may also encompasss so-called transposable elements (TEs) and in particular retroelements, which are also understood under the expression "small RNA" for the purposes of the present invention.

RefSeq ID: This designation relates to entries in the NCBI database (www.ncbi.nlm.nih.gov). This database provides non-redundant reference standards for genomic information. This genomic information i. a. includes chromosomes, mRNAs, RNAs, and proteins. Each RefSeq ID represents a single, naturally occurring molecule of an organism. The biological sequences representing a RefSeq are derived from GenBank entries (also NCBI), but are a compilation of information elements. These information elements originate from primary research on the DNA, RNA, and protein levels.

Accession number: An accession number represents the entry number of a polynucleotide in the NCBI-GenBank which is known to the person having skill in the art. In this database both RefSeq ID's and less-well characterized and redundant sequences are managed as entries and made accessible to the public (www.ncbi.nlm.nih.gov/genbank/index.html).

| | Abbreviations |
|---|---|
| AUC | Area Under Curve |
| CRP | C-Reactive Protein |
| CV | Cross-Validation |
| DLDA | Diagonal Linear Discriminant Analysis (classification method) |
| GPLS | Generalized Partial Least Squares (classification method) |
| IQR | Inter Quartile Range (distance between the 75% and 25% percentiles) |
| kNN | k Nearest Neighbors (classification method) |
| LDA | Linear Discriminant Analysis (classification method) |
| MAD | Median of the Absolute Deviation of the median (normalization method) |
| NPV | Negative Predictive Value (proportion of correct negative tests) |
| OR | Odd Ratio |
| PCT | Procalcitonin |
| PPV | Positive Predictive Value (proportion of correct positive tests) |
| RF | Random Forests (classification method) |
| ROC | Receiver Operator Characteristics (Map for the representation of classification results |
| Sensitivity | Proportion of correct tests in the group with a predetermined disorder (infectious SIRS or sepsis) |
| Specificity | Proportion of correct tests in the group without a predetermined disorder (non-infectious SIRS) |
| SVM | Support Vector Machines (classification method) |

It was found in practice that real-time amplification methods are the preferred methods for a rapid diagnosis. The basics, which are well-known to the person having skill in the art, shall thus be summarized briefly with a view to their importance for the present invention.

Other methods known to the skilled person such as, e.g., sequencing, microarray-based methods, NASBA, etc., are equally possible.

The polymerase chain reaction (PCR) allows in vitro and moreover rapid amplification of specific sequence regions from minimum starting quantities of nucleic acids, to thus make them available for an analysis or for further processing. A double-stranded DNA molecule is melted (denatured) by the effect of heat. The single strands subsequently serve as a template for the enzymatically catalyzed polymerization of deoxyribonucleotides, thus again resulting in the formation of double-stranded DNA molecules. The oligodeoxyribonucleotides referred to as primers here define the sequence section to be copied by hybridizing with the target DNA in places of complementary sequence and serving as starters for the polymerization. The process of exponential product formation is restricted by various factors. In the course of the PCR, the net product formation thus finally goes down to zero, with the total amount of PCR product reaching a plateau value.

Suitable PCR primers are, for example, primers including the sequences of SEQ ID NO: 687 to SEQ ID NO: 742. It is, however, well-known to the person having skill in the art that a multiplicity of additional primers may be used for carrying out the present invention.

Since its introduction into the range of molecular-biological methods, a virtually immensely large number of technical variants was developed. At present, PCR is one of the most important methods in molecular biology and molecular medicine. It is nowadays being used in a very wide range of topics, e.g., in the detection of viruses or germs, in sequencing, proof of kinship, compilation of transcription profiles, and quantification of nucleic acids [Valasek and Repa, 2005; Klein, 2002]. With the aid of PCR it is moreover possible in an easy way to clone any sequence sections of the totality of an organism's nucleic acids. The multitude of developed PCR variants i. a. allows a deliberate or random alteration of the DNA sequence and even the synthesis of larger sequence successions which previously had not existed in this form.

This classical method allows highly sensitive detection of DNA and even qualitative detection of RNA by way of reverse transcription (RT) [Wong et al., 2005; Bustin 2002]. One further development of this method is the real-time PCR which was introduced for the first time in 1991 and also allows quantification in addition to qualitative statements.

Real-time PCR, also referred to as quantitative PCR (qPCR), is a method for the detection and quantification of nucleic acids in real time [Nolan et al., 2006]. In molecular biology it has already been part of the established standard techniques for several years.

Other than in PCR, detection here already takes place during amplification. On the basis of fluorescence-labeled probes—the fluorophores—amplification may be tracked in real time. In every reaction cycle the fluorescent PCR products and thus the intensity of the light-induced fluorescence emission increase. As the increase in fluorescence and the quantity of newly synthesized PCR products are proportional over a wide range, the obtained data allows to determine the starting quantity of the template. Separation of the amplificates by gel electrophoresis is no longer necessary. The results are immediately available, which results in clear time savings. As the reactions unfold in closed vessels and no more pipetting steps are required after starting the PCR, the contamination risk is reduced to minimum. Fluorophores being used are either nucleic acid-binding fluorescence dyes such as SYBRGreen or sequence-specific fluorescence probes such as Taq-Man probes, LightCycler probes, and Molecular Beacons [Kubista et al., 2006]. SYBRGreen is a dye whose fluorescence increases strongly once the molecule binds to double-stranded DNA. This cost-effective solution is particularly suitable in the parallel performance of several reactions with different primer pairs. Drawbacks reside in a low specificity because SYBRGreen binds to any double-stranded DNA in a manner that is not sequence-specific, and in the circumstance that it is not possible to perform multiplex measurements. After the PCR is completed, it is nevertheless possible to differentiate between target product and nonspecific DNA with the aid of a melting curve analysis: Depending on the nucleotide length and composition, every DNA double strand decomposes into its two single strands at a temperature that is characteristic for it—the melting temperature. As the double-stranded DNA of specific PCR products has a higher melting point than nonspecific produced primer dimers, a differentiation is enabled by the decrease in fluorescence accompanying temperature increases.

In contrast, detection by fluorescence-based probes is highly specific but also very cost-intense. In the case of the TaqMan principle, the PCR batch contains besides the PCR primers a sequence-specific TaqMan hybridization probe including a quencher and a reporter dye. The probe is complementary with a sequence situated between the primers. In free solution, fluorescence is suppressed by the physical proximity of the quencher. In accordance with the FRET (Fluorescence Resonance Energy Transfer) principle, the quencher absorbs the fluorescence emission of the stimulated fluorophore. If this probe hybridizes with the target sequence, however, it is hydrolyzed during the PCR of the Taq-Polymerase, the reporter dye is put at a physical distance from the quencher, and upon stimulation emits detectable fluorescence. In the case of the LightCycler principle, the PCR batch contains, besides the PCR primers, two fluorescence-marked probes (donor and acceptor fluorescence dyes). An outwardly measurable fluorescence signal is engendered only with immediately adjacent hybridization of the two probes with the specific target sequence. In the framework of a subsequent melting curve analysis, even the presence and type of individual point mutations can be detected within the hybridization regions. Another example is constituted by the molecular beacons. These oligonucleotides contain at the 5' and 3' ends two complementary sequences which hybridize in the unbound condition and form a hairpin structure. Reporter fluorophore and quencher localized at both ends thus are located in immediate vicinity. The two dyes are only physically removed from each other when the probe binds to the template, so that fluorescence can again be measured following stimulation. Scorpion and Sunrise Primer constitute two further modifications for sequence-specific probes [Whitcombe et al,. 1999].

The quantitative determination of a template may take place by means of absolute or relative quantification. In absolute quantification, the measurement takes place by way of external standards, e.g., plasmid DNA at various degrees of dilution. Relative quantification, on the other hand, makes use of so-called housekeeping or reference genes as a reference [Huggett et al., 2005]. Expression of these reference genes is constant, so that they offer an option of standardizing different expression analyses. The selection of the housekeeping gene must be made individually for each experiment. For the present invention, housekeeping genes having the sequences of SEQ ID NO: 676 to SEQ ID NO: 686 are preferably used.

The generated experimental data is evaluated with the aid of the internal software of the apparatus. For graphic representation, the measured fluorescence intensity is plotted over the number of cycles. The resulting curve thus is subdivided into three areas. In the first phase, i.e., at the beginning of the reaction, background noise is still predominant, with a signal of PCR products not being detectable yet. The second phase corresponds to the exponential growth phase. In this segment, the DNA template is doubled approximately at every reaction step. What is crucial for the evaluation is the cycle at which the detectable fluorescence appears and the exponential phase of amplification begins. This threshold cycle (CT) value, or also crossing point, furnishes the basis for the calculation of the starting quantity of existing target DNA. In an absolute quantification, the software thus determines the crossing point of the various reference dilutions and quantifies the template quantity with the aid of the calculated standard curve. In the last phase, the reaction finally reaches a plateau.

Quantitative PCR is an important tool for gene expression studies in clinical research. The possibility of accurately quantifying mRNA allows, in the search for new active agents, to analyze the effects of particular factors on cells, observe the differentiation of precursor cells in various cell types, or track the gene expression in host cells as a response to infections. The comparison of wild type and cancer cells on the RNA level allows the identification in the cell culture of genes which have a decisive influence on the genesis of cancer. In routine lab diagnostics, real-time PCR is predominantly employed for the qualitative and quantitative detection of viruses and bacteria. In clinical routine, in particular in the field of intensive care medicine, the physician requires rapid and unambiguous findings. On the basis of real-time PCR it is possible to perform tests that deliver the result even on the same day. This is the basis for an enormous advance for the clinical diagnostics of sepsis.

Apart from the presently described technical variants of the PCR method, it is also possible to use so-called isothermal amplification methods such as, e.g., NASBA or SDA or other technical variants for the reproduction of the target sequence preceding the detection.

A preferred method for selecting the multigene biomarker sequences includes the following steps:
a. patient selection based on the extreme group approach;
b. generating at least one multigene biomarker;
c. determining final multigene biomarkers.

A preferred method of the test similar to "in vitro diagnostic multivariate index assay" includes the following steps:
a. isolating sample nucleic acids from a sample originating from a patient;
b. detecting gene activities by means of sequences of at least one multigene biomarker that is specific for a condition and/or diagnostic problem;
c. detecting gene activities for at least one internal reference gene in order to normalize the gene activities detected in b);
d. use of an interpretation function for the gene activities normalized in c) in order to derive an index that is specific for a condition and/or a diagnostic problem.

As a technical reference, the gene activities of control genes are suitably also determined, e.g. those having the sequences SEQ ID NO: 670 to SEQ ID NO: 675.

A preferred embodiment of the present invention furthermore resides in a use wherein the gene activities are determined by means of a hybridization method, in particular on at least one microarray. The advantage of a microarray lies in the higher information density of the biochip as compared with the amplification methods. Thus it is, e.g., readily possible to provide several hundreds of probes on one microarray in order to simultaneously examine several problems in a single examination.

The gene activity data obtained by means of the invention may advantageously also be used for electronic further processing, e.g., for recording in a patient's electronic medical file.

Another embodiment of the invention consists in the use of recombinant or synthetically produced, specific nucleic acid sequences, partial sequences, singly or in partial quantities, as multigene biomarkers in sepsis assays and/or for assessing the effect and toxicity in active ingredient screening and/or for the production of therapeutic preparations and of substances and mixtures of substances intended as a therapeutic preparation, for the prophylaxis and treatment of SIRS and sepsis.

For the method of the invention (array technique and/or amplification method), the sample is selected from: tissue, body fluids, in particular blood, serum, plasma, urine, saliva, or cells or cell components; or a mixture thereof.

It is preferred if samples, in particular cell samples, are subjected to a lytic treatment in order to release their cell contents.

What is disclosed to this end are polynucleotide sequences of SEQ ID NO: 1 to SEQ ID NO: 669 from blood and blood cells as well as probes derived therefrom, which may be used for producing multigene biomarkers (cf. Table 32).

Tables 11 and 16 exemplarily show a sequence selection for multigene biomarkers for the differentiation of infectious/non-infectious conditions, and Tables 20 and 21 exemplarily show a sequence selection for multigene biomarkers for the differentiation of gram-positive and gram-negative infections.

The skilled person will be aware that the single features of the invention set forth in the claims may be combined at will and without restrictions.

Classification Methods

Learning theory is of key importance in the fields of statistics, data analysis, and artificial intelligence, with numerous applications in the engineering sciences. Classification methods are primarily used in 2 different tasks: in the discrimination of previously unknown classes (unsupervised learning, class discovery) and in the association of particular data/samples/patients with a previously defined class (class prediction) [Golub et al., 1999].

In class prediction, data/samples/patients are used which had already been associated to previously existing or defined classes/groups (so-called training data set) in order to develop an analytic method (classification algorithm) reflecting the differences between groups. Independent samples (so-called test data set) were used for evaluating the quality of separation of the classification rule. The manner of proceeding can be subdivided into the following steps:
1. Define an ideal data/sample/patient set in order to obtain characteristic profiles of the groups to be detected.
2. Each group is then split such as to form 2 equivalent quantities, a training data set, and a test data set.
3. Profiles for the training data set ideally contain data reflecting a maximum difference between the groups.
4. The difference between the groups is quantified by means of appropriate measures of distance and evaluated by means of an algorithm. This algorithm should lead to a classification rule which assigns the correct class to the data with the highest specificity and sensitivity. Typical representatives of such algorithms from the field of unsupervised learning are discriminant analysis (DA), random forests (RF), generalized partial least squares (GPLS), support vector machines (SVM), or k nearest neighbors (kNN).
5. Finally, the quality of the classification rule is tested on the test data set.

Definitions:

Discriminant analysis (DA): In linear discriminant analysis a linear discriminant function is obtained, while a quadratic discriminant function is obtained in quadratic discriminant analysis (QDA). The discriminant function is determined by the covariance matrix and the group averages.

Quadratic discriminant analysis is under the additional assumption that the covariance matrix also varies between the groups [Hastie et al., 2001].

Random forests (RF): Classification by means of random forests is based on the combination of decision trees [Breiman, 2001]. The algorithm runs approximately as follows:
1. Select training data set by drawing with replacement (out-of-bag data).
2. At each node of the decision tree, randomly select variables. Use these variables to calculate the best classification of the training data set to the classes.
3. Once all of the decision trees have been generated, summarize the class assignments of the individual decision trees into one class assignment.

Generalized partial least squares (GPLS): The generalized partial least squares [Ding and Gentleman, 2004] method is a very flexible generalization of the multiple regression model. Owing to its high flexibility, this method may also be utilized in many situations where the classical model fails.

Support vector machine (SVM): The support vector machine classifier is a generalized linear classifier. The input data is mapped in a higher-dimensional space, and an optimum separating (hyper) plane is constructed in this space. These limits, which are linear in the higher-dimensional space, transform to non-linear limits in the space of the input data [Vapnik, 1999].

k nearest neighbors (kNN): In the method of k nearest neighbors, the class association of an observation (of a patient) is decided by way of the k nearest neighbors present in its neighborhood. As a general rule, the neighborhood is determined with the aid of the Euclidian distance, and the class association is then decided by a majority vote [Haste et al., 2001].

The following describes a general concept of how the methods of the invention are performed. It is here well-known to the person having skill in the art that minor adaptations of the statistical methods may be necessary if other groups of patients and/or other problems are to be investigated. In order to generate the training and test sets of data, different statistical methods (discriminant analysis and/or random forests etc.) as well as strategies (simple and multiple cross-validation, random bootstrap samples etc.) are used.

Based on microarray expression data, a method for determining a multigene biomarker should be developed which reflects an infectious complication such as, e.g., sepsis. The biomarker and the associated index value, also referred to as "score", form the basis of a so-called "in vitro diagnostic multivariate index assay" [IVDMIA, FDA-Guidelines, 2003] for improving the diagnosis of systemic infections. The classification rule resulting from the method should in particular enable a differentiation of SIRS and sepsis patients with enhanced sensitivity and specificity in comparison with the conventional biomarker procalcitonin, but is not restricted to this problem.

The development of such a multigene biomarker requires the following steps:

$1^{st}$ Step: training data set. In order to reveal the interrelation between a gene expression of particular genes and the studied disorder, populations (cohorts) are defined which represent the presence or absence thereof most clearly. In the diagnosis of an infectious complication, sepsis patients (infectious) and patients with a so-called sterile SIRS (non-infectious) are usually included in the study. A plan for collecting or selecting the associated RNA samples is set in accordance with this determination. From the selected samples, the gene expression profiles are measured on a suitable platform, pre-processed, and subjected to quality control. Systematic measurement errors are corrected, and freak values are eliminated.

2nd Step: Gene preselection. Gene preselection is a key step in the generation of a formal classifier on the basis of microarray data, for only a small proportion of measured genes provides a contribution to group differentiation. Most classification methods also require gene selection. Accurate gene selection allows to configure the classification method with maximum possible simplicity and to avoid overadaptation to the training data (overfilling). For the preselection of the classification genes, suitable filtering options such as the threshold of statistical inference, the minimum accepted distance between the groups, the minimum signal intensity, etc. are set. Only genes satisfying such conditions are considered for the classification.

$3^{rd}$ Step: Classification method. Various classification methods are tested concerning their separability with regard to the pathophysiological conditions to be differentiated. Cross-validation methods are used to this end. A classification method having the smallest classification error is selected, with the lowest necessary number of genes jointly being determined in the process. It was found to be a sensible rule that the number of genes should always be smaller than the number of samples in the training data set in order to avoid overadaptation. Finally, the resulting classification rule is defined.

Patient selection Patient selection is of significance in assembling the training data set. In a preliminary study in the framework of the present invention, a sensitivity of approx. 75% in the training data set and approx. 65% in the test data set was achieved for the time being. This relatively low classification quality could, however, be explained not by poor optimization of the classifier but by the insufficiently accurate selection of sepsis patients. Accordingly, sepsis patients after a peritonitis were much more frequently classified correctly than sepsis patients after a "VAR" (ventilator-associated pneumonia). As a matter of fact, the infectious complication as such exists following a peritonitis. In cases of VAP, on the other hand, a real infection can only with difficulty be differentiated from a colonization [Mayhall, 2001].

In an evaluation of the quality of patient selection, the principle of so-called extreme groups can be useful. Accordingly, a study only considers those patient groups which map the studied effect as clearly as possible. Here, the selected random samples represent an idealized case in which many effects occurring in practice (e.g., the frequency of the disorder) are disregarded. It was proposed by Liu [Liu et al., 2005] to form extreme groups for the training data set of a microarray-based classifier. It was demonstrated by the example of the survival analysis of cancer patients that the use of extreme groups (patients having died after a short time vs. patients having survived for a long time) resulted in a higher preselection of classification genes and in a higher classification quality, even if the training data set was made up of less profiles (patients) than in the usual case in which all of the patients (even those with average survival periods) were taken into consideration.

It shall be discussed in the following to what extent patient selection can influence the generation of a multigene biomarker for a diagnosis of the infectious complication. In one study by the applicant, patients having developed sepsis after massive surgery were examined. Samples from the first day of the diagnosis sepsis were compared to the sample from the first post-operative day. The genes which are here expressed differentially in a significant degree do, however, reflect a mixed effect; the infectious complication is obscured by effects such as recovery from operative stress or the post-operative treatment. In the pilot study already mentioned in the foregoing, the patients having a clinical (not always microbiologically confirmed) diagnosis of sepsis were included in the training population, which led to mixing of the two studied groups (septics and controls) and downgraded sensitivity. In the practical example of US patent application No. 20060246495, the clinical diagnosis of sepsis was also used for the selection of the sepsis group. In addition, the severity of the disorder was not taken into consideration between the group of sepsis patients and the control group of SIRS patients. This may be the reason for the poor quality of classification and its dependency on the classification algorithm. In the study by Johnson [Johnson et al., 2007], patients after a trauma were divided into two groups, one with an infectious complication and one without an infection. The advantage of this study was that patients of the two groups showed little difference in co-morbidity and pre-treatment. The preselection is, however, not representative for all sepsis patients, and the generalization of the presently revealed, sepsis-relevant gene expression pattern to patients of different backgrounds (to other risk groups) is not self-evident. In general it must be assumed that studies including different risk groups also require the generation of different classifiers. In the study by Tang [Tang et al., 2007a] the principle of extreme groups was applied indirectly, by considering only patients with a microbiologically confirmed sepsis diagnosis being in the training data set. The sample collection plan did, however, result in a smaller control group (one-third of samples: 14 from among 44). Accordingly, a specificity of 77% was reached in the training, and merely 60% in an independent test data set (subject to more real-life-conditions). The description of the patient groups in the SIRS-Lab study and in the study by Tang [Tang et al., 2007a] reveals another influencing factor. It shows that the sepsis groups which were heterogeneous in regard of the focus of infection are not balanced, but groups with different foci of infection are represented differently. Actually, in the majority of cases in the intensive care unit (ICU), the lungs (approx. 45-50%) or the abdomen (approx. 25%) were the focus of infection in a diagnosis of sepsis. These patient groups accordingly are overrepresented in the studies, with many other foci thus only appearing sparsely. Similarly, in particular post-operative and trauma patients are represented in the control groups, and other risk groups are represented only by single patients. The represented analysis shows that in all of the studies the selected patient groups do not unambigously represent the infectious complication, which may serve to explain the classification inadequacies. In turn, it becomes clear from grouping that it is hardly possible to consider the totality of factors of influence in the selection of the patient groups in the case of infectious complication. For this reason the following way for patient selection for the training data set is being proposed.

General Information on Materials and Methods of the Present Invention:

Patient Selection

The selection of the representative random samples was of central importance in the described method. Patients with a microbiologically confirmed or excluded diagnosis of infection from two each of the sepsis or control sub-groups represented best were included in the training data set. Thus, the principle of extreme groups is applied not only for the main effect (infectious vs. non-infectious) but also for the control of the most important influence quantities (stratification of populations). The advantage of this selection is foremost the generation of a classifier for the most common risk or disease groups. In addition it is expected that a classifier reflecting the systemic infection for few, but very varied subgroups may be applied to other patient groups. The selection of training data was carried out as follows. 400 ICU patients with a suspected sepsis risk were included in the applicant's patient database in a time frame of two-and-a-half years, and the associated clinical data was documented in detail over their entire stay. The RNA samples were collected over approx. 7-14 sepsis-relevant days. In approximation of the PIRO concept [Levy et al., 2003], the patients were stratified retrospectively according to the following criteria: (i) which indication resulted in transfer to the intensive care unit (post-operative complication, trauma or polytrauma, acute suspicion of sepsis), (ii) was an infectious complication diagnosed, what was the focus of infection, (iii) what was the organism's reaction (number of existing SIRS criteria, shock treatment, PCT and CRP values), (iv) what was the severity of the disorder (SOFA, MODS score). The database search showed that in cases of infectious complication (sepsis), in particular patients after a pneumonia (40%) and after a peritonitis (23%) were included in the study. Without an infection, in particular patients after a (poly) trauma (9%) and after bypass surgery (20%) were included. This data corresponds to the epidemiological studies of the Deutsche Sepsisgesellschaft, so that the collection was rated to be representative. The patient data of these groups was examined independently by two physicians [according to ACCP/SCCM, 1992; Levy et al., 2003; Calandra and Cohen, 2005], and the final patient selection was set. 46 patients having a microbiologically confirmed diagnosis were selected from the two sepsis groups, and the first septic day was determined. Grouping of the severity criteria showed that the patients were diagnosed with a severe sepsis or a septic shock on this day. They reached an average SOFA value of 10, the sum of acute organ dysfunctions was approximately 3. 59 patients without an indication of an infection were selected from the two risk groups (after CPB surgery and/or trauma), and the first day having a severity similar to the sepsis groups was determined. In this way, 105 patients were primarily included in the study; after the quality control of the associated microarray experiments, the group was restricted to 96 patients with good quality of the gene expression measurement. A listing for important clinical and laboratory parameters for the selected patients is given exemplarily, however without restriction thereto, in Table 1.

TABLE 1

Clinical and laboratory parameters of exemplarily selected patients, grouped according to the clinical groups.

|  | Peritonitis | Pneumonia | CPB | Trauma |
| --- | --- | --- | --- | --- |
| No. patients | 25 | 18 | 35 | 18 |
| Mortality | 64.0% | 44.4% | 20.0% | 0.0% |
| Sex [m/f] | 15/10 | 16/2 | 21/14 | 13/5 |
| Age* [yrs] | 68 (14) | 70 (11) | 70 (12) | 28 (19) |
| SIRS criteria* | 3 (2) | 3 (0.75) | 3 (1) | 3 (1.75) |
| SOFA score* | 10 (4) | 11 (2.75) | 7 (3) | 10 (5) |
| No. ODF* | 3 (1) | 3.5 (1) | 3 (1) | 2 (2) |
| PCT* [ng/ml] | 21.1 (35.5) | 4.2 (6.4) | 3.3 (10.0) | 1.2 (6.1) |

TABLE 1-continued

Clinical and laboratory parameters of exemplarily selected patients, grouped according to the clinical groups.

|  | Peritonitis | Pneumonia | CPB | Trauma |
|---|---|---|---|---|
| CRP* [mg/l] | 167.9 (92) | 250 (119) | 67.4 (49) | 19.1 (27.5) |
| WBC* [no/l] | 12900 (8400) | 12600 (5650) | 14600 (7300) | 9350 (4350) |

Generation of the Classifier

On the way to developing the classifier, the following steps were performed:

Step 1. Quality control: Based on the preselection from a group of patients which was confirmed on expert knowledge, the associated gene expression data was subjected to various similarity analyses in order to exclude non-typical hybridization results [Buneβ at al., 2005], to thereby generate the final training data matrix.

Step 2. Normalization or pre-processing of data: Various methods of background correction and normalization were compared. Methods including a variance-stabilizing transformation were found to be best [Rocke and Durbin, 2001]. It was found that the best normalization method was the normalization by means of Box-Cox [Box and Cox, 1964], followed by median and MAD standardization. Its advantage, namely, the normalization of single profiles (as compared with normalization of the entire data matrix according to, e.g., Huber [Huber et al., 2003]), was in particular used purposely for the bootstrap.

Step 3. Filter: A filter was used in order to identify the best classifier genes. The filter was comprised of the following steps:

(i) Selection of a particular number of transcripts having the fewest variation coefficients, with only transcripts having a positive mean signal intensity being taken into consideration. (ii) After this, the Wilcoxon test was performed for these transcripts for a comparison of infectious vs. not infectious. The transcripts were arranged by means of the p values, with all transcripts having a p value <=0.001 being considered equivalent and being arranged by means of the distance between infectious and non-infectious group. The distance between the two groups was determined by means of the Hodges-Lehmann estimator [Hollander and Wolfe, 1973].

Step 4. Classification: The best ones of the selected transcripts were then used for classification. In the classification step, various linear and non-linear methods [Hastie et al., 2001] were compared to each other: DLDA, LDA, RE, GPLS, SVM and kNN.

Step 5. Internal validation: In order to evaluate the quality of classification, the 10-fold cross-validation was used, with the cross-validation being repeated several times (20 and even 1000 times).

Step 6. Selection of the transcripts: The final selection of transcripts for the classifier took place by using bootstrap. In statistics, bootstrapping is a method of resampling where statistics are calculated repeatedly on the basis of merely one random sample x=(x(1), . . . , x(n)). B bootstrap random samples x(b)=(x*(1), . . . , x*(n)), b=1, . . . , B for this are generated in the most simple case by drawing a value with replacement n times each from the given random sample [Efron, 1979].

Thus, particular bootstrap random samples that were appropriate for the respective problem were drawn from the original training data set, and the optimum transcripts were determined for each one of these random samples in accordance with the above description. The final classifier contains transcripts that were selected most often in frequent repetitions, e.g., 5000 repetitions.

Determination of the Final Classifier

Appraisal of the dependency of the classification results on the number of genes confirms the result by Baker and Kramer [Baker and Kramer, 2006], namely, that the results with 5, 10, 25, 40, and 50 genes showed little difference. In FIG. 1 the classification error for the linear discriminant analysis (LDA) is represented. As the curve reaches its minimum at about 12 features, the results obtained with this number of genes were represented from then on. The results of the various classification methods, which were obtained by means of 20 repetitions of a 10-time cross-validation, were summarized in Table 2.

TABLE 2

Sensitivity and specificity estimated by means of 20-time CV (cross-validation) at simultanous appraisal of 12 transcripts

|  | DLDA | LDA | RF | GPLS | SVM | 5-NN |
|---|---|---|---|---|---|---|
| Sensitivity | 95.3 | 95.3 | 95.3 | 93.0 | 97.7 | 90.7 |
| Specificity | 84.9 | 94.3 | 90.6 | 94.3 | 92.5 | 96.2 |

It may be seen from Table 2 that the estimated sensitivity is in the range of 95%, and the estimated specificity—except with DLDA—in the range of more than 90%. The results by means of LDA and SVM are the most promising. In both of these classification methods only few predominantly false classifications of patients resulted, with a misclassification rate of 5% at the most being thus achieved. Owing to the high complexity of the SVM method and the resulting calculation cost that would be brought about by the optimization of an SVM classifier, as well as the better biological interpretability of a classifier on the basis of LDA, the applicant decided to develop the classifier on the basis of LDA. The classification rule resulting from the LDA was converted to a score. The score for an exemplary group of 96 patients is represented in FIG. 2. A value >10 shows that an infection (i.e., sepsis) is highly likely. At a value between +10 and −10 there is a certain risk of sepsis. A value <−10 finally indicates that an infection is highly unlikely.

In summary, one arrives at the following picture: The classifier generation process shows the advantages of the group selection: the estimated number of classification genes is small, with an overadaptation (overfitting) to the training data thus being unlikely. The single classification methods differ only slightly. (The fact that diagonal linear discriminant analysis [DLDA] yields the poorest quality of classification as a classification method may be explained through the fact that the correlation between the genes is not taken into consideration in DLDA, resulting in information loss). An increase in the number of genes does not improve the result. These facts are an indication that the groups may be separated well in the training data set, i.e., they exhibit clear distances.

The present invention shall in the following be explained in more detail by way of examples and by making reference to the sequence protocol which also forms part of this description, without this amounting to a restriction of the invention.

Results

The quality of the multigene biomarkers in accordance with the invention was compared to the conventional biomarkers PCT and CRP, for which purpose the associated ROCs for the training data set were calculated (FIG. 3). One obtains as the AUC (Area Under the Curve): AUC(PCT)=0.326, AUC (CRP)=0.656, AUC(PCT & CRP)=0.940, AUC(multigene biomarker)=0.997. These ROC curves underline the very high sensitivity at a similarly high specificity for the multigene biomarker. Due to the specific selection of the classification genes, the multigene biomarker thus achieved a better quality of classification than the conventional markers PCT and CRP, and this also for the training data which represent sharp differences according to the principle of extreme groups.

In the next step, the gene expression data of the applicant's patient database, which was not used in the training data set, was subjected to a classification. FIG. 4a shows the distribution of the score values in dependence on the clinical diagnosis. For comparison, the distribution of the PCT and CRP values for the same set of data is represented in FIG. 4b. While the index values or the scores match the clinical diagnosis, the PCT distribution in particular shows that a severe SIRS is rather rated as sepsis, and an uncomplicated sepsis is rather rated as non-infectious. An unspecific distribution is exhibited by the markers CRP and WBC (leucocyte count).

The quality of the multigene biomarkers of the invention and of the method of the invention was examined by using expression data of additional patients of an external collecting institution. Here, too, the clinical and molecular-biological rating matched in 90% of cases.

FIG. 5 finally represents the score curve in the course of the disorder for individual patients. Here, too, the multigene biomarker of the present invention reflects the clinical diagnosis.

The validation analysis was made to include patient profiles of the applicant's patient database whose expression profiles were not represented in the training data set. Due to the missing gold standard for the diagnosis of sepsis, this independent test data set was examined in stratified subgroups, with patient profiles being grouped and classified according to severity of the disorder (cf. FIG. 4). Patients with uncomplicated SIRS were in fact almost exclusively rated as non-infectious. Patients with severe SIRS (SIRS with additional multiple organ dysfunction (MOD)) were predominantly recognized as not infectious. Patients with uncomplicated sepsis were predominantly classified als systemically infectious. The infectious complication was ascertained most frequently among the patients with severe sepsis or septic shock. This finding could be confirmed on a group of patients who were recruited and diagnosed in an independent institution (FIG. 6).

Further advantages and features of the present invention result from the description of practical examples and from the drawings, wherein.

PRACTICAL EXAMPLES

Example 1

Sepsis/SIRS Discrimination

It is intended to disclose a method for determining multigene biomarkers. The classification rule resulting from the methods is to enable a differentiation of SIRS and sepsis patients. Another classification rule is to enable the differentiation between the focus of infection pneumonia and peritonitis.

Experimental Approach

In genome-wide gene expression studies of the blood of non-septic and septic patients, transcripts were identified which reflect the molecular differences between groups of sepsis patients irrespective of the heterogeneity of the patients brought about by age, co-morbidities, and medications. The number of biomarkers necessary for a successful classification differs depending on the group of patients being examined.

It is assumed that heterogeneous groups make it necessary to analyze more biomarkers than in very well-defined groups. One starts out from a pool of significant biomarkers with a view to maximum robustness of clinical diagnostics. Depending on the diagnostic problem, biomarkers are then selected, and the classification method is optimized on various technical gene expression platforms. The potential of the biomarker candidates shall be made clear by referring to two examples:

a) Measurement of Differential Gene Expression Between SIRS and Sepsis Patients on a Microarray b) Classification of SIRS and Sepsis Patients with Gene Expression Signals of Selected Oligonucleotide Probes Generated on the Microarray re a:

Characteristics of the Array Used:

Oligonucleotide microarray produced by means of spotting technology 484 gene-specific oligonucleotides are applied in 3 replicates of these, 344 oligonucleotides address gene expression biomarkers 84 oligonucleotides address controls (neg. and pos.)

56 oligonucleotides address reference genes

Figure 7:
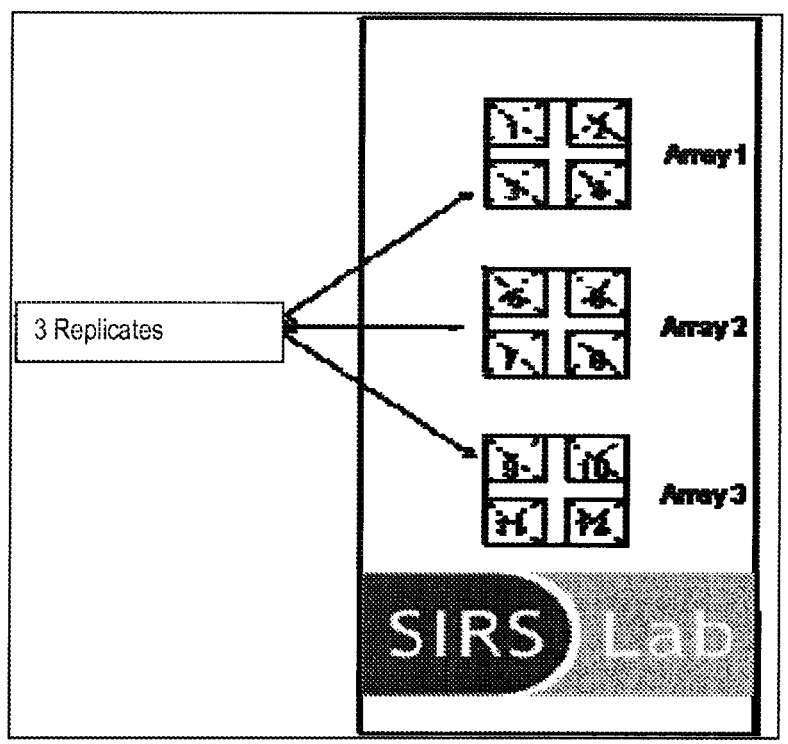
FIG. 7 is a schematic representation of the microarray design and the three replicates.

FIG. 7 shows a schematic representation of the focused sepsis microarray. Spotted on epoxy-silanized glass supports (Nexterion E-Slides, Manufacturer Schott, Federal Republic of German), each gene-specific oligonucleotide is represented three times. The three identical sub-arrays are hybridized with a patient sample. Besides the marker-specific oligonucleotides, probes for controls (monitoring of the entire sample preparation and hybridization process) are also represented on the array.

Figure 8:
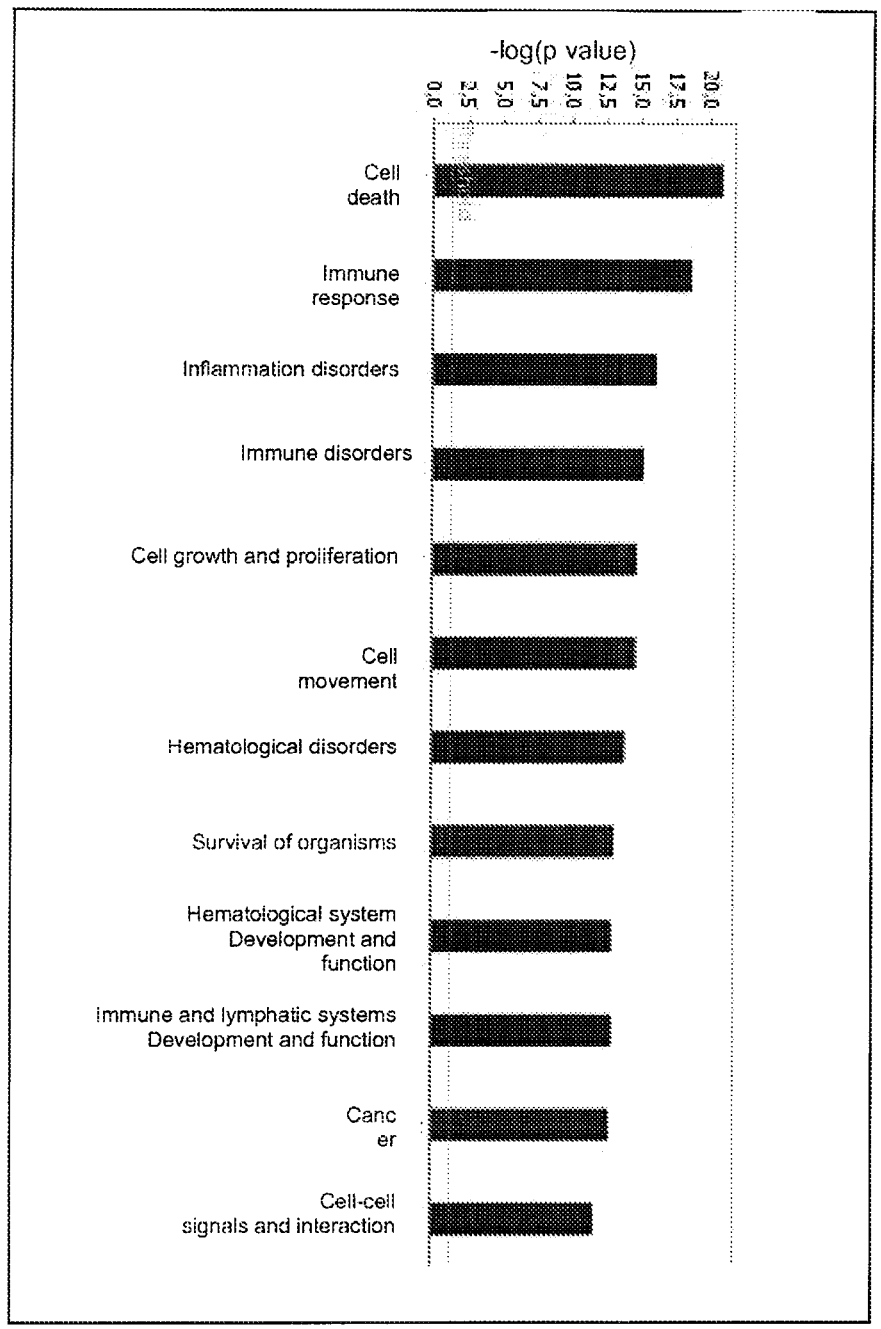
FIG. 8 is a representation of the signal paths represented on the microarray.

Biological Plausibility of the Biomarkers Used:

The marker genes addressed on the array are associated with high significance to the signal paths in the human cell as represented in FIG. 8 and to the associated functionalities. High relevance for immunological and inflammatory processes, and thus also for sepsis, exists. For the knowledge-based analysis of the biomarker population on the focused sepsis array the software Ingenuity Pathway Analysis (Ingenuity Systems, USA, www.ingenuity.com) was used in order to underline the functional context of the identified markers. Based on the entire publicly available database knowledge concerning genes and gene products, the markers are integrated into functional networks which may then possess relevance for physiological and pathological processes. The markers participate with high significance in immunological and inflammatory processes, which allows the assumption of an intimate connection with sepsis under a functional aspect. Biological plausibility, a basic precondition for biomarkers, thus exists.

Patient Group for the Evaluation:

In the majority of cases in the intensive care unit (ICU), the lungs (approx, 45-50%) or the abdomen (approx. 25%) are the focus of infection in a diagnosis of sepsis. In the framework of multigene biomarker development, patients with pneumonia and peritonitis, respectively, were therefore selected. In the case of SIRS, heart patients were selected which represent the majority of SIRS patients in an ICU. In this way, 12 patients with severe pneumonia, 18 patients with severe peritonitis, and 19 heart patients (OP: cardiopulmonal bypass) with severe SIRS were identified. For the analyses, the respective first day of diagnosis of these patients was selected. In the following Table 3, the group of patients for the classifier validation is represented on the sepsis array.

TABLE 3

Patient group for the validation of the classifier on the focused sepsis array (for clinical data, see description total group of 96 patients)

| No. | Specification | Patient |
|---|---|---|
| 1 | Peritonitis | 1021 |
| 2 | Peritonitis | 6008 |
| 3 | Peritonitis | 6008 |
| 4 | Peritonitis | 6023 |
| 5 | Peritonitis | 6023 |
| 6 | Peritonitis | 6023 |
| 7 | Peritonitis | 6025 |
| 8 | Peritonitis | 6035 |
| 9 | Peritonitis | 6073 |
| 10 | Peritonitis | 6075 |
| 11 | Peritonitis | 6084 |
| 12 | Peritonitis | 6118 |
| 13 | Peritonitis | 6127 |
| 14 | Peritonitis | 6132 |
| 15 | Peritonitis | 6138 |
| 16 | Peritonitis | 6040 |
| 17 | Peritonitis | 6065 |
| 18 | Peritonitis | 6096 |
| 19 | CPB | 814 |
| 20 | CPB | 2038 |
| 21 | CPB | 2042 |
| 22 | CPB | 2043 |
| 23 | CPB | 8001 |
| 24 | CPB | 8002 |
| 25 | CPB | 8009 |
| 26 | CPB | 8010 |
| 27 | CPB | 8032 |
| 28 | CPB | 8039 |
| 29 | CPB | 8068 |
| 30 | CPB | 8096 |
| 31 | CPB | 8102 |
| 32 | CPB | 8111 |
| 33 | CPB | 8112 |
| 34 | CPB | 8116 |
| 35 | CPB | 7072 |
| 36 | CPB | 7073 |
| 37 | CPB | 7134 |
| 38 | Pneumonia | 877 |
| 39 | Pneumonia | 1015 |
| 40 | Pneumonia | 6032 |
| 41 | Pneumonia | 6085 |
| 42 | Pneumonia | 6141 |
| 43 | Pneumonia | 8089 |
| 44 | Pneumonia | 6070 |
| 45 | Pneumonia | 6104 |
| 46 | Pneumonia | 6109 |
| 47 | Pneumonia | 6007 |
| 48 | Pneumonia | 6048 |
| 49 | Pneumonia | 6063 |

Hybridization:

4 µg of total RNA from patient blood was transcribed by means of reverse transcription (SuperscriptII, Invitrogen, USA) in a reaction volume of 30 µl in cDNA. As a primer, a PolydT primer (18 mer) was utilized. Aminoallyl-dUTP was added to the reaction, to thus substitute 80% of the quantity of dTTP in the mRNA strand by means of the AA-dUTP (Table 4).

TABLE 4

Pipetting batch for the samples for the cDNA synthesis. 4 µg of total RNA and 2.5 µg of OligodT primer were employed. RNAse-free water was used to fill up to a total volume of 30 µl.
Reaction batch

| Constituents | Samples |
|---|---|
| 5x RT buffer | 6 µl |
| 50x dNTP | 0.6 µl |
| 0.1M DTT | 3 µl |

TABLE 4-continued

Pipetting batch for the samples for the cDNA synthesis. 4 µg of total RNA and 2.5 µg of OligodT primer were employed. RNAse-free water was used to fill up to a total volume of 30 µl.
Reaction batch

| Constituents | Samples |
|---|---|
| RNase Out | 0.4 µl |
| Superscript II | 2 µl |
| Total RNA | 4 µg |
| RNAase-free water | to 30 µl |

All samples are incubated during 2 hrs at 42° C. After these 2 hrs, the formed mRNA/cDNA duplexes are subjected to alkaline hydrolyzation to single-stranded cDNA (addition of 20 µl of 0.5 M EDTA (pH 8.0) each and 20 µl of 1 N NaOH each, with an incubation period of 30 min at 65° C.). 50 µl of 1M Tris-HCl (pH 7.4) each are added for neutralization of the single-stranded cDNA. Then all the samples are admixed with 400 µl of Rnase-free $H_2O$ and purified by means of Microcon YM-30 columns (AM ICON, USA). To this end, all of the samples are placed on a respective column which is centrifuged at 11000×g during 10 min. After washing twice with 450 µl of RNase-free $H_2O$ and intermediate 10-min centrifuging steps at 11000×g, the columns are reversed and placed over a new 1.5-ml reaction vessel and centrifuged during 3 min at 15000×g. As the eluate, one now obtains purified single-stranded cDNA having a volume of approx. 20-40 µl which is reduced to dryness in the Speedvac.

Labeling the cDNA with Fluorescence Dyes

Fluorescent dyes are used for detection of the hybridization signals. For the analyses a fluorescence dye by Dyomics was used (Manufacturer: Dyomics GmbH, Jena, Federal Republic of Germany). DY-647 (Cy5 analogs) are purchased in the form of N-hydroxy succinimide ester (NHS ester) and utilized for fluorescence labeling. Chemical coupling of the dyes takes place on the inserted AA-dUTPs.

The cDNA is dissolved in 10 µl of $H_2O$ and divided at 5 µl each into two test tubes. The dissolved samples are incubated at 42° C. during 5 min. Then, 3 µl of bicarbonate buffer is added to each sample. The fluorescence dye is dissolved in DMSO (Manufacturer: SIGMA-Aldrich, Federal Republic of Germany). 75 µg of dye is used for each sample.

This light-sensitive reaction takes place in the dark during 1 h. After this period, the samples are filled up with $H_2O$ to a final volume of 30 µl. The samples are each pipetted together with 80 µl of $H_2O$ and 100 µl of membrane-binding solution and purified by means of Promega kit (Promega Wizard-SV Gel and PCR CleanUP System, PROMEGA, USA) in accordance with the manufacturer's specifications.

In the last step, the columns are centrifuged dry during 1 min at 16000×g and eluted twice with 50 µl of $H_2O$ (1 min each, 10000×g). Then each sample is admixed with 10 µl of Cot-1-DNA (Invitrogen, USA) and 400 µl of $H_2O$. Concentrating the labeled samples is carried out by means of Microcon YM-30 (10000×g; 10 min of centrifugation). The columns are reversed and placed over a new test tube and centrifuged at 15000×g during 3 min. The volume of the cDNA/Cot-1-DNA mixture is set to 32 µl. The fluorescence-labeled cDNA/Cot-1-DNA mixture (32 µl) is admixed with 58 µl of hybridization mixture (Table 5).

Following denaturing during three minutes at 98° C., the mixture is pipetted into the hybridization chambers of the TECAN hybridization automaton (HS-400, Manufacturer Tecan, Austria). The obtained formamide lowers the melting temperature of the hybrid and thus allows good hybridization. Wetting of the biomolecules on the glass slide is improved by addition of 10-% SDS. The yeast-t-RNA/Poly-A mix prevents non-specific binding and background noise. Accordingly, Poly(A) binds to the Poly(T) end of the labeled cDNA, with the yeast-t-RNA blocking any nonspecific sequences.

TABLE 5

The hybridization mixture for a sample

| Constituents of the hybridization mixture | Volumes |
|---|---|
| Formamide | 21.60 µl |
| 20x SSC | 15.66 µl |
| 10% SDS | 2.70 µl |
| Yeast-t-RNA/polyA mix (10.0 µg/µl each) | 14.40 µl |
| Rnase.free $H_2O$ | 3.64 µl |

The program at the hybridization station is represented in the following Table 6.

TABLE 6

The program of the standardized and controlled hybridization on the Tecan apparatus.

| Program | Solutions | Temperature | No. & durations of runs |
|---|---|---|---|
| 1. Washing step | Hybridization solution (0.3% SDS, 3.5X SSC, 24% formamide) | 42.0° C. | 2 runs; time: 1 min; absorption time: 30 sec |
| 2. Sample injection | | 42.0° C. | |
| 3. Hybridization | | 42.0° C. | Agitation frequency: medium; time: 10 h |
| 4. Washing step 1 | Washing solution 1 (2x SSC/ 0.03% SDS) | 25.0° C. | 2 runs; time: 1 min; absorption time: 30 sec |
| 5. Washing step 2 | Washing solution 2 (1x SSC) | 25.0° C. | 2 runs; time: 1 min; absorption time: 30 sec |
| 6. Washing step 3 | Washing solution 3 (0.2x SSC) | 25.0° C. | 1 run; time: 1 min; absorption time: 30 sec |
| 7. Slide drying | | 30.0° C. | Time: 2 min 30 sec; final drying with nitrogen supplied at 2.5 bars |

At the beginning, the arrays are washed with hybridization solution and subsequently incubated with the samples. The process is performed during ten hours at a temperature of 42° C. in hybridization chambers of the Tecan apparatus HS-400 with constant agitation of the hybridization mixture on the array surface. At the end, the arrays are washed and dried in three automated steps.

After ten hours, any unbound molecules are removed from the microarray by subsequent washing steps. The finished arrays must be scanned for evaluation (AxonB scanner, GenePix software, Axon Technologies, USA). The resulting gpr files are evaluated biostatistically.

Evaluation

The data analysis was carried out under the free software R Project Version 2.6.1 which is available under www.r-project.org.

1. Quality Control of the Raw Data:

Of the preselection from 46 patients confirmed by expert knowledge, the associated gene expression data was subjected to various similarity analyses in order to exclude non-typical hybridization results [Buneß et al., 2005].

2. Normalization of the Data:

Various methods of background correction and normalization were compared. Methods with a variance-stabilizing transformation [Rocke and Durbin, 2001] were found to be best. Normalization by means of Box-Cox [Box and Cox, 1964] with subsequent median and MAD standardization was found to be the best normalization method. Its advantages, namely, the normalization of individual profiles (as compared with normalization of the entire data matrix according, e.g., to Huber [Huber et al., 2003], may in particular be used specifically for bootstrapping.

3. Statistical Comparison of the Groups:

The expression values of the examined transcripts were compared by the Wilcoxon rank-sum test according to the infection status (infectious vs. non-infectious). The transcripts were arranged ascendingly in accordance with the achieved p value, with all transcripts having a p value <=0.001 being considered to be equivalent and being arranged by means of the distance between infectious and non-infectious group. The distance between the two groups was determined by means of the Hodges-Lehmann estimator.

4. Classification:

14 transcripts which were best capable of separating the patient groups in a classification test in accordance with their infection status were selected from Table 7. The linear discriminant analysis [Hastie et al., 2001] was selected as the best classification method (i.e., the method yielding the smallest classification error in a simple cross-validation). For this the function lda from the MASS packet of the software R was used. For the p=14 gene markers the weights ($w_0, \ldots, w_p$) of the discriminant function $f_{LD}$, which is defined by the formula $$f_{LD}(x_1, \ldots, x_p) = \sum_{i=1}^{p} w_i x_i - w_0$$

were calculated from the normalized expression data by successively omitting one sample each. This sample was classified later on, for which the ct values of the sample were inserted in the above formula for ($x_1, \ldots, x_p$). The weights of the discriminant function were calculated such that a positive value of the function means the association to the group with an infectious complication and a negative value of the function means the association to the group without an infectious complication. The weights of the linear discriminant function, which were calculated from all of the samples, are summarized in Table 7.

re b):

Classification Results:

The expression signals used originate from the above set of data. In the classification, a sensitivity of 96% and a specificity of 95% were achieved at a simple cross-validation. This corresponds to an error rate of 96%, i.e., a false classification of 2 samples. The weights of the associated discriminant function are summarized in Table 7.

TABLE 7

Weights of the linear discriminant function as a result of classification

| Weighting factor | Gene symbol | SEQ ID | Determined values |
|---|---|---|---|
| w0 | — | — | 9.5 |
| w1 | KIAA0146 | 261 | 3.6 |
| w2 | FGL2 | 615 | -3.9 |
| w3 | CCR2 | 529, 530 | -2.7 |
| w4 | HLA_DPA | 613 | -26.1 |
| w5 | CD59 | 571, 572, 573, 574 | 16 |
| w6 | EPC1 | 280 | 23.5 |
| w7 | TLR5 | 431 | -5.2 |
| w8 | CLU | 575, 576 | 15.4 |
| w9 | MME | 443, 444, 445, 446 | -11.3 |
| w10 | IGKCem | 633 | 0.5 |
| w11 | NSMAF | 527 | 13.7 |
| w12 | CCR2 | 529, 530 | 23.9 |
| w13 | BZRP | 601, 602 | -20.6 |
| w14 | CD82 | 470, 471 | -14.4 |

Table 8 shows the differential gene expression in the patient groups as measured on the microarray.

TABLE 8

Differential gene expression between the patient groups; p values for analyses 1 and 2: the markers shaded in grey are those markers exhibiting a significant difference between the groups for the respective analysis; Analysis1 (non-infectious vs. infectious cause of the multiple organ failure): CPB patients vs. septic patients with peritonitis or pneumonia focus; Analysis2 (focus of the infection, differentiation of peritonitis focus from pneumonia focus): 18 septic patients with peritonitis focus vs. 12 patients with pneumonia focus

| Analysis 1: Infectious/non-infectious | | | Analysis 2: Pneumonia/Peritonitis as the focus in septic patients | | |
|---|---|---|---|---|---|
| Seq ID | p value | Hodge-Lehmann estimator | Seq-ID | p value | Hodge-Lehmann estimator |
| 530 | 0 | -0.516 | 236 | 0.000014 | 0.962 |
| 546 | 0 | 0.241 | 356 | 0.000056 | -0.62 |
| 588 | 0 | 0.219 | 540 | 0.000244 | 0.339 |
| 613 | 0 | -0.645 | 540 | 0.000319 | 0.399 |
| 340 | 0.000002 | 0.411 | 215 | 0.001067 | 0.335 |
| 530 | 0.000002 | -0.505 | 235 | 0.001067 | -0.405 |
| 626 | 0.000009 | -0.404 | 161 | 0.001333 | -0.492 |
| 599 | 0.000027 | -0.412 | 364 | 0.001653 | -0.361 |
| 600 | 0.000027 | -0.412 | 365 | 0.001653 | -0.361 |
| 527 | 0.000044 | -0.231 | 18 | 0.00204 | 0.172 |
| 546 | 0.00005 | 0.244 | 413 | 0.00204 | 0.349 |
| 621 | 0.000056 | 0.233 | 414 | 0.00204 | 0.349 |
| 436 | 0.000062 | 0.157 | 415 | 0.00204 | 0.349 |
| 615 | 0.000062 | -0.331 | 416 | 0.00204 | 0.349 |
| 324 | 0.00007 | 0.158 | 12 | 0.003054 | 0.318 |
| 619 | 0.000097 | -0.365 | 13 | 0.003054 | 0.318 |
| 620 | 0.000097 | -0.365 | 162 | 0.003054 | 0.372 |
| 518 | 0.000108 | -0.336 | 272 | 0.003054 | -0.358 |
| 628 | 0.000134 | -0.182 | 571 | 0.003054 | 0.203 |
| 438 | 0.000166 | -0.298 | 572 | 0.003054 | 0.203 |
| 439 | 0.000166 | -0.298 | 573 | 0.003054 | 0.203 |
| 501 | 0.000184 | 0.17 | 574 | 0.003054 | 0.203 |
| 519 | 0.000184 | 0.394 | 636 | 0.003054 | 0.396 |
| 296 | 0.000226 | 0.17 | 233 | 0.00448 | -0.247 |
| 408 | 0.00025 | 0.201 | 538 | 0.00448 | -0.272 |
| 409 | 0.00025 | 0.201 | 539 | 0.00448 | -0.272 |
| 410 | 0.00025 | 0.201 | 175 | 0.005386 | 0.199 |
| 411 | 0.00025 | 0.201 | 204 | 0.005386 | 0.452 |
| 412 | 0.00025 | 0.201 | 465 | 0.005386 | 0.296 |
| 504 | 0.00025 | 0.382 | 61 | 0.006447 | -0.239 |
| 57 | 0.000277 | 0.147 | 62 | 0.006447 | -0.239 |
| 183 | 0.000277 | 0.293 | 325 | 0.006447 | -0.291 |
| 42 | 0.000306 | -0.145 | 326 | 0.006447 | -0.291 |
| 207 | 0.000306 | 0.135 | 538 | 0.006447 | -0.286 |

TABLE 8-continued

Differential gene expression between the patient groups; p values for analyses 1 and 2: the markers shaded in grey are those markers exhibiting a significant difference between the groups for the respective analysis; Analysis1 (non-infectious vs. infectious cause of the multiple organ failure): CPB patients vs. septic patients with peritonitis or pneumonia focus; Analysis2 (focus of the infection, differentiation of peritonitis focus from pneumonia focus): 18 septic patients with peritonitis focus vs. 12 patients with pneumonia focus

| Analysis 1: Infectious/non-infectious | | | Analysis 2: Pneumonia/Peritonitis as the focus in septic patients | | |
|---|---|---|---|---|---|
| Seq ID | p value | Hodge-Lehmann estimator | Seq-ID | p value | Hodge-Lehmann estimator |
| 515 | 0.000306 | −0.147 | 539 | 0.006447 | −0.286 |
| 516 | 0.000306 | −0.147 | 635 | 0.006447 | 0.267 |
| 259 | 0.000338 | −0.259 | 167 | 0.007681 | 0.415 |
| 179 | 0.00041 | 0.197 | 178 | 0.007681 | 0.227 |
| 180 | 0.00041 | 0.197 | 327 | 0.009114 | −0.233 |
| 552 | 0.000452 | −0.296 | 328 | 0.009114 | −0.233 |
| 631 | 0.000452 | 0.201 | 384 | 0.009114 | −0.193 |
| 454 | 0.000497 | −0.251 | 443 | 0.009114 | −0.449 |
| 520 | 0.000497 | 0.135 | 444 | 0.009114 | −0.449 |
| 521 | 0.000497 | 0.135 | 445 | 0.009114 | −0.449 |
| 45 | 0.0006 | 0.206 | 446 | 0.009114 | −0.449 |
| 46 | 0.0006 | 0.206 | 18 | 0.010767 | 0.192 |
| 47 | 0.0006 | 0.206 | 208 | 0.010767 | −0.351 |
| 48 | 0.0006 | 0.206 | 355 | 0.010767 | −0.423 |
| 424 | 0.0006 | 0.156 | 552 | 0.010767 | −0.214 |
| 425 | 0.0006 | 0.156 | 567 | 0.010767 | 0.257 |
| 426 | 0.0006 | −0.246 | 581 | 0.010767 | 0.236 |
| 7 | 0.000658 | 0.177 | 35 | 0.01267 | −0.135 |
| 596 | 0.000658 | 0.204 | 36 | 0.01267 | −0.135 |
| 522 | 0.000721 | −0.245 | 37 | 0.01267 | −0.135 |
| 523 | 0.000721 | −0.245 | 38 | 0.01267 | −0.135 |
| 524 | 0.000721 | −0.245 | 39 | 0.01267 | −0.135 |
| 525 | 0.000721 | −0.245 | 40 | 0.01267 | −0.135 |
| 526 | 0.000721 | −0.245 | 41 | 0.01267 | −0.135 |
| 529 | 0.000721 | −0.286 | 368 | 0.01267 | 0.224 |
| 530 | 0.000721 | −0.286 | 369 | 0.01267 | 0.224 |
| 249 | 0.000865 | 0.315 | 370 | 0.01267 | 0.224 |
| 250 | 0.000865 | 0.315 | 371 | 0.01267 | 0.224 |
| 470 | 0.000865 | 0.17 | 372 | 0.01267 | 0.224 |
| 471 | 0.000865 | 0.17 | 373 | 0.01267 | 0.224 |
| 601 | 0.000946 | 0.221 | 379 | 0.01267 | −0.302 |
| 602 | 0.000946 | 0.221 | 20 | 0.014847 | −0.253 |
| 420 | 0.001034 | 0.303 | 21 | 0.014847 | −0.253 |
| 421 | 0.001034 | 0.303 | 22 | 0.014847 | −0.253 |
| 168 | 0.001129 | 0.2 | 23 | 0.014847 | −0.253 |
| 197 | 0.001129 | 0.246 | 24 | 0.014847 | −0.253 |
| 611 | 0.001232 | −0.247 | 25 | 0.014847 | −0.253 |
| 612 | 0.001232 | −0.247 | 26 | 0.014847 | −0.253 |
| 376 | 0.001344 | 0.158 | 27 | 0.014847 | −0.253 |
| 430 | 0.001344 | 0.253 | 28 | 0.014847 | −0.253 |
| 542 | 0.001344 | 0.139 | 29 | 0.014847 | −0.253 |
| 543 | 0.001344 | 0.139 | 30 | 0.014847 | −0.253 |
| 544 | 0.001344 | 0.139 | 31 | 0.014847 | −0.253 |
| 545 | 0.001344 | 0.139 | 32 | 0.014847 | −0.253 |
| 387 | 0.001464 | 0.247 | 33 | 0.014847 | −0.253 |
| 388 | 0.001464 | 0.247 | 50 | 0.014847 | −0.265 |
| 423 | 0.001464 | −0.324 | 51 | 0.014847 | −0.265 |
| 528 | 0.001594 | 0.324 | 52 | 0.014847 | −0.265 |
| 337 | 0.001886 | 0.202 | 53 | 0.014847 | −0.265 |
| 338 | 0.001886 | 0.202 | 54 | 0.014847 | −0.265 |
| 469 | 0.001886 | −0.244 | 55 | 0.014847 | −0.265 |
| 302 | 0.002049 | 0.18 | 56 | 0.014847 | −0.265 |
| 441 | 0.002049 | 0.248 | 243 | 0.014847 | −0.182 |
| 568 | 0.002225 | 0.153 | 456 | 0.014847 | 0.241 |
| 569 | 0.002225 | 0.153 | 457 | 0.014847 | 0.241 |
| 295 | 0.002413 | 0.22 | 458 | 0.014847 | 0.241 |
| 460 | 0.002413 | −0.3 | 459 | 0.014847 | 0.241 |
| 247 | 0.002835 | 0.173 | 177 | 0.017335 | −0.121 |
| 364 | 0.002835 | 0.287 | 270 | 0.017335 | 0.134 |
| 365 | 0.002835 | 0.287 | 312 | 0.017335 | 0.184 |
| 248 | 0.00332 | 0.333 | 313 | 0.017335 | 0.184 |
| 350 | 0.00332 | 0.168 | 385 | 0.017335 | 0.265 |
| 273 | 0.00359 | 0.216 | 405 | 0.017335 | 0.225 |
| 581 | 0.00359 | −0.269 | 406 | 0.017335 | 0.225 |
| 594 | 0.003878 | 0.176 | 407 | 0.017335 | 0.225 |
| 571 | 0.004187 | 0.256 | 438 | 0.017335 | −0.282 |
| 572 | 0.004187 | 0.256 | 439 | 0.017335 | −0.282 |
| 573 | 0.004187 | 0.256 | 583 | 0.017335 | 0.121 |
| 574 | 0.004187 | 0.256 | 584 | 0.017335 | 0.121 |
| 304 | 0.004518 | 0.152 | 58 | 0.02016 | 0.163 |
| 401 | 0.004518 | 0.282 | 59 | 0.02016 | 0.163 |
| 451 | 0.004518 | 0.184 | 199 | 0.02016 | 0.249 |
| 452 | 0.004518 | 0.184 | 460 | 0.02016 | −0.326 |
| 561 | 0.004518 | −0.179 | 533 | 0.02016 | −0.186 |
| 601 | 0.004518 | 0.24 | 593 | 0.02016 | 0.151 |
| 602 | 0.004518 | 0.24 | 258 | 0.023364 | 0.28 |
| 330 | 0.004871 | 0.17 | 297 | 0.023364 | 0.275 |
| 331 | 0.004871 | 0.17 | 468 | 0.023364 | 0.219 |
| 332 | 0.004871 | 0.17 | 518 | 0.023364 | −0.261 |
| 333 | 0.004871 | 0.17 | 615 | 0.023364 | −0.19 |
| 334 | 0.004871 | 0.17 | 621 | 0.026976 | 0.128 |
| 335 | 0.004871 | 0.17 | 211 | 0.031043 | 0.158 |
| 475 | 0.004871 | −0.217 | 249 | 0.031043 | −0.258 |
| 476 | 0.004871 | −0.217 | 250 | 0.031043 | −0.258 |
| 623 | 0.004871 | 0.23 | 434 | 0.031043 | 0.283 |
| 221 | 0.005652 | 0.122 | 435 | 0.031043 | 0.283 |
| 222 | 0.005652 | 0.122 | 437 | 0.031043 | 0.281 |
| 223 | 0.005652 | 0.122 | 442 | 0.031043 | −0.114 |
| 462 | 0.005652 | −0.132 | 473 | 0.031043 | −0.118 |
| 463 | 0.005652 | −0.132 | 474 | 0.031043 | −0.118 |
| 464 | 0.005652 | −0.132 | 619 | 0.031043 | −0.187 |
| 581 | 0.005652 | −0.245 | 620 | 0.031043 | −0.187 |
| 64 | 0.006541 | 0.218 | 624 | 0.031043 | −0.202 |
| 65 | 0.006541 | 0.218 | 341 | 0.035598 | 0.15 |
| 196 | 0.006541 | 0.192 | 342 | 0.035598 | 0.15 |
| 509 | 0.006541 | −0.207 | 563 | 0.035598 | 0.156 |
| 510 | 0.006541 | −0.207 | 564 | 0.035598 | 0.156 |
| 511 | 0.006541 | −0.207 | 595 | 0.035598 | 0.18 |
| 512 | 0.006541 | −0.207 | 163 | 0.040689 | −0.18 |
| 43 | 0.00703 | 0.195 | 164 | 0.040689 | −0.18 |
| 44 | 0.00703 | 0.195 | 165 | 0.040689 | −0.18 |
| 213 | 0.00703 | 0.091 | 166 | 0.040689 | −0.18 |
| 276 | 0.00703 | 0.232 | 359 | 0.040689 | −0.223 |
| 467 | 0.007551 | −0.196 | 530 | 0.040689 | −0.19 |
| 645 | 0.007551 | −0.179 | 637 | 0.040689 | −0.161 |
| 175 | 0.008695 | 0.147 | 638 | 0.040689 | −0.161 |
| 592 | 0.008695 | 0.143 | 639 | 0.040689 | −0.161 |
| 456 | 0.009321 | −0.152 | 640 | 0.040689 | −0.161 |
| 457 | 0.009321 | −0.152 | 641 | 0.040689 | −0.161 |
| 458 | 0.009321 | −0.152 | 642 | 0.040689 | −0.161 |
| 459 | 0.009321 | −0.152 | 15 | 0.046354 | −0.22 |
| 522 | 0.009321 | −0.193 | 366 | 0.046354 | −0.217 |
| 523 | 0.009321 | −0.193 | 502 | 0.046354 | 0.136 |
| 524 | 0.009321 | −0.193 | 503 | 0.046354 | 0.136 |
| 525 | 0.009321 | −0.193 | 586 | 0.046354 | −0.194 |
| 526 | 0.009321 | −0.193 | 628 | 0.046354 | −0.084 |
| 422 | 0.009986 | −0.175 | 159 | 0.052643 | 0.114 |
| 535 | 0.009986 | −0.309 | 387 | 0.052643 | 0.146 |
| 609 | 0.009986 | −0.154 | 388 | 0.052643 | 0.146 |
| 258 | 0.010693 | −0.198 | 422 | 0.052643 | −0.199 |
| 283 | 0.010693 | 0.177 | 514 | 0.052643 | 0.152 |
| 215 | 0.012237 | 0.232 | 532 | 0.052643 | −0.166 |
| 218 | 0.012237 | 0.131 | 534 | 0.052643 | −0.251 |
| 616 | 0.012237 | 0.215 | 594 | 0.052643 | 0.174 |

TABLE 8-continued

Differential gene expression between the patient groups; p values for analyses 1 and 2: the markers shaded in grey are those markers exhibiting a significant difference between the groups for the respective analysis; Analysis1 (non-infectious vs. infectious cause of the multiple organ failure): CPB patients vs. septic patients with peritonitis or pneumonia focus; Analysis2 (focus of the infection, differentiation of peritonitis focus from pneumonia focus): 18 septic patients with peritonitis focus vs. 12 patients with pneumonia focus

| Analysis 1: Infectious/non-infectious | | | Analysis 2: Pneumonia/Peritonitis as the focus in septic patients | | |
|---|---|---|---|---|---|
| Seq ID | p value | Hodge-Lehmann estimator | Seq-ID | p value | Hodge-Lehmann estimator |
| 617 | 0.012237 | 0.215 | 6 | 0.059596 | 0.19 |
| 618 | 0.012237 | 0.215 | 7 | 0.059596 | −0.129 |
| 19 | 0.013079 | 0.155 | 209 | 0.059596 | 0.169 |
| 635 | 0.013079 | 0.173 | 220 | 0.059596 | 0.17 |
| 263 | 0.01397 | −0.252 | 261 | 0.059596 | −0.148 |
| 264 | 0.01397 | −0.252 | 447 | 0.059596 | −0.25 |
| 443 | 0.01397 | −0.297 | 448 | 0.059596 | −0.25 |
| 444 | 0.01397 | −0.297 | 449 | 0.059596 | −0.25 |
| 445 | 0.01397 | −0.297 | 450 | 0.059596 | −0.25 |
| 446 | 0.01397 | −0.297 | 507 | 0.059596 | 0.189 |
| 479 | 0.01397 | 0.169 | 508 | 0.059596 | 0.189 |
| 405 | 0.014913 | 0.207 | 562 | 0.059596 | 0.138 |
| 406 | 0.014913 | 0.207 | 581 | 0.059596 | 0.199 |
| 407 | 0.014913 | 0.207 | 625 | 0.059596 | −0.197 |
| 235 | 0.015911 | 0.268 | 197 | 0.067266 | 0.134 |
| 245 | 0.015911 | 0.131 | 281 | 0.067266 | 0.135 |
| 305 | 0.015911 | 0.168 | 291 | 0.067266 | 0.48 |
| 204 | 0.016966 | 0.227 | 453 | 0.067266 | 0.52 |
| 440 | 0.016966 | 0.134 | 213 | 0.075691 | 0.082 |
| 278 | 0.018079 | 0.181 | 236 | 0.075691 | 0.201 |
| 290 | 0.021804 | 0.309 | 286 | 0.075691 | −0.175 |
| 314 | 0.021804 | 0.14 | 577 | 0.075691 | 0.131 |
| 327 | 0.021804 | 0.169 | 578 | 0.075691 | 0.131 |
| 328 | 0.021804 | 0.169 | 616 | 0.075691 | −0.269 |
| 399 | 0.021804 | 0.131 | 617 | 0.075691 | −0.269 |
| 400 | 0.021804 | 0.131 | 618 | 0.075691 | −0.269 |
| 598 | 0.021804 | 0.139 | 182 | 0.084927 | 0.142 |
| 531 | 0.023182 | −0.17 | 337 | 0.084927 | 0.119 |
| 597 | 0.023182 | 0.14 | 338 | 0.084927 | 0.119 |
| 161 | 0.026162 | −0.243 | 522 | 0.084927 | −0.169 |
| 351 | 0.026162 | 0.181 | 523 | 0.084927 | −0.169 |
| 352 | 0.026162 | 0.181 | 524 | 0.084927 | −0.169 |
| 353 | 0.026162 | 0.181 | 525 | 0.084927 | −0.169 |
| 354 | 0.026162 | 0.181 | 526 | 0.084927 | −0.169 |
| 383 | 0.026162 | −0.128 | 645 | 0.084927 | 0.197 |
| 208 | 0.027769 | 0.285 | 255 | 0.095012 | 0.172 |
| 227 | 0.029459 | 0.127 | 316 | 0.095012 | −0.133 |
| 228 | 0.029459 | 0.127 | 336 | 0.095012 | −0.114 |
| 229 | 0.029459 | 0.127 | 555 | 0.095012 | 0.115 |
| 230 | 0.029459 | 0.127 | 556 | 0.095012 | 0.115 |
| 231 | 0.029459 | 0.127 | 226 | 0.106 | 0.091 |
| 402 | 0.033098 | 0.135 | 268 | 0.106 | −0.135 |
| 307 | 0.035055 | 0.135 | 296 | 0.106 | 0.097 |
| 308 | 0.035055 | 0.135 | 404 | 0.106 | 0.13 |
| 309 | 0.035055 | 0.135 | 528 | 0.106 | 0.2 |
| 310 | 0.035055 | 0.135 | 550 | 0.106 | 0.132 |
| 311 | 0.035055 | 0.135 | 551 | 0.106 | 0.132 |
| 385 | 0.035055 | 0.156 | 566 | 0.106 | 0.186 |
| 540 | 0.035055 | 0.241 | 232 | 0.117926 | 0.165 |
| 322 | 0.037107 | 0.21 | 253 | 0.117926 | 0.356 |
| 323 | 0.037107 | 0.21 | 429 | 0.117926 | 0.102 |
| 593 | 0.037107 | 0.139 | 504 | 0.117926 | −0.197 |
| 20 | 0.039258 | −0.177 | 202 | 0.130844 | 0.21 |
| 21 | 0.039258 | −0.177 | 218 | 0.130844 | 0.086 |
| 22 | 0.039258 | −0.177 | 242 | 0.130844 | −0.125 |
| 23 | 0.039258 | −0.177 | 244 | 0.130844 | −0.177 |
| 24 | 0.039258 | −0.177 | 280 | 0.130844 | −0.219 |
| 25 | 0.039258 | −0.177 | 345 | 0.130844 | 0.181 |
| 26 | 0.039258 | −0.177 | 346 | 0.130844 | 0.181 |
| 27 | 0.039258 | −0.177 | 517 | 0.130844 | 0.102 |
| 28 | 0.039258 | −0.177 | 14 | 0.144784 | 0.148 |
| 29 | 0.039258 | −0.177 | 251 | 0.144784 | 0.095 |
| 30 | 0.039258 | −0.177 | 265 | 0.144784 | 0.124 |
| 31 | 0.039258 | −0.177 | 282 | 0.144784 | 0.166 |
| 32 | 0.039258 | −0.177 | 324 | 0.144784 | 0.07 |
| 33 | 0.039258 | −0.177 | 461 | 0.144784 | 0.091 |
| 226 | 0.039258 | 0.091 | 478 | 0.144784 | 0.144 |
| 329 | 0.039258 | −0.141 | 541 | 0.144784 | −0.174 |
| 301 | 0.041511 | 0.141 | 601 | 0.144784 | 0.153 |
| 325 | 0.041511 | 0.181 | 602 | 0.144784 | 0.153 |
| 326 | 0.041511 | 0.181 | 613 | 0.144784 | −0.162 |
| 646 | 0.041511 | 0.09 | 200 | 0.159796 | 0.106 |
| 647 | 0.041511 | 0.09 | 225 | 0.159796 | 0.12 |
| 170 | 0.043871 | 0.388 | 237 | 0.159796 | 0.095 |
| 472 | 0.043871 | 0.146 | 252 | 0.159796 | 0.158 |
| 286 | 0.04634 | 0.188 | 262 | 0.159796 | 0.146 |
| 555 | 0.04634 | 0.111 | 288 | 0.159796 | 0.047 |
| 556 | 0.04634 | 0.111 | 304 | 0.159796 | 0.094 |
| 61 | 0.054443 | 0.159 | 17 | 0.175903 | −0.151 |
| 62 | 0.054443 | 0.159 | 66 | 0.175903 | 0.112 |
| 292 | 0.054443 | 0.114 | 187 | 0.175903 | −0.127 |
| 547 | 0.057388 | −0.104 | 191 | 0.175903 | 0.186 |
| 624 | 0.057388 | −0.112 | 192 | 0.175903 | 0.186 |
| 177 | 0.060461 | 0.13 | 193 | 0.175903 | 0.186 |
| 200 | 0.060461 | 0.11 | 194 | 0.175903 | 0.186 |
| 404 | 0.060461 | 0.109 | 224 | 0.175903 | 0.145 |
| 540 | 0.060461 | 0.263 | 317 | 0.175903 | −0.115 |
| 541 | 0.060461 | −0.14 | 318 | 0.175903 | −0.115 |
| 549 | 0.060461 | −0.177 | 424 | 0.175903 | −0.103 |
| 627 | 0.060461 | 0.08 | 425 | 0.175903 | −0.103 |
| 219 | 0.067007 | 0.104 | 519 | 0.175903 | 0.166 |
| 237 | 0.067007 | 0.077 | 534 | 0.175903 | −0.143 |
| 389 | 0.067007 | −0.279 | 535 | 0.175903 | −0.258 |
| 542 | 0.067007 | 0.131 | 565 | 0.175903 | 0.144 |
| 543 | 0.067007 | 0.131 | 579 | 0.175903 | 0.123 |
| 544 | 0.067007 | 0.131 | 580 | 0.175903 | 0.123 |
| 545 | 0.067007 | 0.131 | 43 | 0.193151 | 0.101 |
| 312 | 0.070488 | 0.1 | 44 | 0.193151 | 0.101 |
| 313 | 0.070488 | 0.1 | 64 | 0.193151 | −0.089 |
| 595 | 0.070488 | 0.095 | 65 | 0.193151 | −0.089 |
| 634 | 0.070488 | 0.204 | 314 | 0.193151 | 0.111 |
| 35 | 0.074112 | −0.087 | 374 | 0.193151 | 0.183 |
| 36 | 0.074112 | −0.087 | 646 | 0.193151 | −0.061 |
| 37 | 0.074112 | −0.087 | 647 | 0.193151 | −0.061 |
| 38 | 0.074112 | −0.087 | 205 | 0.211556 | 0.179 |
| 39 | 0.074112 | −0.087 | 210 | 0.211556 | −0.131 |
| 40 | 0.074112 | −0.087 | 278 | 0.211556 | 0.108 |
| 41 | 0.074112 | −0.087 | 292 | 0.211556 | 0.086 |
| 214 | 0.074112 | 0.128 | 367 | 0.211556 | 0.081 |
| 632 | 0.074112 | 0.22 | 382 | 0.211556 | 0.08 |
| 14 | 0.077884 | 0.138 | 505 | 0.211556 | 0.145 |
| 156 | 0.077884 | 0.146 | 530 | 0.211556 | −0.124 |
| 157 | 0.077884 | 0.146 | 201 | 0.231155 | 0.121 |
| 158 | 0.077884 | 0.146 | 227 | 0.231155 | 0.092 |
| 243 | 0.077884 | −0.107 | 228 | 0.231155 | 0.092 |
| 505 | 0.077884 | −0.189 | 229 | 0.231155 | 0.092 |
| 622 | 0.077884 | 0.172 | 230 | 0.231155 | 0.092 |
| 265 | 0.081808 | 0.12 | 231 | 0.231155 | 0.092 |
| 291 | 0.081808 | −0.302 | 298 | 0.231155 | −0.069 |
| 630 | 0.081808 | 0.178 | 383 | 0.231155 | 0.114 |
| 505 | 0.085886 | −0.167 | 467 | 0.231155 | −0.08 |
| 270 | 0.090124 | 0.105 | 501 | 0.231155 | 0.072 |
| 427 | 0.090124 | −0.147 | 609 | 0.231155 | −0.097 |
| 428 | 0.090124 | −0.147 | 19 | 0.251953 | −0.169 |

TABLE 8-continued

Differential gene expression between the patient groups; p values for analyses 1 and 2: the markers shaded in grey are those markers exhibiting a significant difference between the groups for the respective analysis; Analysis1 (non-infectious vs. infectious cause of the multiple organ failure): CPB patients vs. septic patients with peritonitis or pneumonia focus; Analysis2 (focus of the infection, differentiation of peritonitis focus from pneumonia focus): 18 septic patients with peritonitis focus vs. 12 patients with pneumonia focus

| Analysis 1: Infectious/non-infectious | | | Analysis 2: Pneumonia/Peritonitis as the focus in septic patients | | | Analysis 1: Infectious/non-infectious | | | Analysis 2: Pneumonia/Peritonitis as the focus in septic patients | | |
|---|---|---|---|---|---|---|---|---|---|---|---|
| Seq ID | p value | Hodge-Lehmann estimator | Seq-ID | p value | Hodge-Lehmann estimator | Seq ID | p value | Hodge-Lehmann estimator | Seq-ID | p value | Hodge-Lehmann estimator |
| 547 | 0.090124 | −0.101 | 303 | 0.251953 | 0.094 | 3 | 0.168239 | 0.06 | 471 | 0.347446 | 0.056 |
| 553 | 0.090124 | −0.123 | 454 | 0.251953 | −0.169 | 299 | 0.168239 | −0.136 | 9 | 0.374396 | −0.117 |
| 225 | 0.094525 | 0.112 | 462 | 0.251953 | −0.085 | 300 | 0.168239 | −0.136 | 171 | 0.374396 | −0.062 |
| 403 | 0.094525 | 0.119 | 463 | 0.251953 | −0.085 | 319 | 0.168239 | 0.055 | 198 | 0.374396 | −0.105 |
| 607 | 0.094525 | 0.171 | 464 | 0.251953 | −0.085 | 320 | 0.168239 | 0.055 | 238 | 0.374396 | 0.089 |
| 608 | 0.094525 | 0.171 | 475 | 0.251953 | −0.128 | 321 | 0.168239 | 0.055 | 239 | 0.374396 | 0.089 |
| 629 | 0.094525 | 0.083 | 476 | 0.251953 | −0.128 | 191 | 0.175299 | −0.088 | 285 | 0.374396 | 0.122 |
| 275 | 0.099092 | 0.093 | 254 | 0.273981 | 0.125 | 192 | 0.175299 | −0.088 | 585 | 0.374396 | 0.066 |
| 380 | 0.099092 | 0.097 | 375 | 0.273981 | 0.056 | 193 | 0.175299 | −0.088 | 156 | 0.402547 | 0.075 |
| 381 | 0.099092 | 0.097 | 389 | 0.273981 | 0.269 | 194 | 0.175299 | −0.088 | 157 | 0.402547 | 0.075 |
| 587 | 0.10383 | 0.118 | 430 | 0.273981 | −0.113 | 253 | 0.175299 | −0.245 | 158 | 0.402547 | 0.075 |
| 186 | 0.108743 | 0.114 | 551 | 0.273981 | 0.118 | 262 | 0.175299 | 0.131 | 176 | 0.402547 | −0.092 |
| 453 | 0.108743 | 0.21 | 587 | 0.273981 | 0.072 | 566 | 0.175299 | 0.122 | 181 | 0.402547 | −0.071 |
| 211 | 0.113833 | 0.105 | 601 | 0.273981 | 0.121 | 357 | 0.182573 | 0.071 | 219 | 0.402547 | 0.075 |
| 577 | 0.113833 | 0.116 | 602 | 0.273981 | 0.121 | 650 | 0.182573 | 0.086 | 240 | 0.402547 | 0.061 |
| 578 | 0.113833 | 0.116 | 629 | 0.273981 | 0.039 | 159 | 0.190064 | 0.088 | 284 | 0.402547 | −0.112 |
| 6 | 0.119105 | 0.121 | 1 | 0.297233 | 0.079 | 240 | 0.190064 | 0.06 | 305 | 0.402547 | −0.069 |
| 182 | 0.119105 | 0.091 | 2 | 0.297233 | 0.079 | 280 | 0.197774 | 0.101 | 319 | 0.402547 | 0.064 |
| 633 | 0.119105 | 0.233 | 3 | 0.297233 | 0.079 | 534 | 0.197774 | −0.096 | 320 | 0.402547 | 0.064 |
| 483 | 0.124562 | 0.12 | 10 | 0.297233 | 0.086 | 614 | 0.197774 | 0.086 | 321 | 0.402547 | 0.064 |
| 484 | 0.124562 | 0.12 | 189 | 0.297233 | 0.082 | 260 | 0.205705 | 0.153 | 391 | 0.402547 | 0.094 |
| 485 | 0.124562 | 0.12 | 256 | 0.297233 | 0.106 | 391 | 0.205705 | −0.084 | 392 | 0.402547 | 0.094 |
| 486 | 0.124562 | 0.12 | 257 | 0.297233 | 0.106 | 392 | 0.205705 | −0.084 | 393 | 0.402547 | 0.094 |
| 487 | 0.124562 | 0.12 | 274 | 0.297233 | −0.091 | 393 | 0.205705 | −0.084 | 394 | 0.402547 | 0.094 |
| 488 | 0.124562 | 0.12 | 358 | 0.297233 | 0.128 | 394 | 0.205705 | −0.084 | 401 | 0.402547 | −0.112 |
| 489 | 0.124562 | 0.12 | 431 | 0.297233 | −0.178 | 306 | 0.21386 | 0.066 | 436 | 0.402547 | 0.052 |
| 490 | 0.124562 | 0.12 | 455 | 0.297233 | −0.074 | 315 | 0.21386 | 0.072 | 589 | 0.402547 | −0.081 |
| 491 | 0.124562 | 0.12 | 479 | 0.297233 | 0.089 | 203 | 0.22224 | 0.086 | 590 | 0.402547 | −0.081 |
| 492 | 0.124562 | 0.12 | 588 | 0.297233 | −0.036 | 274 | 0.22224 | 0.096 | 591 | 0.402547 | −0.081 |
| 493 | 0.124562 | 0.12 | 184 | 0.321727 | −0.122 | 298 | 0.22224 | 0.07 | 633 | 0.402547 | −0.221 |
| 494 | 0.124562 | 0.12 | 196 | 0.321727 | −0.128 | 367 | 0.22224 | 0.061 | 45 | 0.431892 | 0.081 |
| 495 | 0.124562 | 0.12 | 271 | 0.321727 | −0.082 | 390 | 0.22224 | −0.097 | 46 | 0.431892 | 0.081 |
| 496 | 0.124562 | 0.12 | 322 | 0.321727 | −0.109 | 466 | 0.22224 | −0.084 | 47 | 0.431892 | 0.081 |
| 497 | 0.124562 | 0.12 | 323 | 0.321727 | −0.109 | 533 | 0.22224 | 0.07 | 48 | 0.431892 | 0.081 |
| 498 | 0.124562 | 0.12 | 339 | 0.321727 | 0.092 | 162 | 0.230849 | 0.134 | 266 | 0.431892 | 0.137 |
| 499 | 0.124562 | 0.12 | 390 | 0.321727 | 0.142 | 176 | 0.239686 | 0.046 | 267 | 0.431892 | 0.159 |
| 500 | 0.124562 | 0.12 | 433 | 0.321727 | 0.072 | 356 | 0.239686 | −0.178 | 277 | 0.431892 | 0.078 |
| 537 | 0.124562 | 0.17 | 440 | 0.321727 | −0.085 | 551 | 0.239686 | −0.106 | 290 | 0.431892 | 0.177 |
| 589 | 0.124562 | −0.12 | 466 | 0.321727 | 0.069 | 212 | 0.248754 | −0.087 | 395 | 0.431892 | 0.041 |
| 590 | 0.124562 | −0.12 | 506 | 0.321727 | 0.085 | 358 | 0.248754 | −0.069 | 396 | 0.431892 | 0.041 |
| 591 | 0.124562 | −0.12 | 522 | 0.321727 | −0.101 | 254 | 0.258055 | 0.108 | 397 | 0.431892 | 0.041 |
| 199 | 0.130209 | 0.112 | 523 | 0.321727 | −0.101 | 267 | 0.258055 | 0.142 | 398 | 0.431892 | 0.041 |
| 341 | 0.130209 | 0.107 | 524 | 0.321727 | −0.101 | 297 | 0.258055 | −0.085 | 420 | 0.431892 | 0.108 |
| 342 | 0.130209 | 0.107 | 525 | 0.321727 | −0.101 | 433 | 0.258055 | 0.058 | 421 | 0.431892 | 0.108 |
| 382 | 0.130209 | 0.116 | 526 | 0.321727 | −0.101 | 234 | 0.267589 | 0.079 | 432 | 0.431892 | 0.103 |
| 506 | 0.130209 | 0.113 | 529 | 0.321727 | −0.098 | 345 | 0.267589 | 0.117 | 515 | 0.431892 | −0.043 |
| 517 | 0.130209 | −0.149 | 530 | 0.321727 | −0.098 | 346 | 0.267589 | 0.117 | 516 | 0.431892 | −0.043 |
| 49 | 0.136047 | 0.141 | 546 | 0.321727 | −0.089 | 532 | 0.267589 | −0.092 | 631 | 0.431892 | −0.077 |
| 195 | 0.136047 | 0.173 | 582 | 0.321727 | 0.092 | 473 | 0.277356 | −0.067 | 4 | 0.462387 | 0.052 |
| 387 | 0.136047 | −0.093 | 599 | 0.321727 | −0.06 | 474 | 0.277356 | −0.067 | 5 | 0.462387 | 0.052 |
| 388 | 0.136047 | −0.093 | 600 | 0.321727 | −0.06 | 538 | 0.277356 | 0.087 | 234 | 0.462387 | −0.071 |
| 461 | 0.136047 | 0.076 | 607 | 0.321727 | 0.139 | 539 | 0.277356 | 0.087 | 245 | 0.462387 | 0.076 |
| 188 | 0.148314 | −0.091 | 608 | 0.321727 | 0.139 | 563 | 0.277356 | −0.067 | 247 | 0.462387 | 0.042 |
| 202 | 0.148314 | −0.126 | 622 | 0.321727 | 0.153 | 564 | 0.277356 | −0.067 | 289 | 0.462387 | 0.053 |
| 603 | 0.148314 | −0.15 | 183 | 0.347446 | −0.116 | 210 | 0.287359 | 0.072 | 295 | 0.462387 | 0.035 |
| 604 | 0.148314 | −0.15 | 216 | 0.347446 | 0.241 | 251 | 0.287359 | −0.041 | 360 | 0.462387 | 0.074 |
| 605 | 0.148314 | −0.15 | 351 | 0.347446 | 0.105 | 294 | 0.287359 | 0.074 | 361 | 0.462387 | 0.074 |
| 606 | 0.148314 | −0.15 | 352 | 0.347446 | 0.105 | 429 | 0.287359 | 0.062 | 362 | 0.462387 | 0.074 |
| 167 | 0.15475 | 0.154 | 353 | 0.347446 | 0.105 | 232 | 0.297598 | −0.114 | 363 | 0.462387 | 0.074 |
| 289 | 0.16139 | 0.069 | 354 | 0.347446 | 0.105 | 261 | 0.297598 | 0.05 | 376 | 0.462387 | 0.066 |
| 1 | 0.168239 | 0.06 | 419 | 0.347446 | −0.075 | 288 | 0.297598 | 0.042 | 441 | 0.462387 | 0.08 |
| 2 | 0.168239 | 0.06 | 470 | 0.347446 | 0.056 | 154 | 0.308072 | 0.093 | 505 | 0.462387 | −0.1 |

TABLE 8-continued

Differential gene expression between the patient groups; p values for analyses 1 and 2: the markers shaded in grey are those markers exhibiting a significant difference between the groups for the respective analysis; Analysis1 (non-infectious vs. infectious cause of the multiple organ failure): CPB patients vs. septic patients with peritonitis or pneumonia focus; Analysis2 (focus of the infection, differentiation of peritonitis focus from pneumonia focus): 18 septic patients with peritonitis focus vs. 12 patients with pneumonia focus

| Analysis 1: Infectious/non-infectious | | | Analysis 2: Pneumonia/Peritonitis as the focus in septic patients | | |
|---|---|---|---|---|---|
| Seq ID | p value | Hodge-Lehmann estimator | Seq-ID | p value | Hodge-Lehmann estimator |
| 236 | 0.308072 | 0.08 | 513 | 0.462387 | −0.086 |
| 252 | 0.308072 | −0.064 | 546 | 0.462387 | −0.062 |
| 442 | 0.308072 | −0.046 | 276 | 0.494013 | 0.07 |
| 63 | 0.318782 | −0.083 | 329 | 0.494013 | 0.046 |
| 272 | 0.318782 | −0.086 | 423 | 0.494013 | 0.11 |
| 395 | 0.318782 | −0.046 | 483 | 0.494013 | 0.078 |
| 396 | 0.318782 | −0.046 | 484 | 0.494013 | 0.078 |
| 397 | 0.318782 | −0.046 | 485 | 0.494013 | 0.078 |
| 398 | 0.318782 | −0.046 | 486 | 0.494013 | 0.078 |
| 513 | 0.318782 | −0.069 | 487 | 0.494013 | 0.078 |
| 187 | 0.329728 | 0.065 | 488 | 0.494013 | 0.078 |
| 244 | 0.329728 | 0.051 | 489 | 0.494013 | 0.078 |
| 277 | 0.329728 | −0.089 | 490 | 0.494013 | 0.078 |
| 610 | 0.329728 | 0.122 | 491 | 0.494013 | 0.078 |
| 12 | 0.340909 | 0.078 | 492 | 0.494013 | 0.078 |
| 13 | 0.340909 | 0.078 | 493 | 0.494013 | 0.078 |
| 15 | 0.340909 | −0.073 | 494 | 0.494013 | 0.078 |
| 339 | 0.340909 | −0.109 | 495 | 0.494013 | 0.078 |
| 377 | 0.340909 | 0.088 | 496 | 0.494013 | 0.078 |
| 386 | 0.340909 | −0.063 | 497 | 0.494013 | 0.078 |
| 431 | 0.340909 | 0.094 | 498 | 0.494013 | 0.078 |
| 242 | 0.352326 | 0.037 | 499 | 0.494013 | 0.078 |
| 375 | 0.352326 | 0.066 | 500 | 0.494013 | 0.078 |
| 480 | 0.363976 | 0.069 | 630 | 0.494013 | 0.154 |
| 481 | 0.363976 | 0.069 | 49 | 0.526711 | −0.051 |
| 482 | 0.363976 | 0.069 | 57 | 0.526711 | 0.06 |
| 281 | 0.375859 | −0.072 | 263 | 0.526711 | 0.07 |
| 579 | 0.375859 | −0.089 | 264 | 0.526711 | 0.07 |
| 580 | 0.375859 | −0.089 | 402 | 0.526711 | −0.04 |
| 4 | 0.387973 | 0.067 | 451 | 0.526711 | 0.061 |
| 5 | 0.387973 | 0.067 | 452 | 0.526711 | 0.061 |
| 432 | 0.387973 | 0.087 | 527 | 0.526711 | 0.06 |
| 190 | 0.400318 | −0.062 | 570 | 0.526711 | 0.06 |
| 343 | 0.400318 | 0.058 | 596 | 0.526711 | 0.048 |
| 344 | 0.400318 | −0.054 | 610 | 0.526711 | −0.14 |
| 418 | 0.400318 | 0.057 | 626 | 0.526711 | −0.073 |
| 538 | 0.400318 | 0.062 | 214 | 0.56045 | −0.04 |
| 539 | 0.400318 | 0.062 | 276 | 0.56045 | 0.077 |
| 50 | 0.412891 | −0.057 | 343 | 0.56045 | −0.065 |
| 51 | 0.412891 | −0.057 | 509 | 0.56045 | 0.079 |
| 52 | 0.412891 | −0.057 | 510 | 0.56045 | 0.079 |
| 53 | 0.412891 | −0.057 | 511 | 0.56045 | 0.079 |
| 54 | 0.412891 | −0.057 | 512 | 0.56045 | 0.079 |
| 55 | 0.412891 | −0.057 | 542 | 0.56045 | 0.032 |
| 56 | 0.412891 | −0.057 | 543 | 0.56045 | 0.032 |
| 163 | 0.412891 | 0.057 | 544 | 0.56045 | 0.032 |
| 164 | 0.412891 | 0.057 | 545 | 0.56045 | 0.032 |
| 165 | 0.412891 | 0.057 | 571 | 0.56045 | 0.046 |
| 166 | 0.412891 | 0.057 | 572 | 0.56045 | 0.046 |
| 636 | 0.412891 | 0.11 | 573 | 0.56045 | 0.046 |
| 206 | 0.42569 | 0.043 | 574 | 0.56045 | 0.046 |
| 282 | 0.42569 | −0.05 | 8 | 0.595155 | −0.066 |
| 360 | 0.42569 | 0.064 | 347 | 0.595155 | 0.037 |
| 361 | 0.42569 | 0.064 | 348 | 0.595155 | 0.037 |
| 362 | 0.42569 | 0.064 | 349 | 0.595155 | 0.037 |
| 363 | 0.42569 | 0.064 | 380 | 0.595155 | 0.067 |
| 582 | 0.42569 | 0.05 | 381 | 0.595155 | 0.067 |
| 201 | 0.438713 | −0.052 | 399 | 0.595155 | 0.045 |
| 233 | 0.451957 | 0.054 | 400 | 0.595155 | 0.045 |
| 269 | 0.451957 | −0.046 | 632 | 0.595155 | −0.089 |
| 379 | 0.451957 | −0.066 | 644 | 0.595155 | 0.053 |
| 465 | 0.451957 | 0.047 | 34 | 0.630785 | −0.062 |
| 570 | 0.451957 | −0.043 | 168 | 0.630785 | 0.017 |
| 571 | 0.451957 | 0.061 | 217 | 0.630785 | 0.078 |
| 572 | 0.451957 | 0.061 | 283 | 0.630785 | 0.032 |
| 573 | 0.451957 | 0.061 | 302 | 0.630785 | −0.029 |
| 574 | 0.451957 | 0.061 | 315 | 0.630785 | −0.034 |
| 585 | 0.451957 | 0.06 | 426 | 0.630785 | 0.033 |
| 238 | 0.465419 | −0.047 | 568 | 0.630785 | 0.026 |
| 239 | 0.465419 | −0.047 | 569 | 0.630785 | 0.026 |
| 256 | 0.465419 | 0.06 | 575 | 0.630785 | −0.114 |
| 257 | 0.465419 | 0.06 | 576 | 0.630785 | −0.114 |
| 276 | 0.465419 | −0.054 | 592 | 0.630785 | 0.026 |
| 366 | 0.465419 | 0.055 | 207 | 0.667254 | 0.022 |
| 384 | 0.465419 | 0.07 | 221 | 0.667254 | −0.041 |
| 10 | 0.479097 | −0.05 | 222 | 0.667254 | −0.041 |
| 184 | 0.479097 | 0.046 | 223 | 0.667254 | −0.041 |
| 217 | 0.479097 | −0.04 | 248 | 0.667254 | 0.084 |
| 575 | 0.479097 | −0.1 | 259 | 0.667254 | 0.056 |
| 576 | 0.479097 | −0.1 | 294 | 0.667254 | 0.029 |
| 160 | 0.492987 | 0.047 | 330 | 0.667254 | 0.043 |
| 189 | 0.492987 | 0.041 | 331 | 0.667254 | 0.043 |
| 220 | 0.492987 | 0.059 | 332 | 0.667254 | 0.043 |
| 255 | 0.492987 | 0.056 | 333 | 0.667254 | 0.043 |
| 413 | 0.492987 | −0.058 | 334 | 0.667254 | 0.043 |
| 414 | 0.492987 | −0.058 | 335 | 0.667254 | 0.043 |
| 415 | 0.492987 | −0.058 | 403 | 0.667254 | 0.044 |
| 416 | 0.492987 | −0.058 | 469 | 0.667254 | −0.037 |
| 625 | 0.492987 | 0.055 | 531 | 0.667254 | −0.046 |
| 550 | 0.507086 | −0.071 | 60 | 0.704507 | 0.033 |
| 551 | 0.507086 | −0.071 | 185 | 0.704507 | −0.019 |
| 557 | 0.507086 | 0.035 | 203 | 0.704507 | −0.074 |
| 558 | 0.507086 | 0.035 | 287 | 0.704507 | 0.051 |
| 559 | 0.507086 | 0.035 | 377 | 0.704507 | −0.073 |
| 560 | 0.507086 | 0.035 | 387 | 0.704507 | 0.086 |
| 643 | 0.507086 | 0.043 | 388 | 0.704507 | 0.086 |
| 17 | 0.521389 | 0.048 | 472 | 0.704507 | −0.031 |
| 198 | 0.535892 | 0.044 | 520 | 0.704507 | −0.014 |
| 533 | 0.535892 | −0.037 | 521 | 0.704507 | −0.014 |
| 637 | 0.535892 | 0.029 | 533 | 0.704507 | −0.033 |
| 638 | 0.535892 | 0.029 | 547 | 0.704507 | 0.039 |
| 639 | 0.535892 | 0.029 | 186 | 0.742446 | −0.02 |
| 640 | 0.535892 | 0.029 | 279 | 0.742446 | 0.018 |
| 641 | 0.535892 | 0.029 | 293 | 0.742446 | 0.084 |
| 642 | 0.535892 | 0.029 | 301 | 0.742446 | −0.027 |
| 34 | 0.550592 | 0.054 | 357 | 0.742446 | −0.029 |
| 317 | 0.550592 | −0.023 | 427 | 0.742446 | 0.032 |
| 318 | 0.550592 | −0.023 | 428 | 0.742446 | 0.032 |
| 648 | 0.550592 | −0.05 | 575 | 0.742446 | −0.037 |
| 649 | 0.550592 | −0.05 | 576 | 0.742446 | −0.037 |
| 284 | 0.565483 | −0.033 | 648 | 0.742446 | −0.072 |
| 293 | 0.565483 | −0.053 | 649 | 0.742446 | −0.072 |
| 554 | 0.565483 | −0.023 | 42 | 0.78101 | −0.022 |
| 60 | 0.580562 | −0.059 | 155 | 0.78101 | 0.022 |
| 478 | 0.595822 | 0.042 | 275 | 0.78101 | 0.025 |
| 507 | 0.595822 | 0.03 | 306 | 0.78101 | −0.023 |
| 508 | 0.595822 | 0.03 | 350 | 0.78101 | 0.031 |
| 205 | 0.611259 | −0.052 | 378 | 0.78101 | 0.039 |
| 355 | 0.611259 | −0.093 | 386 | 0.78101 | 0.036 |
| 378 | 0.611259 | −0.029 | 408 | 0.78101 | 0.019 |
| 8 | 0.626866 | 0.027 | 409 | 0.78101 | 0.019 |
| 303 | 0.626866 | 0.036 | 410 | 0.78101 | 0.019 |
| 316 | 0.626866 | −0.019 | 411 | 0.78101 | 0.019 |
| 562 | 0.626866 | 0.031 | 412 | 0.78101 | 0.019 |

TABLE 8-continued

Differential gene expression between the patient groups; p values for analyses 1 and 2: the markers shaded in grey are those markers exhibiting a significant difference between the groups for the respective analysis; Analysis1 (non-infectious vs. infectious cause of the multiple organ failure): CPB patients vs. septic patients with peritonitis or pneumonia focus; Analysis2 (focus of the infection, differentiation of peritonitis focus from pneumonia focus): 18 septic patients with peritonitis focus vs. 12 patients with pneumonia focus

| | Analysis 1: Infectious/non-infectious | | | Analysis 2: Pneumonia/Peritonitis as the focus in septic patients | |
|---|---|---|---|---|---|
| Seq ID | p value | Hodge-Lehmann estimator | Seq-ID | p value | Hodge-Lehmann estimator |
| 9 | 0.658572 | −0.048 | 542 | 0.78101 | −0.047 |
| 18 | 0.674658 | −0.025 | 543 | 0.78101 | −0.047 |
| 216 | 0.674658 | −0.055 | 544 | 0.78101 | −0.047 |
| 347 | 0.674658 | 0.019 | 545 | 0.78101 | −0.047 |
| 348 | 0.674658 | 0.019 | 650 | 0.78101 | 0.029 |
| 349 | 0.674658 | 0.019 | 188 | 0.82009 | 0.04 |
| 468 | 0.674658 | 0.022 | 260 | 0.82009 | −0.012 |
| 536 | 0.674658 | −0.036 | 299 | 0.82009 | −0.043 |
| 11 | 0.690891 | 0.039 | 300 | 0.82009 | −0.043 |
| 434 | 0.690891 | −0.053 | 307 | 0.82009 | −0.027 |
| 435 | 0.690891 | −0.053 | 308 | 0.82009 | −0.027 |
| 565 | 0.690891 | −0.033 | 309 | 0.82009 | −0.027 |
| 172 | 0.707264 | 0.025 | 310 | 0.82009 | −0.027 |
| 173 | 0.707264 | 0.025 | 311 | 0.82009 | −0.027 |
| 174 | 0.707264 | 0.025 | 344 | 0.82009 | 0.028 |
| 224 | 0.707264 | 0.024 | 418 | 0.82009 | 0.026 |
| 246 | 0.707264 | 0.037 | 548 | 0.82009 | −0.027 |
| 271 | 0.723771 | −0.021 | 549 | 0.82009 | 0.018 |
| 171 | 0.740405 | −0.018 | 554 | 0.82009 | 0.011 |
| 567 | 0.740405 | −0.022 | 598 | 0.82009 | 0.031 |
| 586 | 0.757158 | −0.019 | 11 | 0.859616 | −0.011 |
| 419 | 0.774024 | −0.017 | 16 | 0.859616 | −0.025 |
| 66 | 0.790995 | −0.012 | 246 | 0.859616 | 0.044 |
| 447 | 0.790995 | 0.021 | 340 | 0.859616 | 0.027 |
| 448 | 0.790995 | 0.021 | 480 | 0.859616 | −0.018 |
| 449 | 0.790995 | 0.021 | 481 | 0.859616 | −0.018 |
| 450 | 0.790995 | 0.021 | 482 | 0.859616 | −0.018 |
| 514 | 0.790995 | −0.014 | 547 | 0.859616 | −0.009 |
| 548 | 0.790995 | 0.021 | 603 | 0.859616 | 0.025 |
| 268 | 0.808064 | −0.017 | 604 | 0.859616 | 0.025 |
| 16 | 0.825223 | 0.018 | 605 | 0.859616 | 0.025 |
| 209 | 0.825223 | −0.018 | 606 | 0.859616 | 0.025 |
| 241 | 0.825223 | −0.016 | 627 | 0.859616 | 0.012 |
| 437 | 0.825223 | 0.017 | 643 | 0.859616 | 0.013 |
| 502 | 0.825223 | −0.016 | 154 | 0.899475 | −0.033 |
| 503 | 0.825223 | −0.016 | 169 | 0.899475 | −0.022 |
| 266 | 0.842464 | 0.032 | 179 | 0.899475 | 0.002 |
| 374 | 0.859779 | −0.008 | 180 | 0.899475 | 0.002 |
| 644 | 0.859779 | 0.02 | 195 | 0.899475 | 0.033 |
| 185 | 0.877161 | −0.013 | 561 | 0.899475 | 0.014 |
| 417 | 0.877161 | 0.01 | 614 | 0.899475 | −0.012 |
| 583 | 0.877161 | −0.007 | 634 | 0.899475 | 0.032 |
| 584 | 0.877161 | −0.007 | 63 | 0.93959 | −0.007 |
| 279 | 0.8946 | −0.013 | 190 | 0.93959 | −0.022 |
| 287 | 0.91209 | −0.011 | 206 | 0.93959 | 0.011 |
| 336 | 0.91209 | −0.01 | 212 | 0.93959 | 0.028 |
| 155 | 0.929622 | −0.024 | 417 | 0.93959 | −0.006 |
| 169 | 0.929622 | −0.013 | 536 | 0.93959 | 0.037 |
| 178 | 0.929622 | 0.006 | 597 | 0.93959 | 0.009 |
| 181 | 0.929622 | 0.009 | 160 | 0.979843 | 0.006 |
| 368 | 0.929622 | −0.024 | 172 | 0.979843 | 0.002 |
| 369 | 0.929622 | −0.024 | 173 | 0.979843 | 0.002 |
| 370 | 0.929622 | −0.024 | 174 | 0.979843 | 0.002 |
| 371 | 0.929622 | −0.024 | 241 | 0.979843 | 0.017 |
| 372 | 0.929622 | −0.024 | 273 | 0.979843 | 0.005 |
| 373 | 0.929622 | −0.024 | 477 | 0.979843 | 0.003 |
| 58 | 0.964777 | 0.007 | 537 | 0.979843 | 0.01 |
| 59 | 0.964777 | 0.007 | 557 | 0.979843 | −0.001 |
| 359 | 0.964777 | 0.005 | 558 | 0.979843 | −0.001 |
| 534 | 0.964777 | −0.003 | 559 | 0.979843 | −0.001 |
| 18 | 0.982384 | −0.002 | 560 | 0.979843 | −0.001 |
| 477 | 0.982384 | 0.003 | 611 | 0.979843 | −0.011 |
| 285 | 1 | −0.002 | 612 | 0.979843 | −0.011 |
| 455 | 1 | 0.002 | 623 | 0.979843 | 0.003 |
| 575 | 1 | 0.001 | 269 | 1 | 0 |
| 576 | 1 | 0.001 | 553 | 1 | −0.005 |

Example 2

Establishing a Classifier for the Identification of SIRS and Sepsis Patients by Means of Real-Time PCR Measuring the Gene Expression Patients with pneumonia and peritonitis, respectively, were selected as typical sepsis representatives, and in the case of SIRS patients with severe heart surgery (cardiopulmonal bypass, CPB), for these make up the majority of SIRS patients in an ICU (see Table 9). The patients were retrospectively validated in their diagnosis by a team of medical doctors of Jena university hospital.

Total RNA was isolated from the patients' blood and transcribed to cDNA. The latter was used in the assay as a template.

TABLE 9

List of examined patients

| | Sepsis | | |
|---|---|---|---|
| Patient ID | Peritonitis | Pneumonia | SIRS |
| 714 | X | | |
| 6008 | X | | |
| 6009 | X | | |
| 6025 | X | | |
| 6035 | X | | |
| 6040 | X | | |
| 6046 | X | | |
| 6062 | X | | |
| 6065 | X | | |
| 6073 | X | | |
| 6075 | X | | |
| 6084 | X | | |
| 6032 | | X | |
| 6048 | | X | |
| 6063 | | X | |
| 6070 | | X | |
| 6085 | | X | |
| 6104 | | X | |
| 6141 | | X | |
| 814 | | | X |
| 8001 | | | X |
| 8002 | | | X |
| 8009 | | | X |
| 8010 | | | X |

TABLE 9-continued

List of examined patients

| Patient ID | Sepsis | | | SIRS |
| --- | --- | --- | --- | --- |
| | Peritonitis | Pneumonia | | |
| 8012 | | | | X |
| 8068 | | | | X |
| 8096 | | | | X |
| 8102 | | | | X |
| 8111 | | | | X |
| 8112 | | | | X |
| 8116 | | | | X |

The markers for classification (Table 10) were selected from the biomarker pool (see Example 1) and show strong differential gene expression in patient groups with and without diagnosed sepsis.

For the quantification of gene expression, various methods are available. Relative quantification of gene expression amounts to a statement concerning abundance of the target transcript in relation, e.g., to a calibrator. The latter may be a reference value determined from the expression values of genes which are expressed in a constant manner (so-called reference genes or housekeeping genes). Such reference genes are specific for each organism and each tissue and must be selected carefully for the respective study. Starting out from the gene expression profiles from the full blood of the sepsis and control patients, the most stable genes having the least variability were selected and used in the quantitative PCR for normalization.

TABLE 10

Marker genes used for the classification

| Marker | Description (NCBI database, http://www.ncbi.nlm.nih.gov/) |
| --- | --- |
| BZRP | Benzodiazepine receptor |
| CD82 | CD82 molecule |
| CD59 | CD59 molecule |
| FGL2 | Fibrinogen-related protein |
| HLA-DPA1 | Major histocompatibility complex, class II, DP alpha 1 |
| CPVL | Carboxypeptidase vitellogenetic-like gene |
| MME | Metallomembrane endopeptidase |
| IL7R | Interleukin 7 receptor |
| CCR2 | Chemokine (C-C motif) receptor 2 |
| EPC1 | Enhancer of polycomb homolog 1 (primer pair 6) |
| KIAA0146 | |
| C4orf18 | Chromosome 4 open reading frame 18 |
| MON2 | =KIAA1040, MON2 homolog |
| NSMAF | Neutral sphingomyelinase (N-SMase) activation associated factor |
| TLR5 | Toll-like receptor 5 |
| CLU | Clusterin |
| IGKCem | Immunglobulin kappa constant |
| ZFANDA | Zinc finger AN-type domain 2A |
| UBC (housekeeper) | Ubiquitin |
| ITGAL (housekeeper) | Integrin, alpha L |
| SNAPC (housekeeper) | Small nuclear RNA activating complex |
| IL18 (housekeeper) | Interleukin 18 |
| CASP8 (housekeeper) | Caspase 8 |

Table 11 is a list of the primers used in real-time PCR and their SeqIDs. Several primer combinations are possible for each target sequence, with the table representing only one of many possibilities.

TABLE 11

List of primers used. Several primer combinations are possible for each target sequence.

| Markers and reference genes | Primers for quantitative PCR (SeqID) | |
| --- | --- | --- |
| BZRP | Forward | 687 |
| (SeqID 601, 602) | Reverse | 688 |
| CD82 | Forward | 689 |
| (SeqID 470, 471) | Reverse | 690 |
| CD59 | Forward | 691 |
| (SeqID 571, 572, 573, 574) | Reverse | 692 |
| FGL2 | Forward | 693 |
| (SeqID 615) | Reverse | 694 |
| HLA-DPA1 | Forward | 695 |
| (SeqID 613) | Reverse | 696 |
| CPVL | Forward | 697 |
| (SeqID 619, 620) | Reverse | 698 |
| MME | Forward | 699 |
| (SeqID 443, 444, 445, 446) | Reverse | 700 |
| IL7R | Forward | 701 |
| (SeqID 541) | Reverse | 702 |
| CCR2 | Forward | 703 |
| (SeqID 529, 530) | Reverse | 704 |
| EPC1 | Forward | 705 |
| (SeqID 280) | Reverse | 706 |
| KIAA0146 | Forward | 707 |
| (SeqID 261) | Reverse | 708 |
| C4orf18 | Forward | 709 |
| (SeqID 611, 612) | Reverse | 710 |
| MON2 | Forward | 711 |
| (SeqID 248) | Reverse | 712 |
| NSMAF | Forward | 713 |
| (SeqID 527) | Reverse | 714 |
| TLR5 | Forward | 715 |
| (SeqID 431) | Reverse | 716 |
| CLU | Forward | 717 |
| (SeqID 575, 576) | Reverse | 718 |
| IGKCem | Forward | 719 |
| (SeqID 401) | Reverse | 720 |
| ZFANDA | Forward | 721 |
| (SeqID 290) | Reverse | 722 |
| UBC | Forward | 723 |
| (SeqID 678) | Reverse | 724 |
| ITGAL | Forward | 725 |
| (SeqID 676, 677) | Reverse | 726 |
| SNAPC | Forward | 727 |
| (SeqID 679) | Reverse | 728 |
| IL18 | Forward | 729 |
| (SeqID 680) | Reverse | 730 |
| CASP8 | Forward | 731 |
| (SeqID 681, 682, 683, 684, 685, 686) | Reverse | 732 |

Experimental Execution

Blood Sampling and RNA Isolation:

The patient's full blood was taken from the patients at the intensive care unit by means of the PAXGene kit in accordance with the manufacturer's specifications (Qiagen), and the RNA was isolated.

Reverse Transcription:

From each patient sample, 4 µg of the total RNA was transcribed to complementary DNA (cDNA) with the reverse transcriptase Superscript II (Invitrogen) in a 20-µl batch (contains 1 µl of 10 mM dNTP-mix of Fermentas and 1 µl of 0.5 µg/µl Oligo(dT) primer). The RNA was subsequently removed from the batch by alkaline hydrolysis. The reaction batches were not purified but filled to 50 µl with water.

Real-Time PCR

The Platinum SYBR Green gPCR SuperMix-UDG kit by the company Invitrogen was used. The patient cDNA was diluted 1:100 with water, and 1 µl each thereof was utilized in the PCR. For each marker a PCR plate (BIORAD) with all 31 patient and no-template controls (NTC) was pipetted in triplicate.

PCR batch pro well (10 µl) 2 µl of template cDNA 1:100

1 µl of forward primer, 10 mM

1 µl of reverse primer, 10 mM

1 µl of Fluorescein Reference Dye

5 µl of Platinum SYBR Green qPCR SuperMix-UDG

A mastermix without template was prepared and was stepped in 9 µl-aliquots into the PCR plate, to each of which the patient cDNAs were pipetted.

The subsequent PCR program was constructed as follows:

| | | |
|---|---|---|
| 95° C. | 2 min (activation of the polymerase) | |
| 95° C. | 10 sec (denaturing) | |
| 58° C. | 15 sec (addition) | 40 x |
| 72° C. | 20 sec (extension) | |
| 55° C.-95° C. | 10 sec (drawing up the melting curve, increasing the initial temperatur by 1° C. after each step) | 41 x |

Figure 9:
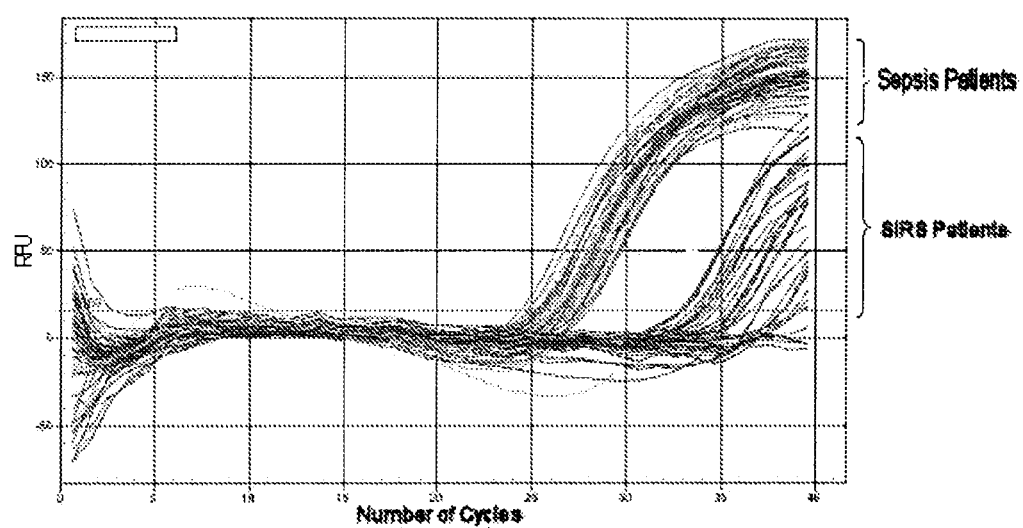
FIG. 9 shows an example of a qPCR run (Marker EPC1)

The iQ™5 Multicolor Real-Rime PCR Detection System by the company BIORAD with the associated evaluation software was used. The results of such a gPCR run are shown in FIG. 9. The evaluation software was used to generate representations for each one of the 18 markers and 5 housekeepers, from which the corresponding Ct values could then be derived. The Ct values are calculated automatically by the program in the area of linear ascent of the curves. In the example of EPC1, the Ct values were in the range of 25.08-27.71 for the sepsis patients and in the range of 28.08-35.91 for the SIRS patients.

Data Analysis:

Data analysis was performed under the free software R Project Version 2.6.1 which is available under www.r-project.org.

Data-Pre-Processing:

The measured expression signals were stored in the Excel format and averaged via the 3-time determinations. The marker MON2 with 15 missing values and patients 6065 and 8111 with 13 and one missing value, respectively, were excluded from analysis. Thus, the training data set contained 18 infectious (62%) and 11 non-infectious (38%) samples. For normalization, the 3 most stable housekeeper genes were determined from among the 5 measured ones. Subsequently the mean value of the 3 selected housekeeper genes was subtracted from the marker genes for each patient.

Classification:

In order to arrange the gene markers in accordance with their quality of separation, the Wilcoxon rank-sum test was carried out in which the patient groups with and without an infectious complication were compared. After this, genes with p <0.001 were arranged in accordance with the Hodge-Lehmann estimator, and the remaining ones in accordance with the p value proper.

For classification, the linear discriminant analysis [Hastie et al., 2001] with a simple cross-validation was used. Calculation was carried out by using the function lda from the R library MASS. For p markers, the weights $(w_0, \ldots, w_p)$ of the discriminant function $f_{LD}$, which is defined by the formula $$f_{LD}(x_1, \ldots, x_p) = \sum_{i=1}^{p} w_i x_i - w_0$$

were calculated from the training data by successively omitting one sample each. This sample was classified later on, with the Ct values of the sample being inserted in the above formula for $x_i$. The weights of the discriminant function were calculated such that a positive value of the function means the assignment to the group with an infectious complication, and a negative value of the function means the assignment to the group without an infectious complication. The classification procedure was repeated for an ascending number of markers.

Then the manner of proceeding for all training data was performed, and two additional independent samples were classified. The weights of the linear discriminant function for the ascending number of the markers and the associated score values for independent samples 790 and 933 (the values shaded in grey were represented graphically in FIG. 12) are summarized in Table 12.

Results

In classification, at first the best 2 markers were used, after which the next marker was added stepwise. In simple cross-validation, there was no false classification of samples in nearly all of the cases. Merely with the use of 13, 14 and 17 markers, one non-infectious sample was classified falsely in simple cross-validation. Thus, a sensitivity of 100% and a specificity of 91% for the training data set were achieved.

Figure 10:
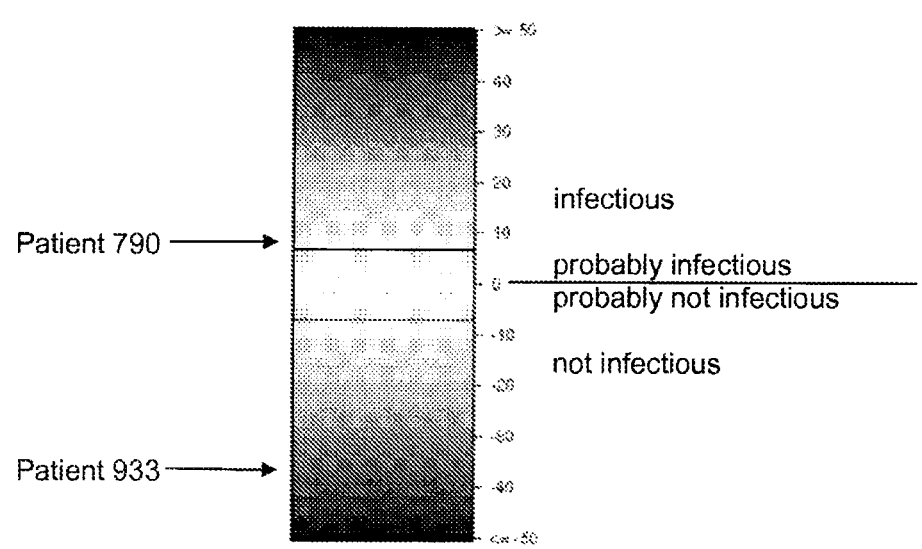
FIG. 10 is a schematic representation of the derived score value for 12 markers and the classification into four areas; the classification result is projected onto this scale.

Both of the independent samples 933 and 790 were predominantly classified correctly. 2 and more markers were required for the correct classification (i.e., a negative score value) of the non-infectious sample 933. 6 and more markers were required for the infectious sample 790 in order to obtain a positive score value (cf. Table 12). The classification became instable with more than 14 markers. In FIG. 10 the score values for the classification with 12 markers for the samples 933 and 790 are depicted. This is a schematic representation of the derived score value and the classification into 4 areas. If the calculated score is higher than 6.5, there is a 95-% probability of the patient having a sepsis (infectious). If the score is less than −6.5, the probability of the patient not having sepsis is equally 95% (non-infectious). Onto this scale the classification result for 12 markers was projected for two test samples that were independent of the classification data set. The score of sample 933 assumed the value of −36.58 and the patient was classified as non-infectious; the score of sample 790 assumed the value of 7.44 and was classified as infectious.

The experiments yielded expression signals of good quality, so that the associated data matrix could be used for establishing the classifier. By means of the measured signals the training data could be separated virtually completely in accordance with the infectious complication. Likewise, 2 independent test data items were classified correctly. For a robust quality of classification in the training and test data sets, 6 to 14 classification markers were required.

Table 13a shows the raw data (Ct values) from the qPCR assays, with Table 13b showing the weights of the linear discriminant function for an ascending number of markers and the associated score values for independent samples 790 and 933.

TABLE 12

Weights of the linear discriminant function for an ascending number of markers and the associated score values for independent samples 790 and 933.

| | Seq ID | p = 2 | p = 3 | p = 4 | p = 5 | p = 6 | p = 7 | p = 8 | p = 9 | p = 1 | p = 11 | p = 12 | p = 13 | p = 14 | p = 15 | p = 16 | p = 17 | p = 18 |
|---|---|---|---|---|---|---|---|---|---|---|---|---|---|---|---|---|---|---|
| W0 | | -39.36 | -53.34 | -68.95 | -58.44 | -55.59 | -55.87 | -59.29 | -76.46 | -75.13 | -42.95 | -43.29 | -43.14 | 11.70 | 8.42 | 13.12 | 13.93 | 184.99 |
| w1 | 602, 603 | 1.30 | 1.34 | 12.60 | 12.92 | 14.37 | 14.45 | 14.73 | 16.40 | 16.35 | 21.18 | 21.57 | 21.59 | 21.55 | 26.94 | 27.62 | 27.99 | 35.77 |
| w2 | 281 | -6.48 | -4.63 | -3.26 | -6.17 | -6.29 | -6.24 | -6.56 | -7.55 | -7.57 | -5.27 | -5.12 | -5.93 | -4.17 | -7.43 | -8.53 | -8.37 | -9.17 |
| w3 | 614 | | 4.52 | 3.87 | 1.63 | 1.68 | 1.61 | 2.70 | 1.25 | 1.15 | -1.13 | -1.98 | -0.98 | -3.65 | -3.96 | -3.71 | -3.25 | -2.75 |
| w4 | 444, 445, 446, 447 | | | 4.16 | 1.76 | 2.43 | 1.99 | 1.83 | 0.99 | 0.99 | 0.45 | 0.45 | 0.44 | -0.45 | -0.95 | -2.00 | -1.50 | 1.47 |
| w5 | 530, 531 | | | | 7.32 | 8.32 | 7.78 | 7.42 | 5.14 | 5.14 | 6.64 | 6.50 | 6.50 | 9.19 | 11.48 | 11.82 | 11.54 | 27.74 |
| w6 | 616 | | | | | -2.98 | -3.21 | -2.99 | -4.63 | -4.58 | -8.25 | -7.73 | -7.72 | -7.58 | -12.73 | -1.45 | -11.38 | -24.85 |
| w7 | 620, 621 | | | | | | 0.43 | 1.85 | 1.71 | 1.74 | -0.39 | -0.32 | -0.32 | -1.34 | -0.14 | 0.14 | 0.42 | -1.15 |
| w8 | 612, 613 | | | | | | | | -2.27 | -2.35 | -2.32 | -0.82 | -0.80 | -0.89 | 1.62 | 1.59 | 0.17 | 0.34 | 2.25 |
| w9 | 616 | | | | | | | | | 8.72 | 8.69 | 1.26 | 9.57 | 9.53 | 8.60 | 1.15 | 8.57 | 9.24 | 18.49 |
| w10 | 262 | | | | | | | | | | 0.23 | 2.62 | 275 | 277 | 7.35 | 7.65 | 9.65 | 8.79 | 8.23 |
| w11 | 572, 573, 574, 575 | | | | | | | | | | | -1.34 | -1.47 | -1.87 | -12.25 | -12.33 | -13.73 | -13.90 | -9.81 |
| w12 | 471, 472 | | | | | | | | | | | | -0.93 | -0.98 | 0.84 | 2.64 | 1.13 | 1.66 | 1.75 |
| w13 | 542 | | | | | | | | | | | | | -0.61 | 0.69 | -3.23 | -5.22 | -5.15 | -4.66 |
| w14 | 634 | | | | | | | | | | | | | | -4.54 | -5.85 | -5.98 | -5.78 | -9.98 |
| w15 | 432 | | | | | | | | | | | | | | | -17.86 | -18.92 | -18.47 | -22.29 |
| w16 | 291 | | | | | | | | | | | | | | | | 6.24 | 5.84 | 6.88 |
| w17 | 571 | | | | | | | | | | | | | | | | | -1.55 | -12.59 |
| w18 | 528 | | | | | | | | | | | | | | | | | | -31.82 |
| Score 933 | | -37.19 | -44.48 | -62.66 | -27.35 | -17.11 | -18.71 | -22.67 | -31.91 | -32.63 | -37.76 | -36.58 | -36.42 | -28.27 | 2.74 | -1.45 | -3.85 | 98.95 |
| Score 790 | | -3.26 | -22.34 | -2.62 | -0.66 | 9.60 | 8.68 | 9.34 | 3.86 | 3.93 | 6.12 | 7.44 | 7.49 | 12.96 | -11.45 | -14.86 | -17.38 | 7.68 |

TABLE 13a

Raw data (Ct values) from the qPCR assays

| Pat. ID | CPVLL | CLU | FGL2 | NSMAFFF | TLR5 | CCR22 | HLADPA1A | ILR7 | ZFANDAA | CD599 | C4orf1888 | KIAA014646 |
|---|---|---|---|---|---|---|---|---|---|---|---|---|
| 714 | 27.28 | 24.51 | 25.79 | 25.62 | NA | 27.69 | 26.87 | 28.91 | 29.27 | 24.18 | 28.55 | 33.04 |
| 6008 | 30.04 | 24.48 | 28.95 | 28.49 | 26 | 30.57 | 27.48 | 28.29 | 30.88 | 25.42 | 29.24 | 34.06 |
| 6009 | 28.85 | 24.01 | 25.96 | 26.26 | 23.72 | 29.25 | 28.83 | 24.93 | 30.86 | 24.2 | 28.27 | 31.85 |
| 6025 | 29.96 | 23.87 | 27.92 | 27.92 | NA | 30.35 | 27.71 | 27.91 | 29.64 | 24.78 | 29.1 | 34.67 |
| 6032 | 28.33 | 23.22 | 26.51 | 27.02 | 25.39 | 29.11 | 25.71 | 24.92 | 29.59 | 25.83 | 27.58 | NA |
| 6035 | 27.42 | 25.11 | 25.8 | 27.28 | 24.43 | 28.84 | 27.94 | 28.16 | 29.3 | 24.95 | 28.12 | 33.19 |
| 6040 | 29.72 | 23.73 | 25.89 | 26.72 | 24.44 | 30.37 | 26.51 | 26.47 | 28.44 | 24.65 | 27.85 | 33.34 |
| 6046 | 28.75 | 24.01 | 27.74 | 26.78 | 24.56 | 29.47 | 25.39 | 25.62 | 28.41 | 25.63 | 27.81 | 31.87 |
| 6048 | 29.32 | 25.65 | 26.53 | 26.48 | 25.07 | 29.23 | 27.04 | 28.02 | 30.99 | 26.33 | 28.76 | 35.28 |
| 6062 | 30.15 | 23.88 | 26.83 | 27.14 | 23.93 | 30.74 | 26.87 | 26.95 | 29.38 | 24.83 | 28.9 | 33.93 |
| 6063 | 26.91 | 24.61 | 21.67 | 25.64 | 23.94 | 26.93 | 24.4 | 25.44 | 29.25 | 24.84 | 26.91 | 32.72 |
| 6065 | NA | NA | NA | 31.72 | NA | NA | NA | 32.83 | NA | NA | NA | NA |
| 6070 | 27.13 | 24.01 | 25.82 | 27.02 | 23.59 | 28.63 | 26.46 | 26.9 | 29.42 | 25.14 | 27.17 | 32.64 |
| 6073 | 28.79 | 24.4 | 27.62 | 25.85 | 23.68 | 30.13 | 27.12 | 27.96 | 29 | 24.16 | 27.98 | 33.53 |
| 6075 | 34.37 | 23.89 | 28.52 | 25.96 | 24.69 | 32.32 | 28.75 | 29.62 | 30.1 | 24.36 | 32.24 | 34.65 |
| 6084 | 27.05 | 23.95 | 25.23 | 27.13 | 23.99 | 28.33 | 26.61 | 26.63 | 29.15 | 23.79 | 27.36 | NA |
| 6085 | 29.05 | 24.05 | 27.51 | NA | 24.67 | 30.65 | 27.12 | 26.1 | 29.75 | 27.66 | 27.88 | 35.95 |
| 6104 | 27.24 | 23.9 | 25.92 | 27.48 | 24.44 | 29.04 | 27.23 | 25.03 | 28.38 | 25.65 | 28.05 | 32.2 |
| 6141 | 29.26 | 25.39 | 26.55 | 27.06 | 23.81 | 31.03 | 26.79 | 27.87 | 30.44 | 26.46 | 27.38 | NA |
| 8001 | 26.87 | 25.59 | 24.92 | 26.76 | 25.87 | 26.02 | 23.4 | 22.64 | 31.16 | 27.34 | 26.97 | 32.69 |
| 8002 | 27.03 | 23.82 | 25.85 | 28.33 | 24.49 | NA | 24.07 | 25.75 | 29.62 | 26.35 | NA | 32.89 |
| 8009 | 27.35 | 24.54 | 23.75 | 26.22 | 26.09 | 25.55 | 23.34 | 25.51 | 29.16 | 27.47 | 26.93 | 31.88 |
| 8010 | 26.57 | 25.66 | 24.89 | 26.58 | 24.55 | 26.65 | 23.82 | 25.23 | 29.54 | 25.88 | 26.29 | 31.8 |
| 8012 | 27.42 | 25.92 | 26.19 | 27.76 | 25.38 | NA | 24.27 | 25.71 | 29.05 | 27.56 | 26.66 | 32.3 |
| 8068 | 27.38 | 24.39 | 25.25 | 26.88 | 25.46 | 27.04 | 27.82 | 25.46 | 29.39 | 26.17 | 26.92 | 31.83 |
| 8096 | 27.83 | 24.69 | 25.61 | 27.28 | 25.94 | 26.96 | 24.54 | 26.04 | 29.63 | 25.38 | 25.75 | 32.49 |
| 8102 | 26.32 | 23.96 | 25.65 | 29.37 | 26.62 | 27.24 | 24.62 | 26.55 | 30.83 | 27.43 | 26.72 | 32.58 |
| 8111 | 31.4 | 25.9 | 30.99 | 32.89 | 31.78 | 33.33 | 33.26 | 30.33 | 35.13 | 33.75 | 34.97 | NA |
| 8112 | 26.97 | NA | 25.38 | 26.55 | 24.77 | 26.19 | NA | 25.05 | NA | 26.44 | 27.55 | 31.04 |
| 8116 | 26.45 | 23.91 | 27.13 | 28.71 | 25.98 | 29.82 | 24.13 | 27.04 | 31.09 | 28.53 | 27.08 | 32.73 |
| 814 | 26.43 | 25.27 | 24.9 | 26.25 | 26.56 | 25.87 | 23.58 | NA | 29.1 | 26.23 | NA | 30.18 |

| Pat. ID | EPC16 | MMEE | MON22 | IGKCm | CD822 | FGL2lt | BZRP | UBC | SNAPCC | IL18 | ITGALL | CASP88 |
|---|---|---|---|---|---|---|---|---|---|---|---|---|
| 714 | 25.08 | 24.93 | NA | 22.23 | 27.78 | 26.33 | 27.56 | 19.75 | 33.39 | 28.8 | NA | NA |
| 6008 | 27.65 | 26.39 | 37.45 | 24.36 | 27.62 | 26.73 | 26.67 | 21.68 | 35.6 | NA | 27.06 | 27.14 |
| 6009 | 25.54 | 26.52 | NA | 21.94 | 27.74 | 26.08 | 26.82 | 20.77 | 32.15 | 29.39 | 25.83 | 25.6 |
| 6025 | 26.65 | 30.32 | 32.15 | 20.83 | 26.88 | 27.68 | 26.07 | 20.92 | 33.95 | 28.39 | 27.59 | 27.23 |
| 6032 | 27.08 | 25.66 | 31.56 | 20.34 | 27.28 | 25.46 | 26.52 | 21.6 | 33.57 | 29.77 | 25.9 | 26.66 |

TABLE 13a-continued

Raw data (Ct values) from the qPCR assays

| 6035 | 26.09 | 27.55 | 31.7  | 21.24 | 26.83 | 26.26 | 25 91 | 21.31 | 33.54 | 28.52 | 25.77 | 26.96 |
| 6040 | 25.87 | 29.55 | NA    | 23.79 | 26.85 | 25.02 | 25.8  | 18.77 | 31.3  | 27.08 | 25.56 | 25.89 |
| 6046 | 25.68 | 29.93 | 31.51 | 19.57 | 26.68 | 27.26 | 26.76 | 20.64 | 31.94 | NA    | 26.17 | 26.14 |
| 6048 | 26.68 | 28.89 | NA    | 22.62 | 27.9  | 27.02 | 26.46 | 19.96 | 32.04 | 28.64 | 28.2  | 26.81 |
| 6062 | 26.3  | 30.42 | NA    | 22.67 | 26.53 | 26.27 | 26.55 | 21.91 | 32.89 | 30.72 | 26.07 | 26.47 |
| 6063 | 24.8  | 24.77 | 30.75 | 20.87 | 27.24 | 23.93 | 26.26 | 20.04 | 30.85 | 28.83 | 24.86 | 25.83 |
| 6065 | NA    | NA    | NA    | NA    | 34.54 | NA    | 33.47 | NA    | NA    | NA    | 36.48 | NA    |
| 6070 | 26.06 | 27.03 | 31.83 | 21.6  | 27.92 | 25.67 | 27.78 | 20.78 | 32.91 | 29.73 | 25.54 | 26.89 |
| 6073 | 26.68 | 28.51 | 31.98 | NA    | 26.89 | 27.32 | 25.17 | 19.75 | 31.56 | 25.85 | 26.35 | 26.25 |
| 6075 | 27.31 | 29.52 | NA    | 24.55 | 26.89 | 28.76 | 27.29 | 20.26 | 33.22 | 30.21 | 27.92 | 27.06 |
| 6084 | 26.31 | 26.29 | 32.23 | 20.11 | 27.14 | 24.96 | 27.78 | 20.56 | 32.08 | 30.03 | 24.7  | 26.09 |
| 6085 | NA    | 28.76 | NA    | 24.49 | 27.82 | 26.34 | 28.2  | 22.17 | 32.46 | 31.17 | NA    | 27.03 |
| 6104 | 26.63 | 24.74 | 31.72 | 21.91 | 27.31 | 25.84 | 27.24 | 19.85 | 31.79 | 30.39 | 25.7  | 26.35 |
| 6141 | 27.71 | 24.88 | NA    | 21.63 | 29.76 | 27.15 | 28.1  | 20.78 | 33.36 | 30.94 | NA    | 25.17 |
| 8001 | 28.69 | 24.94 | NA    | 22.35 | 26.1  | 22.81 | 22.19 | 20.11 | 32.68 | 31.15 | 25.88 | 27.24 |
| 8002 | 30.11 | 25.3  | NA    | 21.71 | 25.56 | 24.03 | 22.03 | 21.59 | NA    | 29.68 | 25.62 | 27.74 |
| 8009 | 29.11 | 25.06 | NA    | 24.77 | 31.57 | 28.22 | 25.82 | 21.36 | 33.05 | 31.82 | 26.94 | 28.21 |
| 8010 | 30.51 | 24.99 | NA    | 23.36 | 25.27 | 23.82 | 22.19 | 19.74 | 32.29 | 31.13 | 25.49 | 26.86 |
| 8012 | 30.1  | 25.49 | NA    | 25.29 | 27.27 | 24.48 | 22.85 | 21.33 | NA    | NA    | 26.67 | 27.68 |
| 8068 | 28.08 | 25.22 | NA    | 22.24 | 25.9  | 24.22 | 21.62 | 19.98 | 33.72 | 30.33 | 25.95 | 26.8  |
| 8096 | 29.67 | 27.81 | NA    | 26.9  | 25.47 | 24.06 | 22.18 | 20.79 | 32.84 | NA    | 25.91 | 26.96 |
| 8102 | 30.46 | 25.08 | NA    | 24.09 | 26.18 | 24.13 | 23.57 | 20.83 | 33.68 | 31.71 | 25.93 | 27.61 |
| 8111 | 35.91 | 27.93 | NA    | NA    | 35.74 | 32.43 | 32.66 | 21.99 | 35.36 | NA    | 29.25 | 30.42 |
| 8112 | 32.05 | 24.77 | NA    | 25.03 | 26.46 | 24.43 | 22.7  | 19.55 | 33.61 | NA    | 25.97 | 26.87 |
| 8116 | 31.65 | 25.67 | NA    | 26.66 | 26.27 | 25.89 | 23.15 | 21.82 | 34.18 | NA    | 26.49 | 27.39 |
| 814  | 29.4  | 23.31 | NA    | 22.79 | 25.68 | 22.93 | 22.3  | 20.5  | 31.8  | NA    | 25.45 | 27.18 |

TABLE 13b

Weights of the linear discriminant function for ascending number of markers and the associated score values for independent samples 790 and 933.

| Pat-ID | CPVL | CLU | FGL2 | NSMAF | TLR5 | CCR2 | HLA_DPA | ILR7 | ZFANDA | CD59 | C4orf18 | KIA_A0146 |
|---|---|---|---|---|---|---|---|---|---|---|---|---|
| 933 | 28.58 | 26.82 | 27.87 | 29.29 | 27.23 | 34.95 | 26.72 | 25.89 | 31.44 | 29.46 | 29.18 | NA |
| 790 | 27.18 | 26.19 | 26.37 | 28.12 | 26.17 | 32.42 | 25.58 | 26.79 | 30.16 | 27.97 | 26.63 | 33.53 |

| Pat-ID | EPC1 | MME | IGKCem | CD82 | FGL2_0 | BZRP | UBC | SNAPC | IL18 | CASP8 | ITGAL | CASP8 |
|---|---|---|---|---|---|---|---|---|---|---|---|---|
| 933 | NA | 26.54 | 20.00 | 23.99 | 23.69 | 23.92 | NA | 34.55 | NA | 28.16 | NA | 28.16 |
| 790 | 31.78 | 25.88 | 23.19 | 23.56 | 22.25 | 23.73 | 21.13 | 33.13 | 36.99 | 26.60 | 25.18 | 26.60 |

Legends for the gene names:

| Gene Symbol | Corresponding SeqID | Gene Symbol | Corresponding SeqID |
|---|---|---|---|
| MME | 443, 444, 445, 446 | KIAA0146 | 261 |
| CCR2 | 529, 530 | EPC1 | 280 |
| CD59 | 572, 572, 573, 574 | TLR5 | 431 |
| NSMAF | 527 | CLU | 575, 576 |
| IL7R | 541 | C4orf18 | 611, 612 |
| HLA-DPA1 | 613 | BZRP | 601, 602 |
| FGL2 | 615 | CD82 | 470, 471 |
| CPVL | 619, 620 | IGKC | 401 |
| MON2 | 248 | | |

Example 3

Drawing Up a Classifier for the Identification of SIRS and Sepsis Patients by Means of Conventional PCR Measurement of the Gene Expression Patients with pneumonia and peritonitis were selected as typical sepsis representatives, and in case of the SIRS patients those with major heart surgery (cardiopulmonaler bypass, CPB), as these make up the majority of SIRS patients in an ICU (see Table 14).

Total RNA was isolated from the patients' blood and transcribed to cDNA. The latter was utilized as a template in the assay.

TABLE 14

List of examined patients

| Patient ID | Sepsis | | SIRS |
|---|---|---|---|
| | Peritonitis | Pneumonia | |
| 714 | X | | |
| 6008 | X | | |
| 6009 | X | | |
| 6025 | X | | |
| 6035 | X | | |
| 6040 | X | | |
| 6046 | X | | |
| 6062 | X | | |

TABLE 14-continued

List of examined patients

| Patient ID | Sepsis | | | SIRS |
| --- | --- | --- | --- | --- |
| | Peritonitis | Pneumonia | | |
| 6065 | X | | | |
| 6073 | X | | | |
| 6075 | X | | | |
| 6084 | X | | | |
| 6032 | | X | | |
| 6048 | | X | | |
| 6063 | | X | | |
| 6070 | | X | | |
| 6085 | | X | | |
| 6104 | | X | | |
| 6141 | | X | | |
| 814 | | | | X |
| 8001 | | | | X |
| 8002 | | | | X |
| 8009 | | | | X |
| 8010 | | | | X |
| 8012 | | | | X |
| 8068 | | | | X |
| 8096 | | | | X |
| 8102 | | | | X |
| 8111 | | | | X |
| 8112 | | | | X |
| 8116 | | | | X |

The markers for classification were selected from the biomarker pool (see Example 1) and exhibit strong differential gene expression in patient groups diagnosed with and without sepsis.

Table 15 contains a list of the gene products of the gene expression markers that were used for the classification, as well as their description. Table 16 is a list of the primers used in the PCR and the associated SeqIds. Several primer combinations are possible for each target sequence; the table represents only one of many possibilities.

TABLE 15

Gene products of the gene expression biomarkers used for the classification, as well as their description

| Markers | Description (NCBI database, http://www.ncbi.nlm.nih.gov/) |
| --- | --- |
| BZRP | Benzodiazepine receptor |
| CD82 | CD82 molecule |
| FGL2 | Fibrinogen-related protein |
| HLA-DPA1 | Major histocompatibility complex, class II, DP alpha 1 |
| CPVL | Carboxypeptidase vitellogenetic-like gene |
| MME | Metallomembrane endopeptidase |
| IL7R | Interleukin 7 receptor |
| CCR2 | Chemokine (C-C motif) receptor 2 |
| EPC1 | Enhancer of polycomb homolog 1 |
| KIAA0146 | |
| C4orf18 | Chromosome 4 open reading frame 18 |
| MON2 | = KIAA1040, MON2 homolog |
| NSMAF | Neutral sphingomyelinase (N-SMase) activation associated factor |
| TLR5 | Toll-like receptor 5 |
| CLU | Clusterin |
| UBC (Referenzgen) | Ubiquitin |
| ITGAL (Referenzgen) | Integrin, alpha L |
| SNAPC(Referenzgen) | Small nuclear RNA activating complex |

TABLE 16

List of primers used. Several primer combinations are possible for each target sequence; the table only represents one possibility of many.

| Marker and reference genes | Primers for quantitative PCR | |
| --- | --- | --- |
| BZRP | forward | 687 |
| (SeqID 601, 602) | reverse | 688 |
| CD82 | forward | 689 |
| (SeqID 470, 471) | reverse | 690 |
| FGL2 | forward | 693 |
| (SeqID 615) | reverse | 694 |
| HLA-DPA1 | forward | 695 |
| (SeqID 613) | reverse | 696 |
| CPVL | forward | 697 |
| (SeqID 619, 620) | reverse | 698 |
| MME | forward | 699 |
| (SEQID 443, 444, 445, 446) | reverse | 700 |
| IL7R | forward | 701 |
| (SeqID 541) | reverse | 702 |
| CCR2 | forward | 703 |
| (SeqID 529, 530) | reverse | 704 |
| EPC1 | forward | 705 |
| (SeqID 280) | reverse | 706 |
| KIAA0146 | forward | 707 |
| (SeqID 261) | reverse | 708 |
| C4orf18 | forward | 709 |
| (SeqID 611, 612) | reverse | 710 |
| MON2 | forward | 711 |
| (SeqID 248) | reverse | 712 |
| NSMAF | forward | 713 |
| (SeqID 527) | reverse | 714 |
| TLR5 | forward | 715 |
| (SeqID 431) | reverse | 716 |
| CLU | forward | 717 |
| (SeqID 575, 576) | reverse | 718 |
| UBC | forward | 723 |
| (SeqID 678) | reverse | 724 |
| ITGAL | forward | 725 |
| (SeqID 676, 677) | reverse | 726 |
| SNAPC | forward | 727 |
| (SeqID 679) | reverse | 728 |

Experimental Execution

Blood Sampling and RNA Isolation:
  The patient's full blood was taken at the intensive care unit by means of the PAXGene kit in accordance with the manufacturer's (Qiagen) specifications, and the RNA was isolated.

Reverse Transcription:
  From each patient sample, 4 µg of the total RNA was transcribed to complementary DNA (cDNA) by the reverse transcriptase Superscript II (Invitrogen) in a 20-µl batch (contains 1 µl of 10 mM dNTP-Mix of Fermentas and 1 µl of 0.5 µg/µl Oligo(dT) primer). The RNA was then removed from the batch by alkaline hydrolysis. The reaction batches were not purified but filled up with water to 50 µl.

PCR:
  The patient cDNA was diluted 1:500 (or 1:50 for 4 markers, SNAPC, EPC1, KIAA0146 and MON2) with water, with 1 µl each being utilized in the PCR. For each marker one PCR plate (96 wells, Nerbe Plus) was pipetted with all 31 patients and No-Template-Controls (NTC) in triple determination.

PCR batch per well (13 µl) 1 µl template cDNA 1:500 or 1:50 0.5 µl forward
  primer, 10 mM
  0.5 µl reverse primer, 10 mM
  1.3 µl 10× buffer I
  0.05 µl Accuprime Taq-Polymerase
  9.7 µl water A mastermix without template was prepared, which was stepped in 12-µl aliquots in the PCR plate and to each of which the patient cDNA was pipetted (see composition of the PCR reaction batch).

The subsequent PCR program was constructed as follows:

| | | |
|---|---|---|
| 94° C. | 2 min (activation of the polymerase) | |
| 94° C. | 30 sec (denaturing) | |
| 55° C. | 30 sec (addition) | } 32 x bzw 38 x |
| 68° C. | 30 sec (extension) | |
| 68° C. | 2 min (final extension) | |

A Mastercycler Gradient by the company Eppendorf was used.

Detection of the PCR Products:

A 1.1-time SYBR Green solution was prepared. To this end, 100 µl of a 100×SYBR Green stock solution (prepared from a 10.000×SYBR Green stock solution by the company BMA, BioWhittaker Molecular Applications) was pipetted to 8.9 ml of water and mixed. After the PCR, 90 µl each of this solution was added to each PCR batch, and this mixture was then transferred into a black plate (96 wells, Greiner). Then this plate was measured in a fluorescence measuring apparatus (TECAN GENios) at 485 nm stimulation wavelength/535 nm emission wavelength.

Data Analysis:

Data analysis was performed under the free software R Project Version 2.6.1 which is available under www.r-project.org.

Data Pre-Processing:

The measured expression signals (see Table 16) were stored in the Excel format, averaged via the 3-time determinations, and the NTC values were subtracted for each marker. Patient 6065 with 15 missing values was excluded from the analysis. Single missing values were replaced with the knn algorithm (for which the function pamr.knnimpute from the R library pamr was used). The averaged signals were log-2-transformed. For normalization, the mean value of the 3 housekeeper genes was subtracted from the associated marker genes for each patient.

Classification:

In order to arrange the gene markers in accordance with their quality of separation, the Wilcoxon rank-sum test was performed in which the patient groups with and without an infectious complication were compared. According to this, genes with p<0.001 were arranged in accordance with the Hodge-Lehmann estimator, the remaining ones in accordance with the p value proper.

For classification, the linear discriminant analysis [Hastie et al., 2001] was used (for the calculation, the function lda in the R-Packet MASS was used). The estimated weights ($w_0$, $w_1$, ..., $w_p$) of the linear discriminant function $f_{LD}$ with p markers were summarized in Table 17. For a measurement having the values ($x_1$, ..., $x_p$), the associated score was calculated in accordance with the formula $$f_{LD}(x_1, \ldots, x_p) = \sum_{i=1}^{p} w_i x_i - w_0$$

A positive value of the function resulted in assignment to the group with an infectious complication, and a negative value of the function in association to the group without an infectious complication.

In the first step, the separability of the training data set was examined by means of simple cross-validation. Then two independent samples were classified, of one each of the two examined groups of patients (Patient 933 and 790). For this the raw measurement signals were pre-processed in the same way as the training data.

Results

Figure 11:
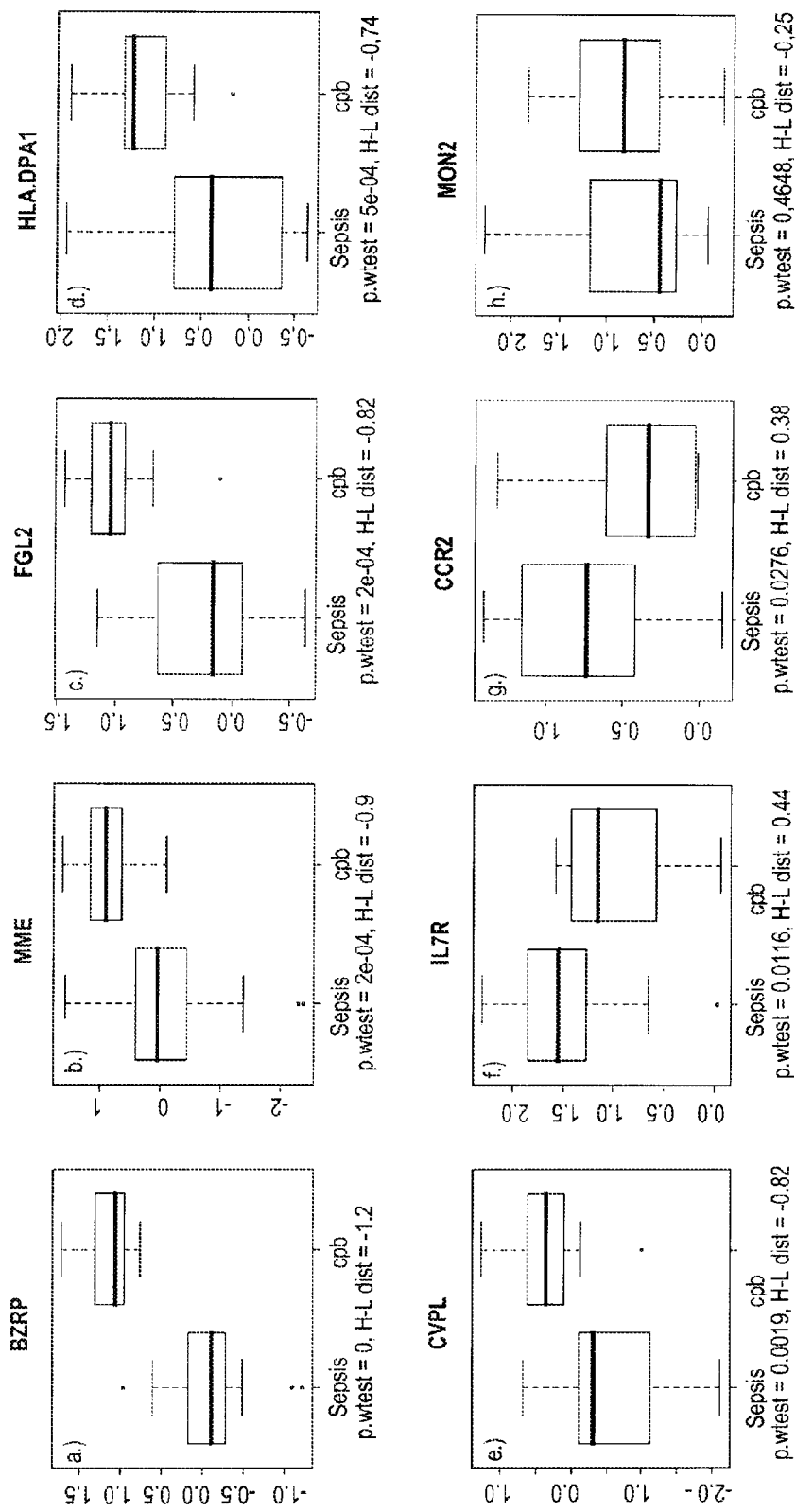
FIG. 11 is a schematic representation of the derived score value and the classification into four areas; the classification result is projected onto this scale.
Figure 11:
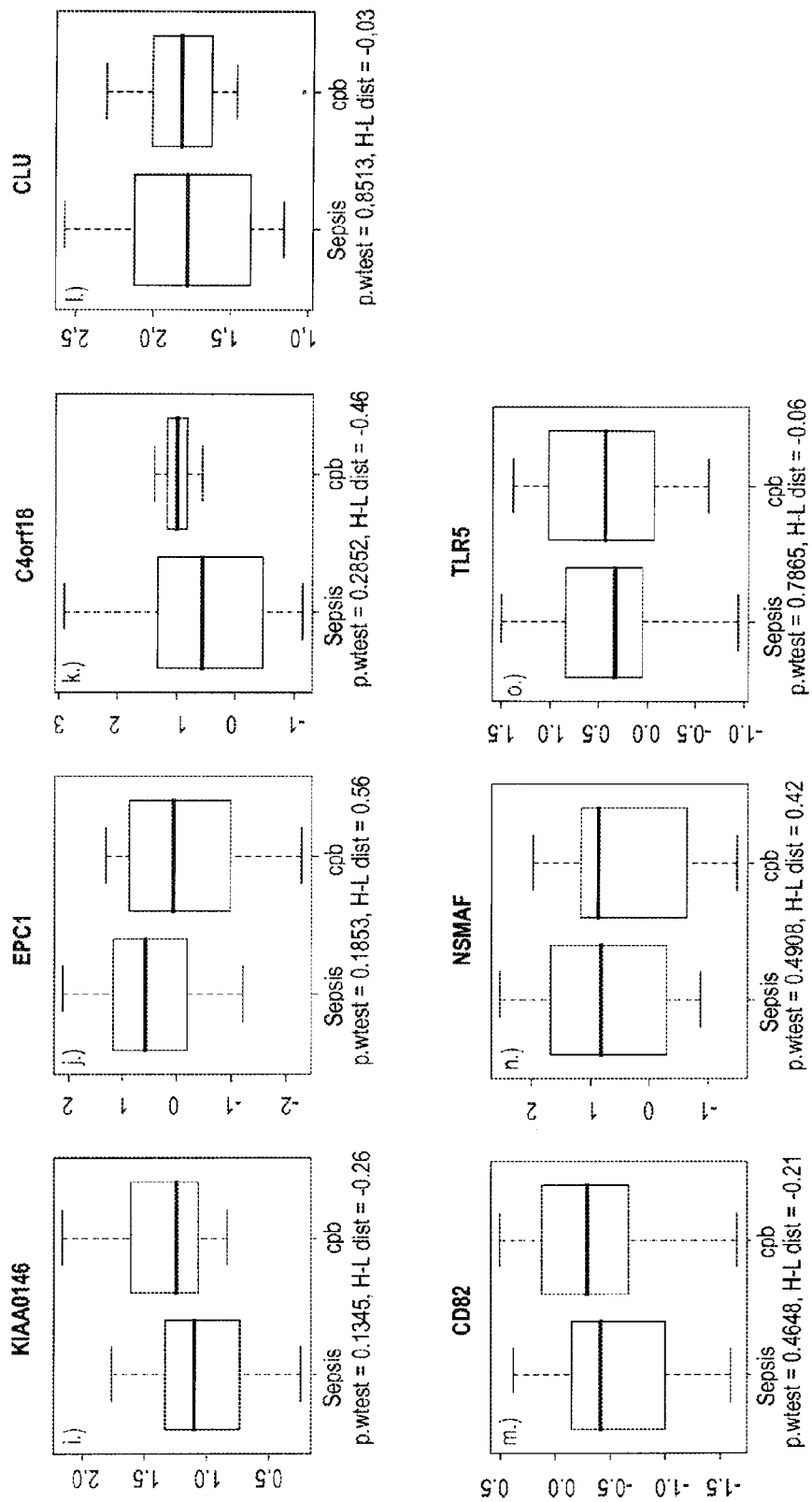

The arrangement of the genes and the associated values are summarized in FIG. 11. The expression differences between the groups: box plots of the 15 markers drawn up from 31 patient samples (19 with diagnosed sepsis, 12 with SIRS) are represented. By means of the box plots, the distribution of the Ct values per group was represented gene by gene. These Ct values were generated for each patient sample by means of real-time PCR on the patient's cDNA (Biorad IQ5) and normalized via the Ct values of three reference genes. On the x-axis, the p value and the Hodge-Lehmann estimator of the Wilcoxon rank-sum test are indicated. In the classification, a sensitivity of 100% and a specificity of 83% were obtained with the simple cross-validation 1, which corresponds to a false classification of 2 non-infectious samples.

Figure 12:
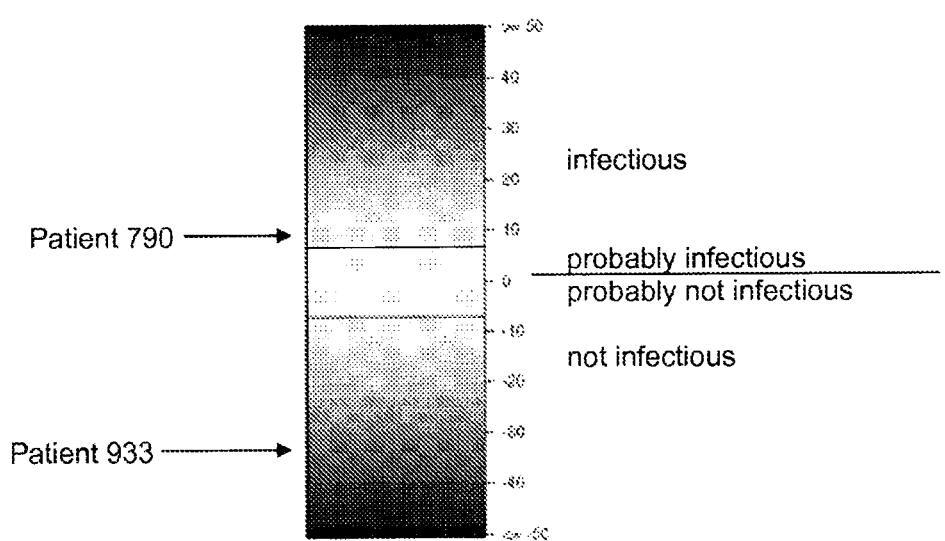
FIG. 12 is a representation of the expression differences between the patient groups: box plots of the markers produced from 31 patient samples (19 diagnosed with sepsis, 12 with SIRS); the legend explains the gene symbols used.

Both of the two independent samples were classified correctly. FIG. 12 shows a schematic representation of the derived score value and the subdivision into 4 areas. If the calculated score is higher than 6.5, there is a 95-% probability of the patient having a sepsis. If the score is less than −6.5, the probability of the patient not having a sepsis likewise is 95%. The classification result was projected onto this scale. The score of sample 933 assumed the value of −38.7 and was classified as non-infectious; the score of sample 790 assumed the value of 9.1 and was classified as infectious.

Table 18a contains the raw data from the fluorescence measurements by SYBR Green at the TECAN GENios. Table 18b shows the raw data of the independent patient samples as well as the legend for the gene names and their assignment to the SeqIDs.

TABLE 17

Coefficients of the linear discriminant function

| Designation | SeqID | Value |
|---|---|---|
| w0 | — | 5.16 |
| w1 | 601, 602 | −34.31 |
| w2 | 443, 445, 446, 446 | 0.72 |
| w3 | 615 | −1.93 |
| w4 | 613 | −1.30 |
| w5 | 619, 620 | −11.25 |
| w6 | 541 | 1.03 |
| w7 | 529, 530 | 28.05 |
| w8 | 261 | 3.31 |
| w9 | 280 | 3.42 |
| w10 | 611, 612 | −1.91 |
| w11 | 248 | 1.61 |
| w12 | 470, 471 | −9.74 |
| w13 | 527 | 4.03 |
| w14 | 431 | −13.20 |
| w15 | 575, 576 | 27.28 |

TABLE 18a

Raw data from the fluorescence measurements by SYBR Green at the TECAN GENios

| Pat.-ID | MME | CPVL | EPC1(2) | EPC1(6) | FGL2 | CLU | IL7R | TLR5 | CCR2 | C4orf18 |
|---|---|---|---|---|---|---|---|---|---|---|
| 714 | 6776 | 4662 | 5680 | 11349 | 5289 | 12677 | 18287 | 6400 | 8718 | 12675 |
| 6008 | 4569 | 2829 | 2046 | 8136 | 4025 | 11302 | 16884 | 4009 | 6787 | 3677 |

TABLE 18a-continued

Raw data from the fluorescence measurements by SYBR Green at the TECAN GENios

| | | | | | | | | | | |
|---|---|---|---|---|---|---|---|---|---|---|
| 6009 | 3992 | 1272 | 10576 | 2411 | 5151 | 14002 | 8671 | 8761 | 10023 | 7492 |
| 6025 | 285 | 739 | 6554 | 7391 | 1944 | 13174 | 8998 | 2376 | 4336 | 1929 |
| 6035 | 1341 | 3037 | 2575 | 11952 | 5056 | 11266 | 8522 | 6328 | 5690 | 8233 |
| 6040 | 492 | 240 | 5313 | 3988 | 4659 | 16296 | 6181 | 6838 | 5719 | 3178 |
| 6046 | 849 | 4556 | 5854 | 7309 | 2916 | 14813 | 10597 | 2205 | 5585 | 3789 |
| 6062 | NA | 604 | 4581 | 2095 | 3738 | 6449 | 5775 | 5421 | 4954 | 359 |
| 6065 | NA | 458 | NA | 264 | NA | 200 | NA | 605 | 3765 | NA |
| 6073 | 283 | 1310 | 3906 | 2754 | 2913 | 11357 | 8438 | 6047 | 5121 | 2260 |
| 6075 | 546 | NA | 1138 | 1124 | 1405 | 12797 | 10361 | 4952 | 5743 | 1174 |
| 6084 | 4603 | 4402 | 7008 | 4616 | 7522 | 11658 | 10180 | 4807 | 6790 | 3762 |
| 6032 | 4874 | 1886 | 6550 | 4143 | 4705 | 15556 | 9486 | 4173 | 4666 | 11031 |
| 6048 | 342 | 1025 | 5274 | 10894 | 2809 | 7557 | 9920 | 4146 | 6675 | 11782 |
| 6063 | 5197 | 6313 | 9976 | 7580 | 8752 | 14186 | 9784 | 2498 | 5173 | 7298 |
| 6070 | 1673 | 3428 | 4175 | 4582 | 4541 | 12960 | 5227 | 3157 | 4968 | 7786 |
| 6085 | 686 | 2924 | 5292 | 1680 | 3113 | 12758 | 11822 | 3889 | 4828 | 7698 |
| 6104 | 5224 | 3225 | 7071 | 5258 | 4491 | 9672 | 11199 | 4133 | 6318 | 2635 |
| 6141 | 5944 | 1168 | 5140 | 6091 | 3578 | 10971 | 9739 | 4479 | 4582 | 14834 |
| 814 | 12934 | 5271 | 10594 | 9261 | 9605 | 8647 | 11386 | 2755 | 6856 | 9406 |
| 8001 | 8759 | 5572 | 9100 | 6293 | 9566 | 11435 | 10471 | 3190 | 4213 | 7714 |
| 8002 | 4437 | 5537 | 5915 | 1827 | 6679 | 13585 | 8989 | 3387 | 4257 | 6126 |
| 8009 | 7288 | 5559 | 10691 | 4887 | 9462 | 12724 | 10099 | 4694 | 4711 | 7073 |
| 8010 | 6629 | 4967 | 7258 | 6419 | 6816 | 12938 | 4638 | 6162 | 4411 | 7432 |
| 8012 | 5758 | 4165 | 4373 | 2941 | 7520 | 13664 | 3770 | 4618 | 3782 | 6498 |
| 8068 | 6057 | 5997 | 6452 | 6162 | 7425 | 10219 | 6614 | 5482 | 6200 | 6454 |
| 8096 | 2475 | 3685 | 4639 | 1560 | 6904 | 13196 | 7933 | 6426 | 4412 | 4731 |
| 8102 | 6716 | 3617 | 5313 | 456 | 7665 | 10233 | 3319 | 3688 | 3834 | 6259 |
| 8111 | 6039 | 6729 | 5916 | 1394 | 7933 | 12354 | 7743 | 5030 | 4877 | 7430 |
| 8112 | 6191 | 1608 | 9961 | 3459 | 7705 | 13789 | 7820 | 8432 | 3301 | 8205 |
| 8116 | 6100 | 3319 | 7925 | 741 | 7040 | 12383 | 5662 | 6626 | 4948 | 6624 |

| Pat.-ID | HLADPA1 | NSMAF | KIAA0146 | MON2 | CD82 | BZRP | ITGAL | UBC | SNAPC |
|---|---|---|---|---|---|---|---|---|---|
| 714 | 7077 | 21405 | 5982 | 4833 | 2543 | 4724 | 6851 | 6489 | 2908 |
| 6008 | 7420 | 11210 | 9183 | 5008 | 2493 | 4333 | 3981 | 3638 | 3861 |
| 6009 | 5710 | 5134 | 8504 | 8573 | 2193 | 4826 | 7466 | 5023 | 4430 |
| 6025 | 1935 | 13141 | 6454 | 4664 | 2503 | 4395 | 2852 | 2916 | 3292 |
| 6035 | 2480 | 2855 | 6521 | 4499 | 3052 | 1513 | 4152 | 3727 | 2852 |
| 6040 | 4929 | 3543 | 9001 | 6900 | 2935 | 2945 | 7112 | 5961 | 5961 |
| 6046 | 6152 | 4185 | 7453 | 5840 | 3388 | 4049 | 3876 | 4354 | 4467 |
| 6062 | 2153 | 1046 | 5670 | 5139 | 2072 | 1780 | 657 | 4033 | 2647 |
| 6065 | NA | NA | 599 | 3642 | 881 | NA | NA | NA | NA |
| 6073 | 1839 | 2319 | 7387 | 4834 | 3732 | 3008 | 3236 | 4648 | 1540 |
| 6075 | 47 | 4283 | 6808 | 11327 | 3190 | 1999 | 2722 | 4194 | 1525 |
| 6084 | 6229 | 14416 | 7917 | 5100 | 1822 | 4317 | 6374 | 4889 | NA |
| 6032 | 5674 | 4226 | 7710 | 3980 | 2021 | 2717 | 3131 | 2873 | 3944 |
| 6048 | 4147 | 12507 | 6385 | 9968 | 1410 | 4967 | 2717 | 3193 | 1884 |
| 6063 | 6604 | 9538 | 9881 | 5229 | 3549 | 4148 | 5997 | 4999 | 2027 |
| 6070 | 4177 | 4089 | 7373 | 10548 | 2437 | 3312 | 4158 | 2582 | 959 |
| 6085 | 6243 | 11636 | 5985 | 4280 | 1193 | 2569 | 4279 | 3593 | NA 37 |
| 6104 | 4849 | 2757 | 7944 | 5183 | 2837 | 3263 | 4620 | 4351 | 3132 |
| 6141 | 7573 | 11500 | 4244 | 4474 | 1595 | 3891 | 2263 | 3766 | 910 |
| 814 | 9684 | 8604 | 10906 | 5117 | 4654 | 7987 | 5975 | 4185 | 3028 |
| 8001 | 9114 | 11611 | 7207 | 11711 | 3405 | 7322 | 4914 | 3039 | 2974 |
| 8002 | 7214 | 4084 | 7426 | 3997 | 3316 | 8043 | 7496 | 3197 | 3007 |
| 8009 | 11044 | 11623 | 10776 | 8011 | 3342 | 7915 | 5220 | 3920 | 4867 |
| 8010 | 7879 | 5700 | 12571 | 8412 | 3601 | 7044 | 2813 | 3203 | 3920 |
| 8012 | 5553 | 1566 | 6603 | 3180 | 1756 | 7745 | 4761 | 2804 | 182 |
| 8068 | 9300 | 5038 | 5567 | 3873 | 1501 | 6851 | 4274 | 3854 | 933 |
| 8096 | 5280 | 5104 | 11899 | 9526 | 3796 | 8811 | 4429 | 2091 | 2057 |
| 8102 | 9582 | 1232 | 8333 | 5700 | 2288 | 6729 | 4533 | 3120 | 2973 |
| 8111 | 8303 | 3869 | 7347 | 7996 | 2892 | 7171 | 6176 | 3079 | 2063 |
| 8112 | 3611 | 12691 | 10431 | 7388 | 3941 | 9586 | 5079 | 1264 | 5133 |
| 8116 | 7444 | 1277 | 10330 | 6683 | 1152 | 8147 | 5996 | 1582 | 4992 |

TABLE 18b

| Pat-Id | MME | CPVL | EPC1(2) | EPC1(6) | FGL2 | CLU | IL7R | TLR5 | CCR2(2) | C4orf18 |
|---|---|---|---|---|---|---|---|---|---|---|
| Patient 933 | 10228 | 2916 | 14772 | 1307 | 5904 | 4615 | −54 | 1857 | 1602 | 12217 |
| Patient 790 | 8386 | 6096 | 13358 | 10777 | 10457 | 12244 | 8373 | 8713 | 4955 | 8613 |

TABLE 18b-continued

| Pat-Id | HLA_DPA1 | NSMAF | KIAA0146 | MON2 | CD82 | BZRP | ITGAL | UBC | SNAPC |
|---|---|---|---|---|---|---|---|---|---|
| Patient 933 | 13202 | 7254 | 442 | 21048 | 1098 | 3554 | 4554 | 7291 | 5304 |
| Patient 790 | 13368 | 6777 | 6742 | 17021 | 3502 | 4406 | 8410 | 7291 | 20269 |

Legend for the gene names, association to the SeqIDs:

| Gene symbol | Corresponding SeqID | Gene symbol | Corresponding SeqID |
|---|---|---|---|
| MME | 443, 444, 445, 446 | KIAA0146 | 261 |
| CCR2 | 529, 530 | TLR5 | 431 |
| CD59 | 571, 572, 573, 574 | CLU | 575, 576 |
| NSMAF | 527 | C4orf18 | 611, 612 |
| IL7R | 541 | BZRP | 601, 602 |
| HLA-DPA1 | 613 | CD82 | 470, 471 |
| FGL2 | 615 | IGKC | 401 |
| CPVL | 619, 620 | EPC1 | 280 |

Example 4

Pathogen Type—Gram vs. Gram-Differential Gene Expression in Septic Patients with Gram-Negative and Gram-Positive Sepsis Pathogens as Well as Identification and Partial Validation of the Biomarker Candidates for Diagnostic Use In genome-wide gene expression analyses on microarray platforms, biomarkers were identified which are expressed with different intensity in septic patients with infections by gram-negative and gram-positive bacteria. Starting out from this list of biomarkers including 114 markers, it was demonstrated for three markers that these differences in gene expression can be represented by means of quantitative PCR. Gene-specific primers were identified for these 3 markers, and their gene activity was determined by means of quantitative PCR.

Measurement of Gene Expression

Selection of the Group of Patients:

Patient groups with ascertained (identification by blood culture) gram-negative and gram-positive infection were selected from the comprehensive patient database. All of the patients selected for the studies suffered from severe sepsis or septic shock. In most cases, the sepsis originated from a pneumonia (inflammation of the lungs) or from a tracheobronchitis (bronchial inflammation) (see Table 19).

TABLE 19

List of examined patients. Not shaded: patients with gram-negative infection; shaded in light grey: patients with gram-positive infection.

| | Classification | Focus of infection (focus in sepsis) |
|---|---|---|
| 6104.001 | Severe sepsis | Pneumonia (likely) |
| 7120.005 | Septic shock | Pneumonia (positive); intra-abdominal infection (likely) |
| 6058.001 | Severe sepsis | Pneumonia (positive) |
| 6047.003 | Severe sepsis | Pneumonia (likely); tracheobronchitis (likely) |
| 6103.001 | Septic shock | Pneumonia (likely) |
| 7023.001 | Septic shock | Pneumonia (likely) |
| 7040.001 | Septic shock | Deep surgical wound infection (positive); pneumonia (likely) |
| 1015.002 | Septic shock | Pneumonia (positive) |
| 6070.002 | Severe sepsis | Pneumonia (likely); tracheobronchitis (likely) |

These patients were analyzed in a pangenomic gene expression study on the Illumine platform (www.Illumina.com).

Performing Gene Expression Analysis on the Illumina Platform:

For the Illumine sample preparation, the "Illumine Total-Prep RNA Amplification kit" by Ambion (Ambion, USA) is used in accordance with the specifications contained therein. Preparation of hybridization is performed with the "Illumina Gene Expression System".

In the following, the single steps are described in principle:

Reverse Transcription (First Strand cDNA Synthesis)

50-500 ng of RNA is placed in a microcentrifuge tube and filled up to 11 µl with nuclease-free water.

The following reaction mix is pipetted together:

| 1 µl | T7 Oligo (dT) Primer |
|---|---|
| 2 µl | 10X First Strand Buffer |
| 4 µl | dNTP Mix |
| 1 µl | RNase Inhibitor |
| 1 µl | Array Script |

9 µl of the mix is added to the RNA sample and then incubated during 2 hrs at 42° C. The T7 Oligo(dT) nucleotide attaches complementarily to the Poly-A overhang at the 3' end of the mRNA, so that the mRNA is transcribed to cDNA, independently of its sequence, with the aid of ArrayScript. Following incubation during 2 hrs, the reaction vessel is again placed on ice.

Illumina: Second Strand cDNA Synthesis

The following reaction mix is prepared on ice:

| 63 µl | Nuclease-free $H_2O$ |
|---|---|
| 10 µl | 10X Second Strand Buffer |
| 4 µl | dNTP mix |
| 2 µl | DNA polymerase |
| 1 µl | RNase H |

80 µl of the second strand cDNA reaction mix is added to the sample, followed by incubation in the thermocycler during 2 hrs at 16° C. During the second strand synthesis by DNA polymerase, the RNA is simultaneously decomposed by RNase H.

In Vitro Transcription (IVT, for cRNA Synthesis)

At room temperature the following mix is prepared:

| 2.5 µl | T7 10X reaction buffer |
|---|---|
| 2.5 µl | T7 enzyme mix |
| 2.5 µl | Biotin NTP mix |

The prepared mix is added to the sample and incubated during 14 hrs. The T7 enzyme ix contains T7 RNA polymerase, a highly promotor-specific RNA polymerase which requires a DNA template. The T7 oligo(dT) nucleotide used for the reverse transcription includes a T7 promotor sequence which is now recognized by the T7 RNA polymerase. cRNA strands (=antisense RNA) are synthesized which contain biotinylated UTP. The in vitro transcription thus at the same time is an amplification and labeling step. Following incubation, 75 µl of nuclease-free water is added.

Purification:

Second strand cDNA synthesis is followed by a purification step whereby RNA, primers, enzymes, and salt are removed. Another purification step following the in vitro transcription removes enzymes, salt, and non-integrated nucleotides.

Purification takes place via cDNA or cRNA filter cartridges to which the nucleic acids are bound by means of cDNA or cRNA binding buffer. Following the addition of the washing buffer, the filter cartridges are centrifuged dry, and the nucleic acid is eluted with Rnase-free water into a new reaction vessel.

Hybridization:

Hybridization of the cRNA on gene-specific oligonucleotide probes takes place on so-called bead arrays which are disposed on supports, the bead chips. The required buffers, solutions, and hybridization chambers are provided by the manufacturer in the form of the Bead-Chip kit (HumanWG-6 BeadChip-kit, Illumina, www.illumina.com).

1.5 µg of the respective cRNA sample is filled up to 10 µl with RNase-free water. 20 µl of GEX-HYB solution is added to the sample. 200 µl of GEX-HCB is filled into the humidification buffer reservoirs of the hybridization chamber, and the bead chips (Human WG-6 BeadChip, Illumina, www.illumina.com) are placed in the hybridization chamber. 30 µl of sample is applied to the sample opening of the array. The hybridization chamber is closed carefully, and the samples are incubated for 16-20 hrs at 58° C.

The bead chips are immersed in E1BC washing solution and washed in the high-temp buffer at 55° C. This is followed by a washing step at room temperature with E1BC solution, an ethanol washing step, and another washing step with E1BC. After this a blocking step is performed with Block E1 buffer and a labeling step with Block E1+Streptavidin-Cy3, in which the fluorescence-labeled streptavidin binds to the biotinylated nucleotides of the cRNA. Washing is once more performed with E1BC buffer, after which the bead chip is dried by centrifuging (2 min at 500 rpm). Subsequently the bead chip can be scanned by the Bead Array Reader (Illumina Beadstation 500, www.illumina.com).

Evaluation of the Microarray Data:

The bead chip is read fluorometrically with the aid of the Beadarray Reader. The scanner has a resolution of 0.8 µm, so that fluorescence of each of the 48687 bead types placed on an array is measured on at least 9 pixels. Each bead type is present with 5× redundancy at least. With the program Bead Studio 2.0 provided by Illumina, the fluorescence values of a bead type are averaged and output as "Average Signal." Besides the beads serving as a probe for human gene transcripts, there are also bead types acting as negative controls. Their sequences do not hybridize with transcripts from the human genome.

These control beads are used to determine the background signal which is subtracted from each averaged signal. Furthermore the negative controls of the detection p value of each single bead type is determined, which provides information whether it is a genuine signal or whether the measured intensity corresponds to the background. For the further analysis only those bead types are used in which at least one of the ten arrays reached a detection p value of less than 0.01.

For the correction of the systematic measurement error, the normalization by means of Cubic Splines proposed by the data processing program Bead Studio 2.0 (component of Illumina Beadstation 500) was selected. In accordance with recommendations [MAQC-Consortium, 2006], the following correction steps were furthermore added. The data was processed further with the statistics software (http://www.r-.project.org). From all of the bead types selected for further analysis, the smallest averaged signal value is determined. This minimum is subtracted from each averaged signal, so that the smallest averaged signal now assumes the value 0. Moreover the constant 16 is added to each averaged signal before taking the logarithm to the base 2. Following logarithmizing, the smallest averaged signal obtains the value 4. At the same time the averaged signal is prevented from assuming a negative value.

When the expression data of gram-positive and gram-negative samples is compared, the ratio of the expression values is indicated as the "fold change." This value indicates by what factor the transcript in the one sample was expressed differently than in the other sample. In order to obtain the logarithmic fold change, the difference of the mean values of the normalized data of both groups is formed. Here, the fold change of gram-positive relative to gram-negative is indicated:

$$\log_2 \text{FoldChange} = \text{Mean Value}(\text{normdata}(\text{gram}+)) - \text{Mean Value}(\text{normdata}(\text{gram}-))$$

$$\log_2 \text{FoldChange} = \log_2(\text{gram}+/\text{gram}-)$$

Figure 1:
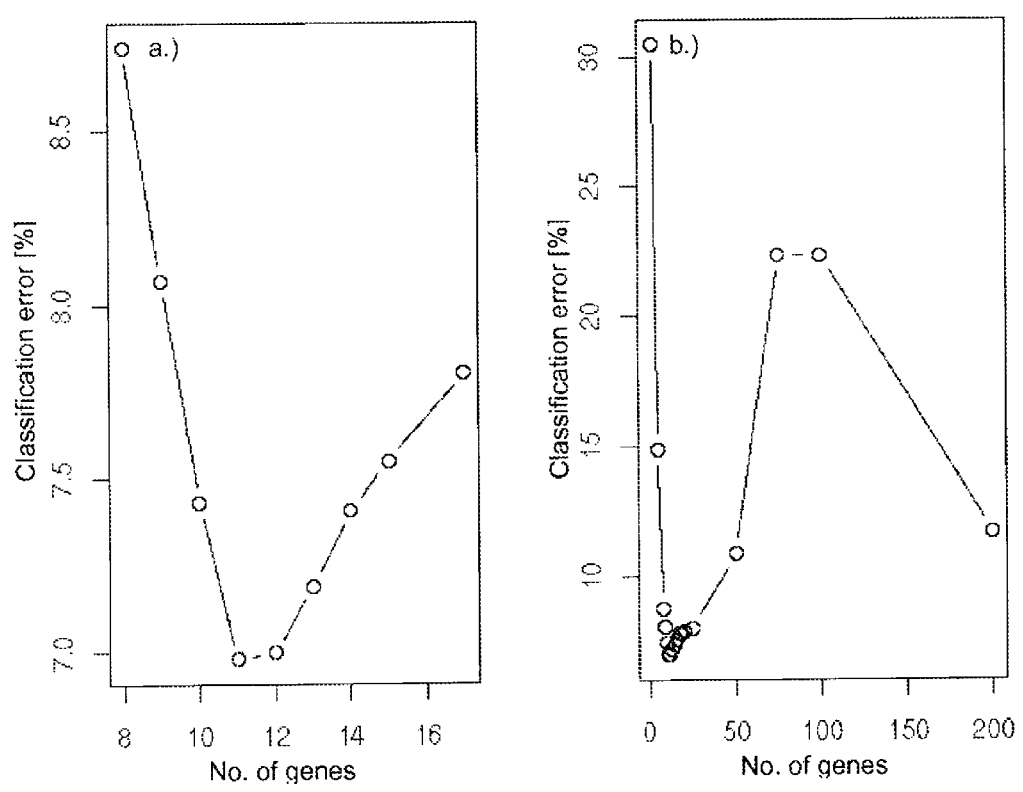
FIG. 1 shows a development of the classification error of LDA in dependence on the number of classification genes; (a) classification error when using 5-200 genes, (b) detail for 8-20 genes.
Figure 2:
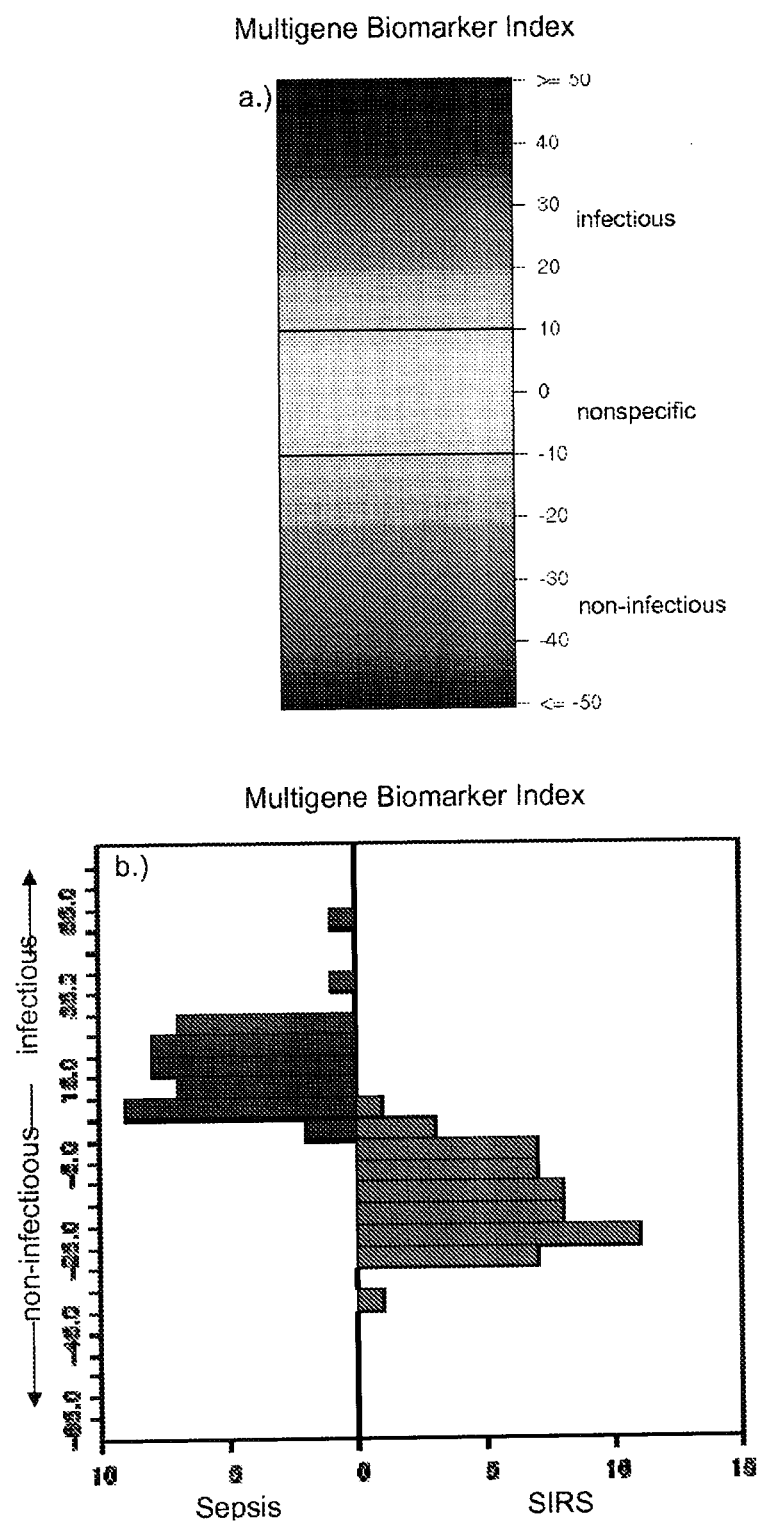
FIG. 2 shows a score (a) and its distribution for the training data set (b)
Figure 3:
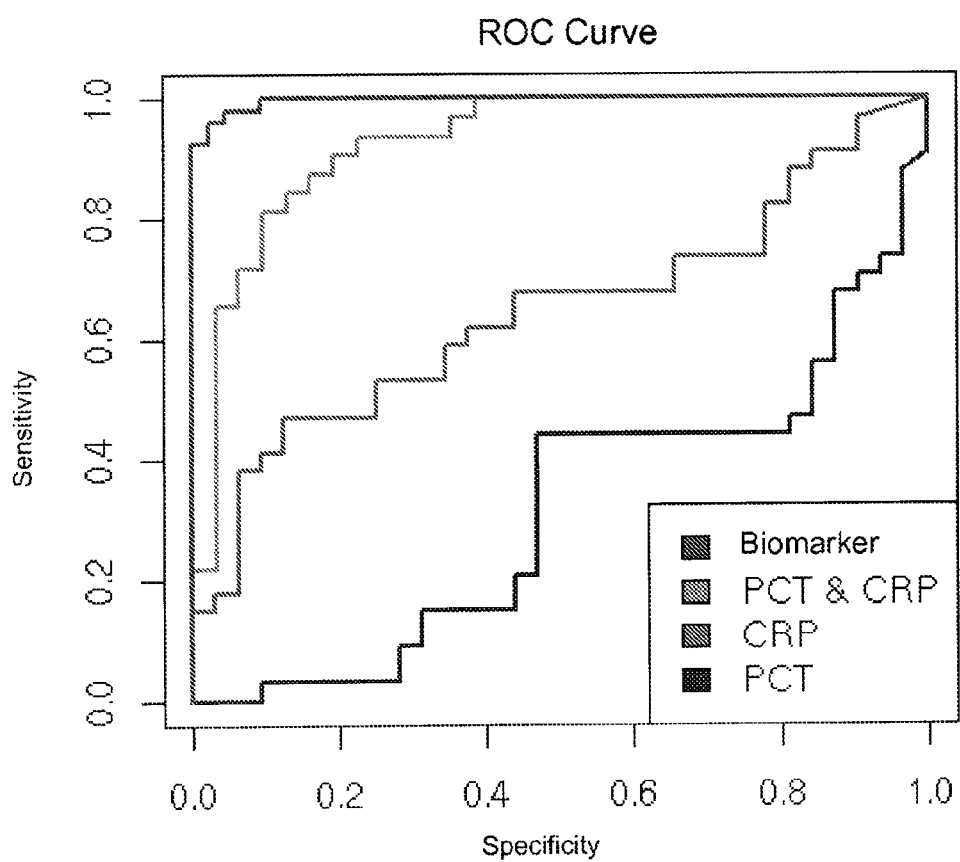
FIG. 3 shows the quality of a multigene biomarker in comparison with conventional monomolecular biomarkers PCT and CRP and their combination, respectively (via LDA)
Figure 4:
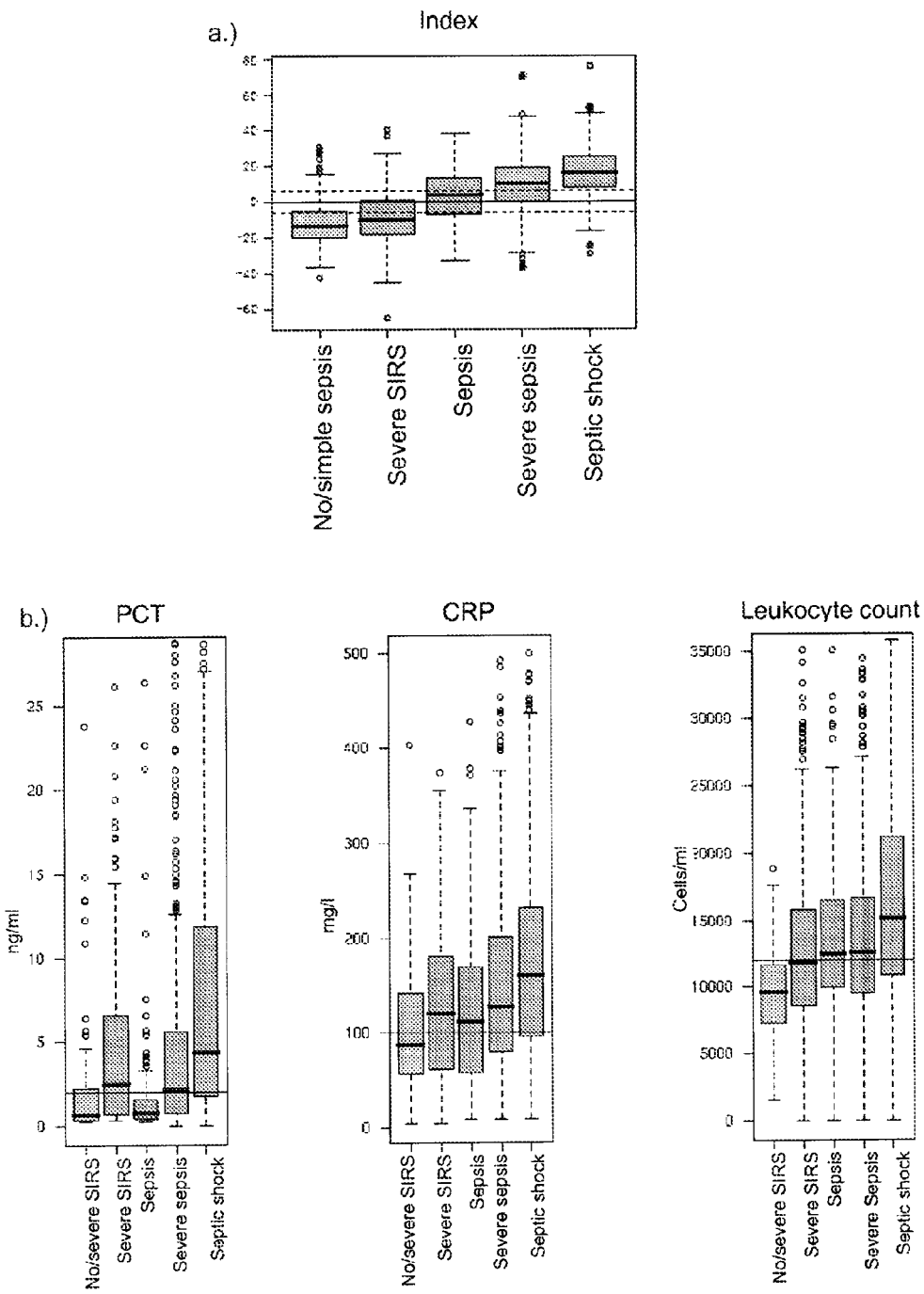
FIG. 4 shows a distribution of the biomarker values as a function of the clinical diagnosis, (a) multigene biomarker score, (b) PCT, CRP and WBC.
Figure 5:
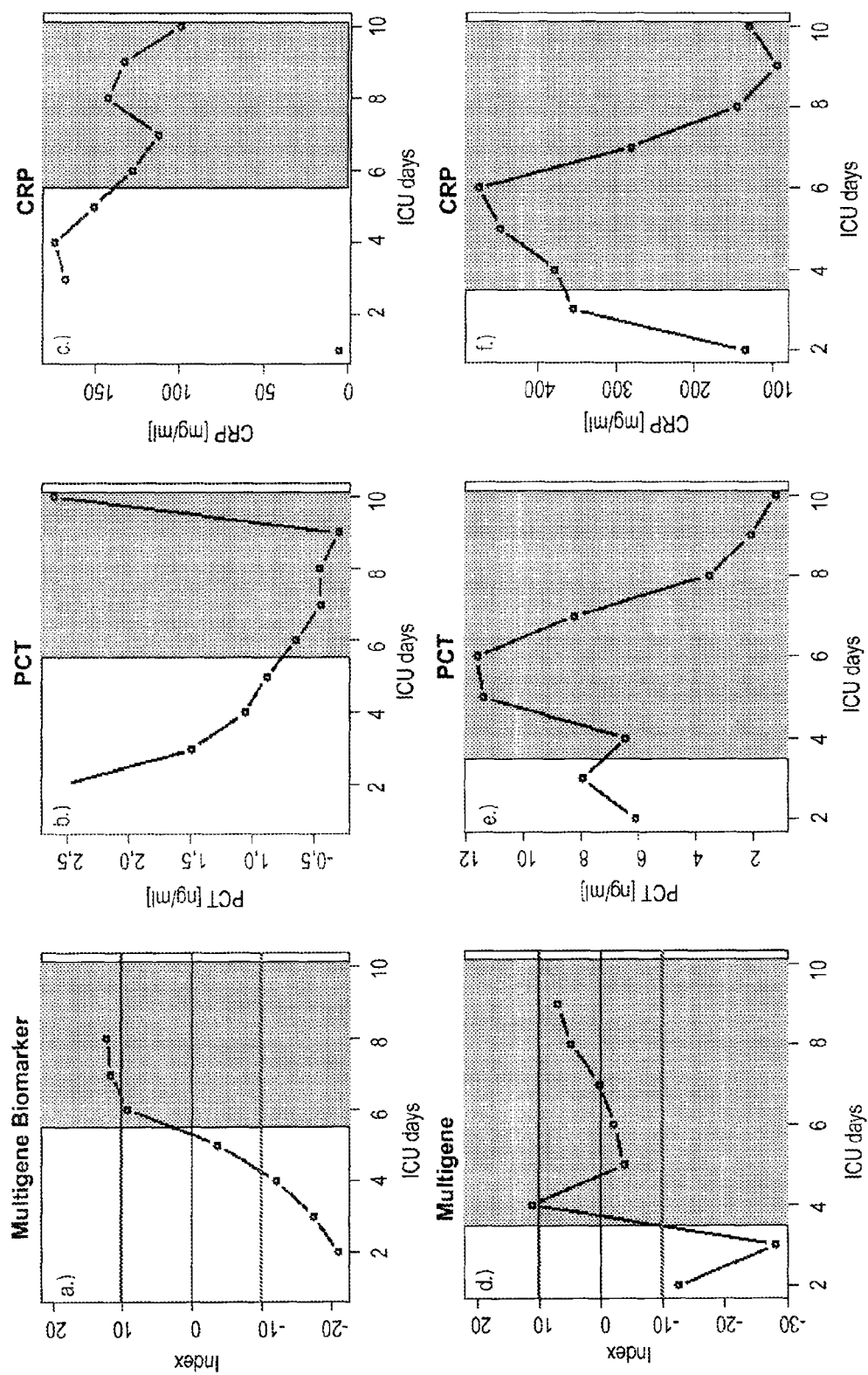
FIG. 5 shows a development of the score for three patients (the grey area marks the days of sepsis diagnosis.
Figure 5:
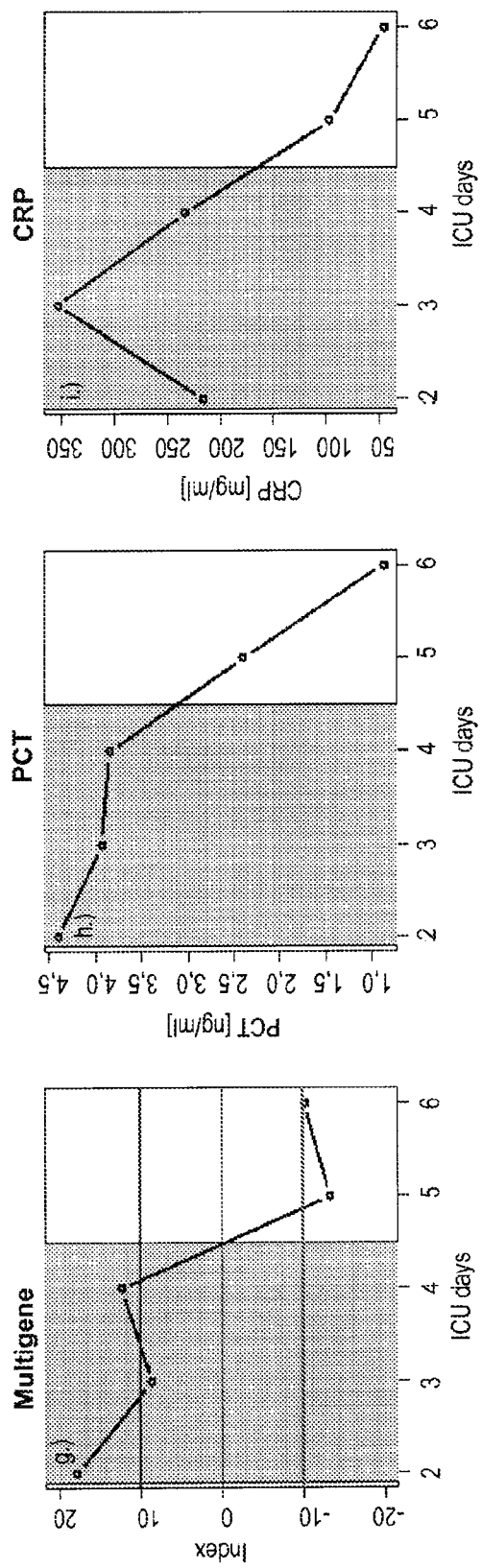
Figure 6:
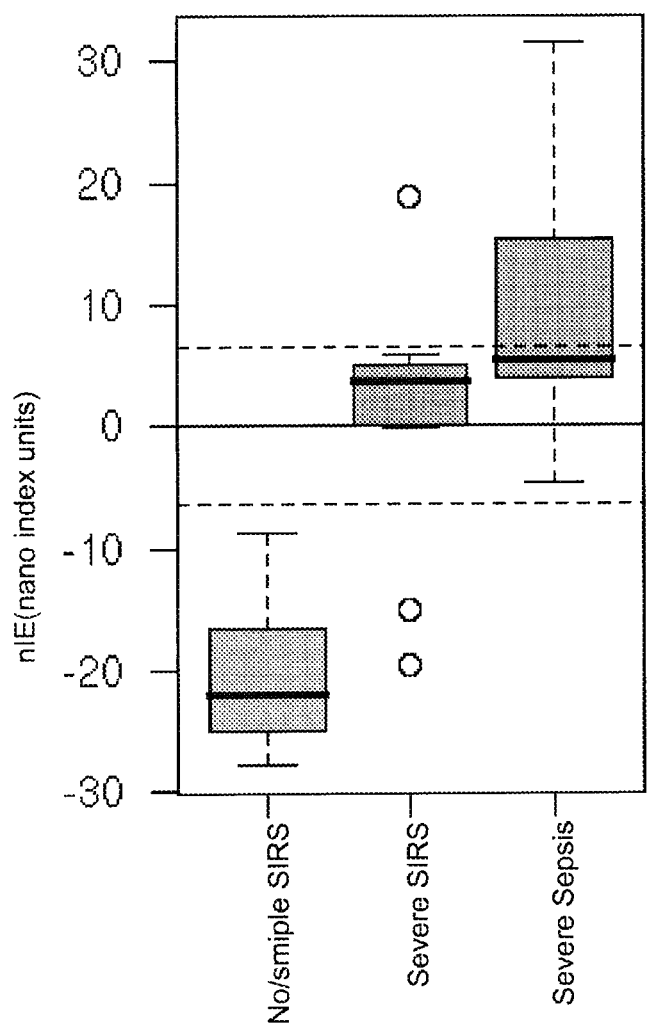
FIG. 6 shows a distribution of the scores for expression data of an external collecting institution.

The FIG. 2 is exponentiated by the logarithmic fold change to obtain a theoretical fold change. If the theoretical fold change assumes a value of less than 1, then the fold change results from the negative reciprocal of the theoretical fold change. In the opposite case, the fold change corresponds to the theoretical fold change:

$$\text{Theoretical Fold Change} = 2^{\log_2 \text{Fold Change}} = 2^{\log_2 (\text{gram}+/\text{gram}-)} = \text{gram}+/\text{gram}-$$

Fold Change: if Theoretical Fold Change < 1

$$\text{then} \quad \text{Fold Change} = -\frac{1}{\text{Theoretical Fold Change}}$$

otherwise  Fold Change = Theoretical Fold Change

A positive fold change means that the corresponding gene is expressed more strongly in the case of a gram-positive infection than in the case of a gram-negative infection.

For each bead type the p value for the t test and the Wilcoxon test is furthermore calculated. Under the assumption that the null hypothesis of the test is correct, the p value indicates the probability of the measured value coming about by chance. If this probability is less than a predetermined limit, it is assumed that the difference is not random.

In Table 20 the identified biomarkers are represented:

TABLE 20

Differential gene expression of transcripts in gram-positive and gram-negative sepsis, measured on the Illumina gene expression platform

| Symbol | Illumina TargetID | Fold Change Gram+ vs Gram− | p value t test | p value wilcoxon test | SeqID | Biological plausibility |
|---|---|---|---|---|---|---|
| FLJ42957 | ILMN_10187 | −2.066 | 0.06351 | 0.09524 | 67 | |
| C22orf5 | ILMN_10219 | −1.572 | 0.00853 | 0.00794 | 68 | |
| GZMH | ILMN_10239 | 2.385 | 0.18916 | 0.22222 | 69 | Participates in cell lysis in cell-mediated immune response; has peptidase and proteolysis activity; participates in apoptose |
| | ILMN_105873 | −1.441 | 0.00716 | 0.01587 | 70 | |
| GPR137B | ILMN_10711 | 1.842 | 0.00413 | 0.00794 | 71 | |
| | ILMN_107750 | −2.114 | 0.00797 | 0.03175 | 72 | Intron of a presumed transcript variant of RNASET2 |
| | ILMN_109087 | −2.060 | −0.09233 | 0.42063 | 73 | |
| LOC728653 | ILMN_109663 | −1.549 | 0.00851 | 0.00794 | 74, 75 | |
| | ILMN_110605 | 1.441 | 0.12945 | 0.00794 | 76 | |
| BC002942 | ILMN_11132 | −1.547 | 0.00218 | 0.00794 | 77 | |
| ITIH4 | ILMN_11142 | −2.215 | 0.20823 | 0.15079 | 78 | Possibly involved in acute-phase reactions |
| MAOA | ILMN_11566 | −3.140 | 0.11311 | 0.30952 | 79 | Important function in the amino metabolism of the central nervous system; decomposes neurotransmitters such as dopamine |
| SDHB | ILMN_12116 | 1.188 | 0.03632 | 0.00794 | 80 | Has electron transport activity |
| | ILMN_122129 | −1.365 | 0.00993 | 0.01587 | 81 | |
| | ILMN_123073 | −1.324 | 0.01229 | 0.00794 | 82 | |
| LOC113386 | ILMN_12569 | 1.562 | 0.00377 | 0.00794 | 83 | |
| LOC285908 | ILMN_12575 | −1.402 | 0.00485 | 0.01587 | 84 | |
| F12 | ILMN_12933 | −2.010 | 0.52542 | 0.30952 | 85 | Activates coagulation factors VII and XI; initiates blood coagulation and fibrinolysis |
| RPS6KA5 | ILMN_13156 | −2.211 | 0.10517 | 0.09524 | 86 | Plays an essential role in transcription activation in response to TNF; responds to oxidative stress |
| GDI1 | ILMN_13492 | −1.530 | 0.04136 | 0.00794 | 87 | Decelerates the dissociation of the GDP of RAB proteins |
| CMIP | ILMN_13851 | −1.282 | 0.01492 | 0.00794 | 88 | |
| VPS13D | ILMN_14155 | −1.250 | 0.01823 | 0.00794 | 89 | |
| LGALS3 | ILMN_14333 | 2.182 | 0.33372 | 0.42063 | 90 | Binds IgE; participates in macrophage activation |
| C1orf74 | ILMN_1469 | 1.307 | 0.00323 | 0.00794 | 91 | |
| EIF1AY | ILMN_14704 | 4.963 | 0.14239 | 0.42063 | 92 | Initiates the translation |
| PCOLCE2 | ILMN_14782 | 2.020 | 0.07343 | 0.09524 | 93 | |
| PRAM-1 | ILMN_14804 | −1.596 | 0.00938 | 0.03175 | 94 | This protein resembles FYB/SLAP-130 which participates in T-cell receptor-mediated signal paths |
| PLAC8 | ILMN_17809 | 2.203 | 0.04188 | 0.09524 | 95 | |
| PAQR6 | ILMN_18415 | −1.532 | 0.01116 | 0.00794 | 96 | Receptor activity |
| NDE1 | ILMN_18439 | −1.416 | 0.02123 | 0.00794 | 97 | |
| TOP3A | ILMN_1902 | −1.337 | 0.01157 | 0.00794 | 98 | Catalyzes temporary breakage and reassociation of single-stranded DNA during transcription |
| ARG1 | ILMN_19494 | −2.076 | 0.06063 | 0.09524 | 99 | Hydrolyzes arginine and is thus involved in the urea metabolism |
| LGALS2 | ILMN_19736 | 2.221 | 0.14025 | 0.09524 | 100 | Binds galactosides |
| HBZ | ILMN_19775 | −2.418 | 0.35974 | 0.42063 | 101 | Oxygen transport activity |
| CYP27A1 | ILMN_2033 | −2.616 | 0.04173 | 0.09524 | 102 | Oxidizes cholesterol intermediate products |
| EIF2AK2 | ILMN_20636 | −1.643 | 0.02192 | 0.00794 | 103 | Binds double-stranded RNA; participates in protein synthesis inhibition |
| CDKN1C | ILMN_20689 | 2.047 | 0.00736 | 0.00794 | 104 | Negative regulation of cell proliferation; cyclin- |

TABLE 20-continued

Differential gene expression of transcripts in gram-positive and gram-negative sepsis, measured on the Illumina gene expression platform

| Symbol | Illumina TargetID | Fold Change Gram+ vs Gram− | p value t test | p value wilcoxon test | SeqID | Biological plausibility |
|---|---|---|---|---|---|---|
| | | | | | | dependent protein-kinase-activity |
| MNT | ILMN_21283 | −1.278 | 0.03776 | 0.00794 | 105 | Acts as a transcription repressor; binds to DNA binding proteins |
| MDFIC | ILMN_21649 | 1.158 | 0.04237 | 0.00794 | 106 | Participates in the transcription regulation of viral genomes |
| ZNFN1A1 | ILMN_22185 | 2.287 | 0.12649 | 0.15079 | 107 | Interacts with promotors of B- and T-cell development; has DNA-binding capabilities and participates in the regulation of transcription |
| KIAA0690 | ILMN_22207 | −1.631 | 0.00181 | 0.01587 | 108 | |
| RPLP0 | ILMN_22954 | 2.264 | 0.29058 | 0.30952 | 109 | Component of the 60S subunit of ribosomes |
| KIAA0367 | ILMN_23214 | −2.755 | 0.04168 | 0.03175 | 110 | |
| FOXC1 | ILMN_23624 | −2.003 | 0.19170 | 0.30952 | 111 | Transcription factor; regulates embryonal development |
| SYT11 | ILMN_23967 | −1.218 | 0.00016 | 0.00794 | 112 | Binds calcium ions; has transporter activity |
| DPEP2 | ILMN_24146 | −1.838 | 0.01433 | 0.00794 | 113 | Has proteolysis and peptidolysis activity; hydrolyzes i.a. the β-lactam ring of some antibiotics |
| TPST1 | ILMN_2477 | −2.715 | 0.17087 | 0.22222 | 114 | Has transferase activity |
| JUP | ILMN_2607 | −2.825 | 0.08747 | 0.03175 | 115 | Element of the cyto-skeleton; participates in cell adhesion |
| ENTPD7 | ILMN_26198 | 2.091 | 0.03844 | 0.00794 | 116 | Hydrolase activity; regulation of stimulus transmission |
| VIPR1 | ILMN_27565 | −2.262 | 0.02954 | 0.03175 | 117 | Receptor for small neuropeptides |
| UBE4B | ILMN_28085 | −1.423 | 0.00118 | 0.00794 | 118 | Catalyzes the construction of ubiqutin chains and thereby enables the breakdown of proteins |
| TTLL4 | ILMN_28183 | −1.443 | 0.00312 | 0.01587 | 119 | Has ligase activity |
| C5orf30 | ILMN_28409 | −2.177 | 0.10035 | 0.09524 | 120 | |
| GBP1 | ILMN_28413 | 2.512 | 0.03832 | 0.09524 | 121 | Binds guanine nucleotides; expression of GBP1 is induced by interferon |
| FLJ12700 | ILMN_28810 | −1.373 | 0.01685 | 0.00794 | 122 | |
| KIAA1539 | ILMN_29031 | −1.233 | 0.01807 | 0.00794 | 123 | |
| DVL2 | ILMN_29320 | −1.272 | 0.01430 | 0.00794 | 124 | Possibly plays a role in signal paths of various Wnt genes |
| SMCY | ILMN_29791 | 2.608 | 0.09136 | 0.30952 | 125 | Has zinc finger domain; binds to DNA |
| XAB2 | ILMN_30213 | −1.392 | 0.01287 | 0.00794 | 126 | Participates in transcription processes |
| TMEM119 | ILMN_30233 | −2.336 | 0.07191 | 0.09524 | 127 | |
| LOC644863 | ILMN_33000 | 1.517 | 0.03096 | 0.00794 | 128 | |
| DAAM2 | ILMN_3540 | −2.565 | 0.13476 | 0.22222 | 129 | Is rho-dependent; recruits profilin to the membrane and supports actin polymerization; is required for transcription activation of serum response factors |
| LOC644037 | ILMN_37144 | 2.015 | 0.16628 | 0.22222 | 130 | |
| LOC400713 | ILMN_37636 | −1.410 | 0.00277 | 0.01587 | 131 | |
| LOC644033 | ILMN_39734 | −2.027 | 0.05730 | 0.15079 | 132 | |
| HEBP1 | ILMN_4128 | 2.047 | 0.03781 | 0.05556 | 133 | Mediates calcium mobilization and chemotaxis of monocytes and dentritic cells |
| ZNF187 | ILMN_4390 | −2.114 | 0.47706 | 0.30952 | 134 | Has transcription factor activity |
| SAMD4B | ILMN_5298 | −1.420 | 0.01003 | 0.00794 | 135 | |

TABLE 20-continued

Differential gene expression of transcripts in gram-positive and gram-negative sepsis, measured on the Illumina gene expression platform

| Symbol | Illumina TargetID | Fold Change Gram+ vs Gram− | p value t test | p value wilcoxon test | SeqID | Biological plausibility |
|---|---|---|---|---|---|---|
| ADORA3 | ILMN_5334 | −2.056 | 0.29105 | 0.22222 | 136 | Interacts with G-protein; protects against heart damage; is possibly involved in cell proliferation and cell death |
| U2AF1L4 | ILMN_5343 | 2.092 | 0.03842 | 0.00794 | 137 | RNA binding, plays a critical role in splicing processes |
| TNNT1 | ILMN_537 | 2.161 | 0.17568 | 0.22222 | 138 | Participates in muscle development |
| TLR9 | ILMN_5498 | −1.478 | 0.00666 | 0.03175 | 404 | Activates the innate immune system after recognition of non-methylated CpG motifs |
| GPC2 | ILMN_6771 | −1.470 | 0.00923 | 0.00794 | 139 | Cell surface proteoglycan |
| NLF2 | ILMN_6857 | −1.346 | 0.15084 | 0.00794 | 140 | |
| THEDC1 | ILMN_7113 | −2.264 | 0.32089 | 0.30952 | 141 | Participates in fatty acid synthesis |
| INHBB | ILMN_7166 | −2.198 | 0.07401 | 0.09524 | 142 | Has tumor suppressor activity; has cytokin activity |
| SNFT | ILMN_7180 | 1.564 | 0.00625 | 0.01587 | 143 | Reacts to pathogens; regulation of transcription |
| | ILMN_73408 | −2.617 | 0.08397 | 0.05556 | 144 | |
| METTL7B | ILMN_7370 | 3.082 | 0.00148 | 0.00794 | 145 | Methyltransferase activity |
| PPP1R10 | ILMN_8464 | −1.310 | 0.03765 | 0.00794 | 146 | This gene is situated in the region of the main histocompatibility complex I; has transcription regulator activity |
| RPS4Y1 | ILMN_8579 | 11.651 | 0.06490 | 0.09524 | 147 | Binds RNA; component of the 40S subunit of ribosomes and thus participates in protein synthesis |
| PAIP1 | ILMN_879 | 1.147 | 0.02433 | 0.00794 | 148 | Participates in translation initiation and protein synthesis |
| CTSL | ILMN_8814 | 2.052 | 0.00248 | 0.01587 | 159 | Cystein-type endopeptidase activity; plays an important role in the protein catabolism |
| | ILMN_89024 | −1.472 | 0.03363 | 0.00794 | 150 | |
| KIAA1324 | ILMN_9289 | −2.497 | 0.09589 | 0.15079 | 151 | |
| TAOK2 | ILMN_9392 | −1.359 | 0.00962 | 0.01587 | 152 | Positively regulates the JNK cascade; reacts to stress |

The gene activity of three markers from this list was measured by means of quantitative PCR on the cDNA of the same patients in order to reproduce the data by a different method.

The three markers as well as a representative primer pair for the quantification by means of real-time PCR are represented in Table 21. Furthermore, for the relative quantification so-called reference genes with constant expression in the respective tissue are used. The reference genes employed in this experiment are also represented.

TABLE 21

Marker genes and reference genes for PCR validation

| Marker | Primer for qualitative PCR (SeqID) |
|---|---|
| CDKN1C SeqID 104 | reverse: 734 |
| CTSL SeqID 149 | forward: 735 reverse: 736 |
| METTL7B SeqID 145 | forward: 737 |

| Referenzgene | Primer for quantitative PCR (SeqID) |
|---|---|
| SNAPC SeqID 679 | forward: 727 reverse: 728 |
| CASP8 SeqID 681-686 | forward: 731 reverse: 732 |
| ITGAL SeqID 676, 677 | forward: 725 reverse: 726 |

Experimental Execution

Blood Sampling and RNA Isolation:

The patient's full blood was taken at the intensive care unit by means of the PAXGene kit in accordance with the manufacturer's (Qiagen) specifications. Following sampling of the full blood, the total RNA of the samples was isolated by using the PAXGene Blood RNA kit in accordance with the manufacturer's (Qiagen) specifications.

Reverse Transcription:

From each patient sample 300 ng of the total RNA was transcribed to complementary DNA (cDNA) by the reverse transcriptase Superscript II (Invitrogen) in a 20-µl batch, and the RNA was then removed from the batch by alkaline hydrolysis. The reaction batches were subsequently purified with the aid of Microcon columns, Real-Time PCR The Platinum SYBR Green qPCR SuperMix-UDG kit by the company Invitrogen was used. For a 10-µl batch the following constituents were pipetted:

| | |
|---|---|
| 5 µl | Platinum SYBR Green qPCR Supermix-UDG, 2x |
| 1 µl | Primer forward (10 pmol/µl) |
| 1 µl | Primer reverse (10 pmol/µl) |
| 1 µl | Fluorescein (0.5 µM) |
| 1 µl | H₂O, Rnase-free |
| 1 µl | Template cDNA (6.67 ng/µl) |

The subsequent PCR program was constructed as follows:

| | |
|---|---|
| 50° C. | 2 min (incubation with Uracil-DNA glycosylase) |
| 95° C. | 2 min (activation of the polymerase) |
| 95° C. | 10 sec (denaturing) |
| 55° C. | 15 sec (annealing)   } 40 x |
| 72° C. | 20 sec (extension) |
| 50° C.-95° C. | 10 sec (drawing up the melting curve, raising the initial temperature by 1° C. after each step)   } 41 x |

The iQ™5 Multicolor Real-Time PCR Detection System by the company BIORAD with the associated evaluation software was used.

Results

The Ct values of the real-time PCR were normalized according to the method of Vandesompele [Vandesompele et al. 2002]. For the Vandesompele normalization, at first the relative quantity R is calculated for each target (Gene of Interest and reference gene):

$$R = E^{min(Ct)-Ct}$$

For the efficiency E the idealized value 2 is inserted. The efficiency is raised to the power of the difference from the smallest Ct value from all samples of a gene and the respective patient sample. The normalization factor NF is calculated via the geometric mean of the relative quantities R of the reference genes (Ref):

$$NF = \sqrt[3]{R_{Ref1} * R_{Ref2} * R_{Ref3}} \quad bzw. \quad NF = \sqrt[1]{R_{Ref1}} = R_{Ref1}$$

For the normalization factor, the third root is taken from the product of the three reference genes. In order to obtain the normalized data, the quotient of the relative quantity R and the normalization factor is formed:

$$Ct_{NormDataGOI} = \frac{R_{GOI}}{NF}$$

Figure 13:
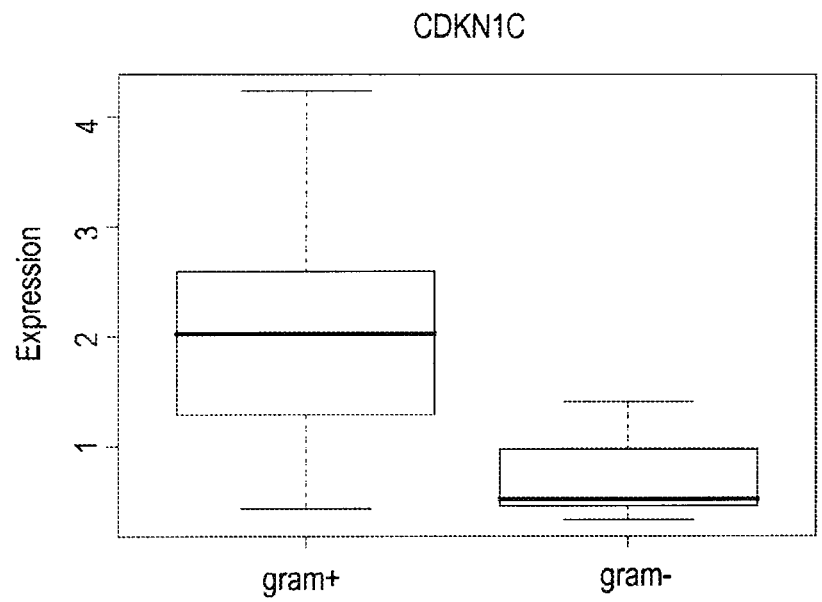
FIG. 13 shows a box plot of the normalized real-time PCR data for the biomarker candidates CDKN1C (SEQ ID NO: 104) for the differentiation of gram-positive and gram-negative infection.

In this context, FIG. 13 shows the differential expression of the gene CDKN1C in septic patients with gram-positive and gram-negative infection. In the box plot the mean normalized Ct values for 5 patients each are represented. These values were determined by real-time PCR on the patients' cDNA.

Figure 14:
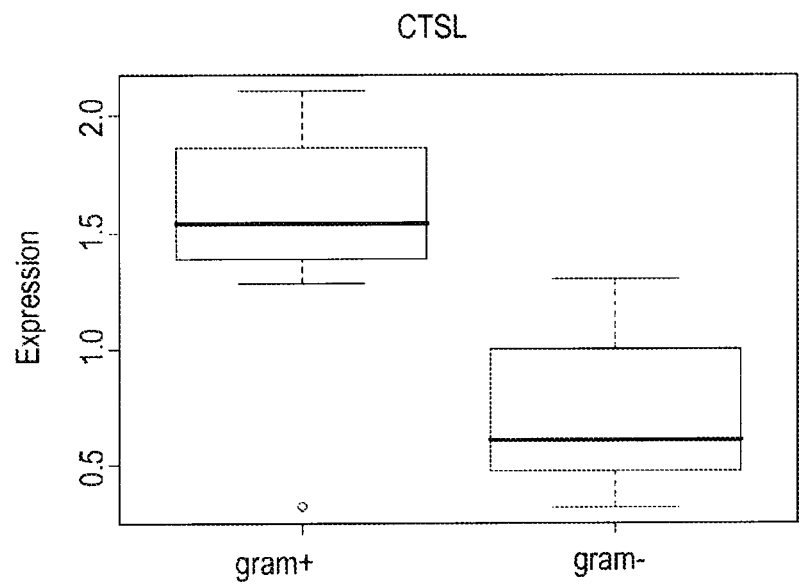
FIG. 14 shows a box plot of the normalized real-time PCR data for the biomarker CTSL for the differentiation of gram-positive and gram-negative infection.

FIG. 14 shows the differential expression of the gene CTSL in septic patients with gram-positive and gram-negative infection. In the box plot the mean normalized Ct values for 5 patients each are also represented. These values were determined by real-time PCR on the patients' cDNA.

Figure 15:
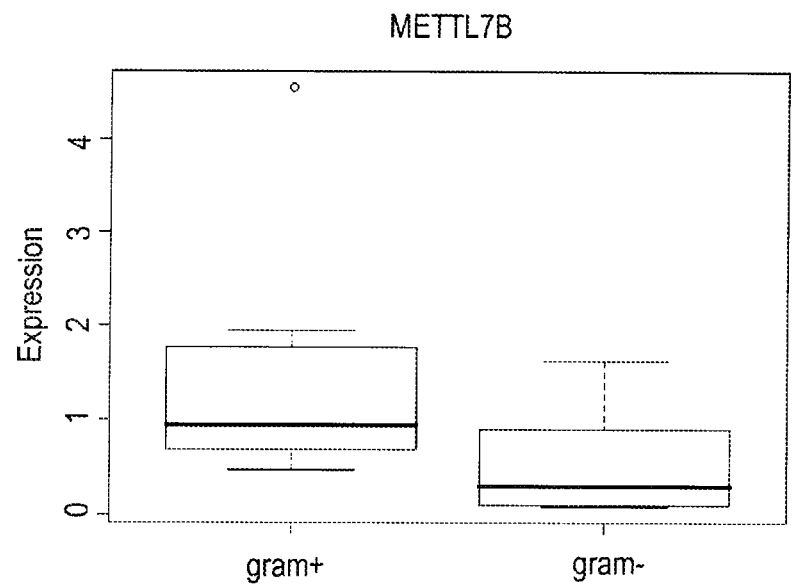
FIG. 15 shows a box plot of the normalized real-time PCR data for the biomarker candidate METTL7B (SEQ ID NO: 145) for the differentiation of gram-positive and gram-negative infection.

In FIG. 15 the differential expression of the gene METTL7B in septic patients with gram-positive and gram-negative infection is shown. In the box plot the mean normalized Ct values for 5 patients each are represented. These values were determined by real-time PCR on the patients' cDNA.

Table 22 shows raw data (Ct values, average values from triplicates) from the qPCR assays for the marker CDKN1C (SeqID 104).

Table 23 contains raw data from the qPCR assays normalized according to Vandesompele [Vandesompele et al., 2002] for the marker CDKN1C (SeqID 104).

Table 24 contains raw data (Ct values, average values from triplicates) from the gPCR assays for the marker CTSL (SeqID 149).

Table 25 shows raw data from the qPCR assays normalized according to Vandesompele [Vandesompele et al., 2002] for the marker CTSL (SeqID 149).

Table 26 contains raw data (Ct values, average values from triplicates) from the qPCR assays for the marker METTL7B (SeqID 145).

Table 27 shows raw data normalized in accordance with Vandesompele [Vandesompele et al., 2002] from the gPCR assays for the marker METTL7B (SeqID 145).

TABLE 22

Raw data (Ct values, mean values) from the qPCR assays for the marker CDKN1C (SeqID 104). Light grey: patients with gram-negative infection; dark grey: Patients with gram-positive infection.

| Patient | SeqID 104 | ITGAL (ref. gene, SeqID 676, 677) | CASP8 (ref. gene, SeqIDs 681, 682, 683 684, 685, 686) | SNAPC (ref. gene, SeqID 679) |
|---|---|---|---|---|
| 6047.003 | 31.24 | 25.97 | 27.62 | 31.79 |
| 7120.005 | 30.92 | 23.81 | 25.69 | 30.1 |
| 6058.001 | 30.31 | 23.54 | 24.2 | 28.64 |
| 6104.001 | 30.87 | 24.55 | 26.15 | 29.24 |
| 7023.001 | 28.81 | 25.34 | 26.83 | 30.7 |
| 1015.002 | 29.73 | 25.35 | 26.88 | 30.22 |
| 7040.001 | 29.47 | 25.33 | 26.88 | 30.38 |
| 6103.001 | 28.73 | 23.58 | 25.74 | 29.06 |
| 6070.002 | 30.44 | 25.93 | 28.3 | 31.55 |

TABLE 23

Raw data normalized in accordance with Vandesompele from the qPCR assays for the marker CDKN1C (SeqID 104). Light grey: patients with gram-negative infection; dark grey: patients with gram-positive infection.

| Patient | Seq ID 104 | ITGAL (ref. gene, SeqID 95) | CASP8 (ref. gene, SeqIDs 680, 681, 682 683, 684, 685) | SNAPC (ref. gene, SeqID 678) |
|---|---|---|---|---|
| 6047.003 | 1.404444876 | 1.484523571 | 0.747424624 | 0.901250463 |
| 7120.005 | 0.461158097 | 1.745128575 | 0.749153538 | 0.764894847 |
| 6058.001 | 0.334481889 | 1 | 1 | 1 |
| 6104.001 | 0.516437858 | 1.130269389 | 0.589133569 | 1.501772904 |
| 7023.001 | 4.237852377 | 1.286394669 | 0.723634619 | 1.074252648 |
| 1015.002 | 2.032609864 | 1.159363791 | 0.634342247 | 1.359742373 |
| 7040.001 | 2.514026749 | 1.214194884 | 0.655196702 | 1.257013375 |
| 6103.001 | 1.587401052 | 1.543993487 | 0.545884132 | 1.186462635 |
| 6070.002 | 2.682044796 | 1.674039226 | 0.511686946 | 1.167427804 |

TABLE 24

Raw data (Ct values, mean values) from the qPCR assays for the marker CTSL (SeqID 149). Light grey: patients with gram-negative infection; dark grey: patients with gram-positive infection.

| Patient | SeqID 149 | ITGAL (ref. gene, SeqID 676, 677) | CASP8 (ref. gene, SeqIDs 681, 682, 683 684, 685, 686) | SNAPC (ref. gene, SeqID 679) |
|---|---|---|---|---|
| 6047.003 |  | 25.97 | 27.62 | 31.79 |
| 7120.005 | 29.33 | 23.81 | 25.69 | 30.1 |
| 6058.001 | 27.53 | 23.54 | 24.2 | 28.64 |
| 6104.001 | 29.8 | 24.55 | 26.15 | 29.24 |
| 7023.001 | 28.62 | 25.34 | 26.83 | 30.7 |
| 1015.002 | 28.65 | 25.35 | 26.88 | 30.22 |
| 7040.001 | 28.71 | 25.33 | 26.88 | 30.38 |
| 6103.001 | 27.62 | 23.58 | 25.74 | 29.06 |
| 6070.002 | 30.04 | 25.93 | 28.3 | 31.55 |

TABLE 25

Raw data normalized in accordance with Vandesompele from the qPCR assays for the marker CTSL (SeqID 149). Light grey: patients with gram-negative infection; dark grey: patients with gram-positive infection.

| Patient | SeqID 149 | ITGAL (ref. gene, SeqID 676, 677) | CASP8 (ref. gene, SeqIDs 681, 682, 683 684, 685, 686) | SNAPC (ref. gene, SeqID 679) |
|---|---|---|---|---|
| 6047.003 | 1.301341855 | 1.484523571 | 0.747424624 | 0.901250463 |
| 7120.005 | 0.604298528 | 1.745128575 | 0.749153538 | 0.764894847 |
| 6058.001 | 1 | 1 | 1 | 1 |
| 6104.001 | 0.471937156 | 1.130269389 | 0.589133569 | 1.501772904 |
| 7023.001 | 2.104329696 | 1.286394669 | 0.723634619 | 1.074252648 |
| 1015.002 | 1.870382496 | 1.159363791 | 0.634342247 | 1.359742373 |
| 7040.001 | 1.853176124 | 1.214194884 | 0.655196702 | 1.257013375 |
| 6103.001 | 1.4913994 | 1.543993487 | 0.545884132 | 1.186462635 |
| 6070.002 | 1.540430222 | 1.674039226 | 0.511686946 | 1.167427804 |

TABLE 26

Raw data (Ct values, mean values) from the qPCR assays for the marker METTL7B (SeqID 145). Light grey: patients with gram-negative infection; dark grey: Patients with gram-positive infection.

| Patient | SeqID 145 | ITGAL (ref. gene, SeqID 676, 677) | CASP8 (ref. gene, SeqIDs 681, 682, 683 684, 685, 686) | SNAPC (ref. gene, SeqID 679) |
|---|---|---|---|---|
| 6047.003 | 29.8 | 25.97 | 27.62 | 31.79 |
| 7120.005 | 31.25 | 23.81 | 25.69 | 30.1 |
| 6058.001 | 29.96 | 23.54 | 24.2 | 28.64 |
| 6104.001 | 29.6 | 24.55 | 26.15 | 29.24 |
| 7023.001 | 28.88 | 25.34 | 26.83 | 30.7 |
| 1015.002 | 27.71 | 25.35 | 26.88 | 30.22 |
| 7040.001 | 29.35 | 25.33 | 26.88 | 30.38 |
| 6103.001 | 26.65 | 23.58 | 25.74 | 29.06 |
| 6070.002 | 27.6 | 25.93 | 28.3 | 31.55 |

TABLE 27

Raw data from the qPCR assays normalized in accordance with Vandesompele for the marker METTL7B (SeqID 145). Light grey: patients with gram-negative infection; dark grey: patients with gram-positive infection.

| Patient | SeqID 145 | ITGAL (ref. gene, SeqID 676, 677) | CASP8 (ref. gene, SeqIDs 681, 682, 683 684, 685, 686) | SNAPC (ref. gene, SeqID 679) |
|---|---|---|---|---|
| 6047.003 | 0.901250463 | 1.484523571 | 0.747424624 | 0.901250463 |
| 7120.005 | 0.086769591 | 1.745128575 | 0.749153538 | 0.764894847 |
| 6058.001 | 0.10083022 | 1 | 1 | 1 |
| 6104.001 | 0.294566785 | 1.130269389 | 0.589133569 | 1.501772904 |
| 7023.001 | 0.954841604 | 1.286394669 | 0.723634619 | 1.074252648 |
| 1015.002 | 1.949809711 | 1.159363791 | 0.634342247 | 1.359742373 |
| 7040.001 | 0.646176415 | 1.214194884 | 0.655196702 | 1.257013375 |
| 6103.001 | 1.587401052 | 1.543993487 | 0.545884132 | 1.186462635 |
| 6070.002 | 4.542017716 | 1.674039226 | 0.511686946 | 1.167427804 |

Significance of the Results

It was subsequently checked by the Wilcoxon test whether the results are significant. The proposed null hypothesis stated that there are no significant differences in the two groups with regard to gene expression. The null hypothesis could be disproven in all 3 targets. Thus, there is a 95-% probability that the difference between gram-positive and gram-negative septics with regard to the expression of CDKN1C(SeqID 104), CTSL (SeqID 149) and METTL7B (SeqID 145) is not accidental.

Fold Change

In order to compare the x-fold variation of a larger number of values among each other, at first the geometrical mean of each group was formed from the values normalized in accordance with Vandesompele. The fold change, or the x-fold variation of the gene expression is then calculated from the quotient of the Ct values normalized in accordance with Vandesompele of the groups to be compared. The efficiency of PCR was already included in the calculation during normalization, so that it is omitted at this stage.

The fold change of the patients is thus calculated as follows:

$$\text{Fold Change}_{GOI\ Gram+\ vs.\ Gram-} = \frac{geomean(Ct_{NormDataGOIGram+})}{geomean(Ct_{NormDataGOIGram-})}$$

In the PCR analysis, all three examined targets exhibited a fold change$_{Gram+ vs. Gram-}$ with the same tendency as in the microarray evaluation. Here it is conspicuous that the target METTL7B, which achieved the greatest fold change with Illumina, now also assumes the highest value in the PCR analysis.

Table 28 shows medical parameters of the patients contained in the analysis as validated on the hospital's part.

TABLE 28

Medical parameters of the patients contained in the analysis. Light grey: patients with gram-negative infection; dark grey: patients with gram-positive infection.

| | 6103.001 | 7023.001 | 7040.001 | 1015.002 | 6070.002 |
|---|---|---|---|---|---|
| Age [yrs] | 36 | 75 | 70 | 71 | — |
| Sex | male | male | male | male | male |
| Weight [kg] | 75 | 124 | 60 | 75 | 90 |
| Height [cm] | — | 178 | — | 171 | 183 |
| BMI | — | 39.1 | — | 25.6 | 26.9 |
| Admission date | May 21, 2004 | Nov. 9, 2004 | Nov. 6, 2004 | Nov. 2, 2002 | Nov. 3, 2003 |
| Sampling date | May 23, 2004 | Nov. 18, 2004 | Nov. 11m 2004 | Nov. 11, 2002 | Dec. 13, 2003 |
| ICU day | 3 | 9 | 2 | 2 | 3 |
| Quick (max) [%] | 91 | 97 | 56 | 67 | 89 |
| PTT (max) [s] | 43 | 55 | 50 | 58.8 | 35 |
| Fibrinogen (min) | — | 5.5 | 6.6 | 6.2 | — |
| ATIII (min) [%] | — | 60 | — | 52 | — |
| Thrombos [*10$^3$] (min) | 149 | 232 | 411 | 112 | 267 |
| Leukos | 8900 | 14200 | 28400 | 20100 | 10600 |
| CRP (max) [mg/l] | 343 | 124 | 304 | — | 404 |
| PCT (max) [ng/ml] | 0.65 | 0.3 | 13.5 | 5.12 | 2.31 |
| Lactate (max) [mmol/l] | 1.3 | 1.6 | 1.4 | 1.6 | 2.2 |
| Bilirubin total (max) [µmol/l] | 11 | 9 | 19 | 11.7 | 21 |
| Creatinine (max) [µmol/l] | 86 | 144 | 444 | 266 | 167 |
| Krea-Cl. (min) [µmol/l] | — | — | — | 38 | 47 |
| BE(min) [mmol/l] | 4 | 0 | −4.8 | −5.1 | −2.3 |
| Albumin (min) [mmol/l] | — | — | — | 13.1 | — |
| Temperature [° C.] | 39.7 | 38.7 | 38.6 | 39.8 | 37.5 |
| Heart rate [min$^{-1}$] | 107 | 110 | 110 | 119 | 134 |
| Respiratory frequency spont. [min$^{-1}$] | 18 | 22 | — | 17 | 12 |
| Arterial CO$_2$ [kP] | 5.23 | — | — | 4.59 | 4.58 |
| PaO$_2$ | — | — | — | — | 94 |
| PaO$_2$/FiO$_2$ | 133 | 106 | 173 | 194 | 147 |
| Diuresis [ml/24 h] | 3310 | 2346 | 0 | 2910 | 4125 |
| MAP [mmHg] | 69 | 56 | 62 | 56 | 66 |
| Discharge date | Jun. 3, 2004 | Jan. 9, 2005 | Dec. 30, 2004 | Dec. 12, 2002 | Jan. 21, 2004 |
| Discharge type | transfer | death | discharge | discharge | discharge |

| | 6104.001 | 7120.005 | 6058.001 | 6047.003 |
|---|---|---|---|---|
| Age [yrs] | 40 | 84 | 55 | 51 |
| Sex | female | female | female | male |
| Weight [kg] | 65 | — | 82 | 125 |
| Height [cm] | 168 | 170 | 170 | 191 |
| BMI | 23.0 | — | 28.4 | 34.3 |
| Admission date | Apr. 28, 2004 | Apr. 20, 2005 | Oct. 27, 2003 | Sep. 21, 2003 |
| Sampling date | May 25, 2004 | Apr. 26, 2005 | Nov. 7, 2003 | Sep. 27, 2003 |
| ICU day | 7 | 5 | 10 | 6 |
| Quick (max) [%] | 87 | 71 | 113 | 122 |
| PTT (max) [s] | 43 | 33 | 78.7 | 30.9 |
| Fibrinogen (min) | — | 3.9 | — | — |
| ATIII (min) [%] | — | — | — | — |
| Thrombos [*10$^3$] (min) | 342 | 190 | 214 | 143 |
| Leukos | 16700 | 21400 | 18000 | 6800 |
| CRP (max) [mg/l] | 250 | 50.8 | 64.3 | 161 |
| PCT (max) [ng/ml] | 38.7 | 3.99 | 1.57 | 5.61 |
| Lactate (max) [mmol/l] | 1.2 | 3.1 | 2.9 | 0.9 |
| Bilirubin total (max) [µmol/l] | 6 | 8 | 22 | 13.6 |
| Creatinine (max) [µmol/l] | 37 | 132 | 108 | 94 |
| Krea-Cl. (min) [µmol/l] | 111 | 14 | 52 | 127 |
| BE(min) [mmol/l] | 5.5 | 0.7 | 1.2 | 2.8 |
| Albumin (min) [mmol/l] | — | — | — | — |
| Temperature [° C.] | 37.9 | 37.5 | 37.8 | 38.1 |
| Heart rate [min$^{-1}$] | 122 | 141 | 116 | 115 |
| Respiratory frequency spont. [min$^{-1}$] | 32 | 23 | 23 | 27 |

TABLE 28-continued

| Arterial CO$_2$ [kP] | 5.04 | 5.5 | 3.99 | 5.18 |
|---|---|---|---|---|
| PaO$_2$ | 93 | — | — | — |
| PaO$_2$/FiO$_2$ | 198 | 129 | 148 | 211 |
| Diurese [ml/24 h] | 3550 | 1138 | 2290 | 3420 |
| MAP [mmHg] | 66 | 71 | 65 | 80 |
| Discharge date | Jun. 16, 2004 | May 3, 2005 | Dec. 9, 2003 | Oct. 7, 2003 |
| Discharge type | discharge | death | discharge | discharge |

Example 5

Non-Coding RNA—Differential Gene Expression of a Transcript without Protein-Coding Function (So-Called Non-Coding RNA) in SIRS and Sepsis Patients by Means of Real-Time PCR Measurement of the Gene Expression 5 patients with pneumonia were selected as sepsis representatives, and in the case of SIRS, 5 patients with major heart surgery (cardiopulmonal bypass, CPB), for these make up the majority of SIRS patients in an ICU (see Table 29). The patients were retrospectively validated in their diagnosis by a team of medical doctors of Jena university hospital.

Total RNA was isolated from the patients' blood and transcribed to cDNA. The latter was used in the assay as a template.

TABLE 29

List of examined patients

| Patient ID | Sepsis (pneumonia) | SIRS |
|---|---|---|
| 6032 | X | |
| 6048 | X | |
| 6063 | X | |
| 6070 | X | |
| 6104 | X | |
| 8002 | | X |
| 8026 | | X |
| 8086 | | X |
| 8102 | | X |
| 2038 | | X |

The marker having SegID 207 (Accession No. AA868082) for non-coding RNA is part of the list of biomarkers shown above.

Table 30 shows an example of a primer pair for the amplification of the non-coding marker having SeqID 207 in the real-time PCR. 10 patients were examined (5 sepsis patients, 5 SIRS patients).

TABLE 30

Exemplary primer pair for the quantitative PCR

| SeqID | Primer | |
|---|---|---|
| 207 | Forward | SeqID 739 |
| | Reverse | SeqID 740 |

Experimental Execution

Blood Sampling and RNA Isolation

The patient's full blood was taken at the intensive care unit by means of the PAXGene kit in accordance with the manufacturer's (Qiagen) specifications, and the RNA was isolated.

Reverse Transcription

From each patient sample, 4 µg of the total RNA was transcribed to complementary DNA (cDNA) by the reverse transcriptase Superscript II (Invitrogen) in a 20-µl batch (10 mM of dNTP mix and 2 µM of gene-specific primer (SeqID 207), and the RNA was then removed from the batch by alkaline hydrolysis. The reaction batches were purified with Microcon columns; the eluted cDNA was evaporated in the SpeedVac and subsequently received in 50 µl of water.

Real-Time PCR

The Platinum SYBR Green qPCR SuperMix-UDG kit by the company Invitrogen was used. The patient cDNA was diluted 1:100 with water, and 2 µl each of this was used for the PCR. All of the batches were pipetted in triplicate.

PCR batch pro well (10 µl):
2 µl template cDNA 1:100
1 µl forward primer, 10 mM
1 µl reverse primer, 10 mM
1 µl fluorescein reference dye
5 µl Platinum SYBR Green qPCR SuperMix-UDG, 2×

A mastermix without template was prepared, which was stepped in 8-µl aliquots in the PCR plate and to each of which the patient cDNAs were pipetted. The subsequent PCR program was constructed as follows:

| | | |
|---|---|---|
| 50° C. | 2 min (incubation with uracil-DNA-glykosylase) | |
| 95° C. | 2 min (activation of the polymerase) | |
| 95° C. | 10 sec (denaturing) | |
| 58° C. | 15 sec (annealing) | } 40 x |
| 72° C. | 20 sec (extension) | |
| 55° C.-95° C. | 10 sec (drawing up the melting curve, raising the intial temperature by 1° C. after each step) | } 41 x |

The iQ™5 Multicolor Real-Rime PCR Detection System by the company BIORAD with the associated evaluation software was used.

Results

The expression signals measured by means of Real-Time assays were stored in the Excel format and averaged via the triple determinations. The results are shown in the following Table 31.

TABLE 31

Ct values from the real-time assays

| Patient ID | Ct values (mean values) |
|---|---|
| 6032 | 22.33 |
| 6048 | 22.62 |
| 6063 | 20.99 |
| 6070 | 26.82 |
| 6104 | 22.59 |
| 8002 | 23.92 |
| 8026 | 23.28 |
| 8086 | 23.18 |
| 8102 | 23.95 |
| 2038 | 22.93 |

Figure 16:
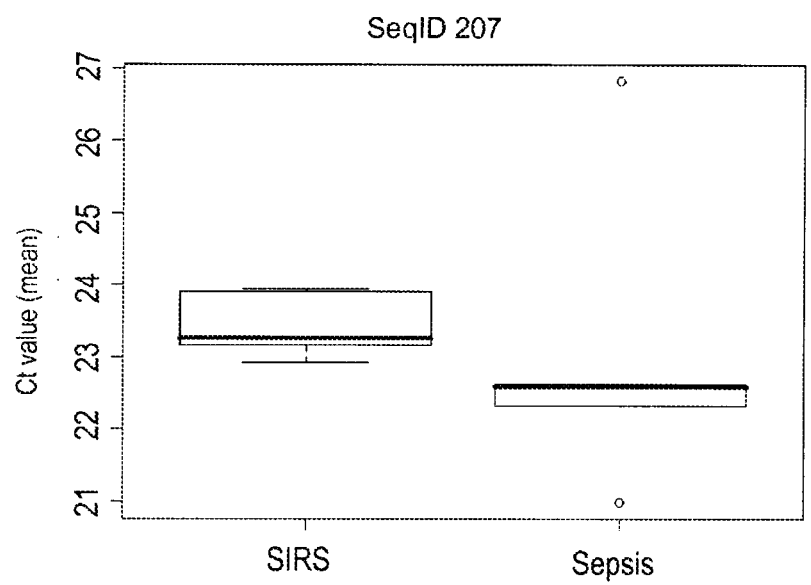
FIG. 16 shows a box plot for the non-coding marker having SEQ ID NO: 207; on the y-axis, the mean Ct value during real-time amplification is represented.

FIG. 16 shows a box plot for the non-coding marker having SeqID 207, produced from 10 patient samples (5 with diagnosed sepsis, 5 with SIRS). On the y-axis the mean Ct value during real-time amplification is represented. A clear separation of sepsis and SIRS patients is discernible.

The following Table 32 establishes the relationship between the sequence protocol number of the single polynucleotides and their publicly accessible accession number.

TABLE 32

Correlation of sequence number (sequence protocol) and accession number

| SeqID | AccessionNo |
| --- | --- |
| 1 | NM_130850 |
| 2 | NM_130851 |
| 3 | NM_001202 |
| 4 | NM_001795 |
| 5 | NM_001114117 |
| 6 | NM_001817 |
| 7 | NM_002116 |
| 8 | NM_002989 |
| 9 | NM_003151 |
| 10 | NM_004064 |
| 11 | NM_005419 |
| 12 | NM_017455 |
| 13 | NM_012428 |
| 14 | NM_003136 |
| 15 | NM_004402 |
| 16 | NM_002947 |
| 17 | NM_198256 |
| 18 | NM_005923 |
| 19 | NM_002758 |
| 20 | NM_002389 |
| 21 | NM_153826 |
| 22 | NM_172350 |
| 23 | NM_172351 |
| 24 | NM_172352 |
| 25 | NM_172353 |
| 26 | NM_172354 |
| 27 | NM_172355 |
| 28 | NM_172356 |
| 29 | NM_172357 |
| 30 | NM_172358 |
| 31 | NM_172359 |
| 32 | NM_172360 |
| 33 | NM_172361 |
| 34 | NM_002163 |
| 35 | NM_002200 |
| 36 | NM_032643 |
| 37 | NM_001098627 |
| 38 | NM_001098628 |
| 39 | NM_001098629 |
| 40 | NM_001098630 |
| 41 | NM_001098631 |
| 42 | NM_015093 |
| 43 | NM_000331 |
| 44 | NM_199161 |
| 45 | NM_000364 |
| 46 | NM_001001430 |
| 47 | NM_001001431 |
| 48 | NM_001001432 |
| 49 | NM_000258 |
| 50 | NM_003376 |
| 51 | NM_001033756 |
| 52 | NM_001025366 |
| 53 | NM_001025367 |
| 54 | NM_001025368 |
| 55 | NM_001025369 |
| 56 | NM_001025370 |
| 57 | NM_002872 |
| 58 | NM_006094 |
| 59 | NM_182643 |
| 60 | NM_016142 |
| 61 | NM_014887 |
| 62 | NM_033111 |
| 63 | NM_001076786 |
| 64 | NM_001085377 |
| 65 | NM_002387 |
| 66 | NM_001938 |
| 67 | NM_207436 |
| 68 | NM_012264 |
| 69 | NM_033423 |
| 70 | AI873192 |
| 71 | NM_003272 |
| 72 | DA920728 |
| 73 | AA454562 |
| 74 | NM_004992 |
| 75 | NM_001110792 |
| 76 | BF057027 |
| 77 | NM_033200 |
| 78 | NM_002218 |
| 79 | NM_000240 |
| 80 | NM_003000 |
| 81 | NM_004924 |
| 82 | AW025248 |
| 83 | NM_138781 |
| 84 | NM_181722 |
| 85 | NM_000505 |
| 86 | NM_004755 |
| 87 | NM_001493 |
| 88 | NM_030629 |
| 89 | NM_015378 |
| 90 | NM_002306 |
| 91 | NM_152485 |
| 92 | NM_004681 |
| 93 | NM_013363 |
| 94 | NM_032152 |
| 95 | NM_016619 |
| 96 | NM_024897 |
| 97 | NM_017668 |
| 98 | NM_004618 |
| 99 | NM_000045 |
| 100 | NM_006498 |
| 101 | NM_005332 |
| 102 | NM_000784 |
| 103 | NM_002759 |
| 104 | NM_000076 |
| 105 | NM_020310 |
| 106 | NM_199072 |
| 107 | NM_006060 |
| 108 | NM_015179 |
| 109 | NM_001002 |
| 110 | NM_015225 |
| 111 | NM_001453 |
| 112 | NM_152280 |
| 113 | NM_022355 |
| 114 | NM_003596 |
| 115 | NM_021991 |
| 116 | NM_020354 |
| 117 | NM_004624 |
| 118 | NM_006048 |
| 119 | NM_014640 |
| 120 | NM_033211 |
| 121 | NM_002053 |
| 122 | NM_024910 |
| 123 | NM_025182 |
| 124 | NM_004422 |
| 125 | NM_004653 |
| 126 | NM_020196 |
| 127 | NM_181724 |
| 128 | NM_007067 |
| 129 | NM_015345 |
| 130 | BM822150 |
| 131 | BX110982 |
| 132 | BI830161 |
| 133 | NM_015987 |
| 134 | NM_001023560 |
| 135 | NM_018028 |
| 136 | NM_020683 |
| 137 | NM_024660 |
| 138 | NM_003283 |
| 139 | NM_152742 |

TABLE 32-continued

Correlation of sequence number (sequence protocol) and accession number

| SeqID | AccessionNo |
|---|---|
| 140 | NM_001007595 |
| 141 | NM_018324 |
| 142 | NM_002193 |
| 143 | NM_018664 |
| 144 | BX099079 |
| 145 | NM_152637 |
| 146 | NM_002714 |
| 147 | NM_001008 |
| 148 | NM_006451 |
| 149 | NM_145918 |
| 150 | AF086272 |
| 151 | NM_020775 |
| 152 | NM_016151 |
| 153 | NM_004519 |
| 154 | NM_153029 |
| 155 | NM_016396 |
| 156 | NM_003743 |
| 157 | NM_147223 |
| 158 | NM_147233 |
| 159 | AA029887 |
| 160 | AA035428 |
| 161 | NM_020808 |
| 162 | NM_012383 |
| 163 | NM_001042780 |
| 164 | NM_006757 |
| 165 | NM_001042781 |
| 166 | NM_001042782 |
| 167 | NM_002727 |
| 168 | NM_012081 |
| 169 | NM_006806 |
| 170 | AA398757 |
| 171 | NM_004273 |
| 172 | NM_018555 |
| 173 | NM_001079906 |
| 174 | NM_001079907 |
| 175 | AA412166 |
| 176 | AA417348 |
| 177 | AA417792 |
| 178 | NM_001512 |
| 179 | NM_018412 |
| 180 | NM_021908 |
| 181 | NM_015447 |
| 182 | NM_015094 |
| 183 | NM_181806 |
| 184 | AA453996 |
| 185 | NM_003828 |
| 186 | NM_005999 |
| 187 | NM_032270 |
| 188 | NM_018475 |
| 189 | AA493225 |
| 190 | AA495787 |
| 191 | NM_172127 |
| 192 | NM_172128 |
| 193 | NM_001221 |
| 194 | NM_172115 |
| 195 | NM_144607 |
| 196 | BX647243 |
| 197 | AA682790 |
| 198 | NM_014982 |
| 199 | NM_005688 |
| 200 | AA708806 |
| 201 | NM_002006 |
| 202 | NM_005500 |
| 203 | AA812763 |
| 204 | AA825968 |
| 205 | AA833528 |
| 206 | NM_145039 |
| 207 | AA868082 |
| 208 | NM_003357 |
| 209 | NM_001025468 |
| 210 | NM_002405 |
| 211 | AA923169 |
| 212 | AA923246 |
| 213 | AA947111 |
| 214 | NM_014714 |
| 215 | NM_001012706 |
| 216 | AI003843 |
| 217 | NM_003747 |
| 218 | AI041544 |
| 219 | NM_003485 |
| 220 | NM_182536 |
| 221 | NM_014478 |
| 222 | NM_001040647 |
| 223 | NM_001040648 |
| 224 | AI149693 |
| 225 | NM_005220 |
| 226 | NM_018053 |
| 227 | NM_001055 |
| 228 | NM_177529 |
| 229 | NM_177530 |
| 230 | NM_177534 |
| 231 | NM_177536 |
| 232 | AI214494 |
| 233 | AI217376 |
| 234 | AI218498 |
| 235 | AI221860 |
| 236 | AI224886 |
| 237 | NM_014798 |
| 238 | NM_173607 |
| 239 | NM_001079519 |
| 240 | NM_001553 |
| 241 | AI273261 |
| 242 | AI281098 |
| 243 | AI343613 |
| 244 | NM_001015072 |
| 245 | AI364529 |
| 246 | NM_016073 |
| 247 | NM_203402 |
| 248 | NM_015026 |
| 249 | NM_016376 |
| 250 | NM_020740 |
| 251 | NM_022458 |
| 252 | AI539445 |
| 253 | NR_002768 |
| 254 | AI554111 |
| 255 | NM_003627 |
| 256 | NM_000135 |
| 257 | NM_001018112 |
| 258 | NM_018725 |
| 259 | CR936786 |
| 260 | AI613016 |
| 261 | AI623567 |
| 262 | NM_001114086 |
| 263 | NM_001042552 |
| 264 | NM_001042553 |
| 265 | NM_181844 |
| 266 | AI675585 |
| 267 | NM_198524 |
| 268 | NM_018034 |
| 269 | AI732517 |
| 270 | NM_001080450 |
| 271 | BC015667 |
| 272 | NM_016335 |
| 273 | NM_031953 |
| 274 | NM_013233 |
| 275 | NM_080927 |
| 276 | NM_032383 |
| 277 | NM_031922 |
| 278 | NM_014801 |
| 279 | NM_152680 |
| 280 | NM_025209 |
| 281 | NM_017805 |
| 282 | AI811413 |
| 283 | AI820576 |
| 284 | AI821631 |
| 285 | NM_004145 |
| 286 | NM_004972 |
| 287 | AI888493 |
| 288 | NM_145294 |
| 289 | NM_012316 |

TABLE 32-continued

Correlation of sequence number (sequence protocol) and accession number

| SeqID | AccessionNo |
|---|---|
| 290 | NM_182491 |
| 291 | NM_001679 |
| 292 | NM_016270 |
| 293 | NM_018351 |
| 294 | NM_138775 |
| 295 | NM_004411 |
| 296 | NM_024893 |
| 297 | NM_020818 |
| 298 | H16790 |
| 299 | NM_203487 |
| 300 | NM_020403 |
| 301 | H18649 |
| 302 | NM_000526 |
| 303 | NM_002697 |
| 304 | NM_058182 |
| 305 | NM_002125 |
| 306 | H65331 |
| 307 | NM_017893 |
| 308 | NM_032112 |
| 309 | NM_176792 |
| 310 | NM_176793 |
| 311 | NM_176794 |
| 312 | NM_199189 |
| 313 | NM_018834 |
| 314 | H91663 |
| 315 | XM_001126561 |
| 316 | AL359596 |
| 317 | NM_023929 |
| 318 | NM_001105539 |
| 319 | NM_183421 |
| 320 | NM_183420 |
| 321 | NM_012173 |
| 322 | NM_022455 |
| 323 | NM_172349 |
| 324 | NM_000846 |
| 325 | NM_024790 |
| 326 | NM_001077204 |
| 327 | NM_007011 |
| 328 | NM_152924 |
| 329 | NM_022353 |
| 330 | NM_000028 |
| 331 | NM_000642 |
| 332 | NM_000643 |
| 333 | NM_000644 |
| 334 | NM_000645 |
| 335 | NM_000646 |
| 336 | NM_032663 |
| 337 | R12411 |
| 338 | NM_018376 |
| 339 | NM_004645 |
| 340 | NM_014155 |
| 341 | NM_017933 |
| 342 | NM_001100818 |
| 343 | NM_020777 |
| 344 | NM_005870 |
| 345 | NM_144609 |
| 346 | NM_001099225 |
| 347 | NM_016157 |
| 348 | NM_177556 |
| 349 | NM_001039705 |
| 350 | R43301 |
| 351 | NM_134261 |
| 352 | NM_134260 |
| 353 | NM_002943 |
| 354 | NM_134262 |
| 355 | CR613944 |
| 356 | NM_024034 |
| 357 | NM_020882 |
| 358 | AK091100 |
| 359 | NM_024306 |
| 360 | NM_032883 |
| 361 | NM_001098796 |
| 362 | NM_001098797 |
| 363 | NM_001098798 |
| 364 | NM_005151 |
| 365 | NM_001037334 |
| 366 | NM_173666 |
| 367 | NM_004826 |
| 368 | NM_053025 |
| 369 | NM_053026 |
| 370 | NM_053027 |
| 371 | NM_053028 |
| 372 | NM_053031 |
| 373 | NM_053032 |
| 374 | R70541 |
| 375 | NM_002461 |
| 376 | NM_182557 |
| 377 | NM_144604 |
| 378 | NM_013374 |
| 379 | R94894 |
| 380 | NM_021096 |
| 381 | NM_001003406 |
| 382 | NM_000245 |
| 383 | NM_017799 |
| 384 | T78484 |
| 385 | NM_013305 |
| 386 | NM_014932 |
| 387 | NM_153334 |
| 388 | NM_182895 |
| 389 | NM_138278 |
| 390 | NM_024721 |
| 391 | NM_003188 |
| 392 | NM_145331 |
| 393 | NM_145332 |
| 394 | NM_145333 |
| 395 | NM_004357 |
| 396 | NM_139029 |
| 397 | NM_139030 |
| 398 | NM_001039490 |
| 399 | NM_002746 |
| 400 | NM_001040056 |
| 401 | BC018761 |
| 402 | NM_001296 |
| 403 | NM_022117 |
| 404 | NM_017442 |
| 405 | NM_001199 |
| 406 | NM_006128 |
| 407 | NM_006129 |
| 408 | NM_000757 |
| 409 | NM_172210 |
| 410 | NM_172211 |
| 411 | NM_172212 |
| 412 | M37435 |
| 413 | NM_000574 |
| 414 | NM_001114544 |
| 415 | NM_001114543 |
| 416 | NM_001114752 |
| 417 | NM_000963 |
| 418 | NM_001288 |
| 419 | NM_001511 |
| 420 | NM_001530 |
| 421 | NM_181054 |
| 422 | NM_001560 |
| 423 | NM_001766 |
| 424 | NM_002128 |
| 425 | NM_024817 |
| 426 | NM_002133 |
| 427 | NM_002211 |
| 428 | NM_032571 |
| 429 | NM_002468 |
| 430 | NM_002649 |
| 431 | NM_003268 |
| 432 | NM_004049 |
| 433 | NM_004347 |
| 434 | NM_078471 |
| 435 | NM_203318 |
| 436 | NM_005803 |
| 437 | NM_006016 |
| 438 | NM_177551 |
| 439 | NM_006018 |

TABLE 32-continued

Correlation of sequence number (sequence protocol) and accession number

| SeqID | AccessionNo |
|---|---|
| 440 | NM_006058 |
| 441 | NM_006206 |
| 442 | NM_006378 |
| 443 | NM_000902 |
| 444 | NM_007287 |
| 445 | NM_007288 |
| 446 | NM_007289 |
| 447 | NM_002259 |
| 448 | NM_007328 |
| 449 | NM_213657 |
| 450 | NM_213658 |
| 451 | NM_012340 |
| 452 | NM_173091 |
| 453 | NM_013230 |
| 454 | NM_018643 |
| 455 | NM_022162 |
| 456 | NM_002750 |
| 457 | NM_139046 |
| 458 | NM_139047 |
| 459 | NM_139049 |
| 460 | NM_006887 |
| 461 | NM_014330 |
| 462 | NM_001025159 |
| 463 | NM_004355 |
| 464 | NM_001025158 |
| 465 | NM_004330 |
| 466 | NM_000687 |
| 467 | NM_000576 |
| 468 | NM_005389 |
| 469 | NM_004071 |
| 470 | NM_002231 |
| 471 | NM_001024844 |
| 472 | NM_000211 |
| 473 | NM_001001323 |
| 474 | NM_001682 |
| 475 | NM_001946 |
| 476 | NM_022652 |
| 477 | NM_001803 |
| 478 | NM_000194 |
| 479 | NM_003897 |
| 480 | NM_002262 |
| 481 | NM_007334 |
| 482 | NM_001114396 |
| 483 | NM_004006 |
| 484 | NM_000109 |
| 485 | NM_004010 |
| 486 | NM_004009 |
| 487 | NM_004007 |
| 488 | NM_004011 |
| 489 | NM_004012 |
| 490 | NM_004021 |
| 491 | NM_004022 |
| 492 | NM_004023 |
| 493 | NM_004013 |
| 494 | NM_004020 |
| 495 | NM_004014 |
| 496 | NM_004015 |
| 497 | NM_004016 |
| 498 | NM_004017 |
| 499 | NM_004018 |
| 500 | NM_004019 |
| 501 | NM_000698 |
| 502 | NM_020070 |
| 503 | NM_152855 |
| 504 | NM_005587 |
| 505 | NM_004131 |
| 506 | NM_001664 |
| 507 | NM_003701 |
| 508 | NM_033012 |
| 509 | NM_172089 |
| 510 | NM_003808 |
| 511 | NM_172087 |
| 512 | NM_172088 |
| 513 | NM_004938 |
| 514 | NM_003824 |
| 515 | NM_003842 |
| 516 | NM_147187 |
| 517 | NM_001244 |
| 518 | NM_006291 |
| 519 | NM_001924 |
| 520 | NM_003807 |
| 521 | NM_172014 |
| 522 | NM_033292 |
| 523 | NM_001223 |
| 524 | NM_033293 |
| 525 | NM_033294 |
| 526 | NM_033295 |
| 527 | NM_003580 |
| 528 | NM_003358 |
| 529 | NM_000648 |
| 530 | NM_000647 |
| 531 | NM_001337 |
| 532 | NM_006664 |
| 533 | NM_006072 |
| 534 | NM_002984 |
| 535 | NM_002985 |
| 536 | NM_006274 |
| 537 | NM_138284 |
| 538 | NM_000565 |
| 539 | NM_181359 |
| 540 | NM_003855 |
| 541 | NM_002185 |
| 542 | NM_173842 |
| 543 | NM_173841 |
| 544 | NM_000577 |
| 545 | NM_173843 |
| 546 | NM_000206 |
| 547 | NM_001558 |
| 548 | NM_000878 |
| 549 | NM_002175 |
| 550 | NM_002173 |
| 551 | NM_002172 |
| 552 | NM_003954 |
| 553 | NM_003010 |
| 554 | NM_002754 |
| 555 | NM_005922 |
| 556 | NM_006724 |
| 557 | NM_139033 |
| 558 | NM_139032 |
| 559 | NM_002749 |
| 560 | NM_139034 |
| 561 | NM_006301 |
| 562 | NM_005204 |
| 563 | NM_002755 |
| 564 | NM_006049 |
| 565 | NM_004180 |
| 566 | NM_001504 |
| 567 | NM_015991 |
| 568 | NM_031910 |
| 569 | NM_182486 |
| 570 | NM_000066 |
| 571 | NM_203330 |
| 572 | NM_000611 |
| 573 | NM_203329 |
| 574 | NM_203331 |
| 575 | NM_001831 |
| 576 | NM_203339 |
| 577 | NM_139208 |
| 578 | NM_006610 |
| 579 | NM_005041 |
| 580 | NM_001083116 |
| 581 | NM_005252 |
| 582 | NM_002199 |
| 583 | NM_001001349 |
| 584 | NM_017595 |
| 585 | NM_013432 |
| 586 | NM_002720 |
| 587 | NM_000594 |
| 588 | NM_014959 |
| 589 | NM_170707 |

TABLE 32-continued

Correlation of sequence number (sequence protocol) and accession number

| SeqID | AccessionNo |
|---|---|
| 590 | NM_005572 |
| 591 | NM_170708 |
| 592 | NM_000660 |
| 593 | NM_006238 |
| 594 | NM_000308 |
| 595 | NM_000397 |
| 596 | NM_000906 |
| 597 | NM_004475 |
| 598 | NM_006260 |
| 599 | NM_006597 |
| 600 | NM_153201 |
| 601 | NM_000714 |
| 602 | NM_007311 |
| 603 | NM_002059 |
| 604 | NM_022557 |
| 605 | NM_022558 |
| 606 | NM_022556 |
| 607 | NM_024302 |
| 608 | NM_001032278 |
| 609 | NM_152557 |
| 610 | NM_014858 |
| 611 | NM_016613 |
| 612 | NM_001031700 |
| 613 | NM_033554 |
| 614 | NM_006516 |
| 615 | NM_006682 |
| 616 | NM_005962 |
| 617 | NM_130439 |
| 618 | NM_001008541 |
| 619 | NM_031311 |
| 620 | NM_019029 |
| 621 | NM_002483 |
| 622 | BC012159 |
| 623 | NM_006936 |
| 624 | NM_001671 |
| 625 | XM_928029 |
| 626 | NM_002923 |
| 627 | NM_016068 |
| 628 | NM_003974 |
| 629 | NM_003258 |
| 630 | NM_001972 |
| 631 | AB288083 |
| 632 | EF492673 |
| 633 | M20813 |
| 634 | NM_001911 |
| 635 | NM_000291 |
| 636 | NM_004969 |
| 637 | NM_022442 |
| 638 | NM_021988 |
| 639 | NM_001032288 |
| 640 | NM_199144 |
| 641 | NM_003349 |
| 642 | NM_199203 |
| 643 | AI623897 |
| 644 | AK125136 |
| 645 | NM_005909 |
| 646 | NM_015320 |
| 647 | NM_032995 |
| 648 | NM_001031715 |
| 649 | NM_022784 |
| 650 | NM_005720 |
| 651 | NM_005647 |
| 652 | NM_005578 |
| 653 | NM_001002259 |
| 654 | NM_023925 |
| 655 | NM_032156 |
| 656 | NM_014781 |
| 657 | NM_001083617 |
| 658 | NR_003950 |
| 659 | NM_030799 |
| 660 | NM_001024947 |
| 661 | H06263 |
| 662 | NM_002103 |
| 663 | NM_002430 |
| 664 | NM_032173 |
| 665 | NM_153240 |
| 666 | W04695 |
| 667 | NM_145716 |
| 668 | NM_018070 |
| 669 | NM_001009955 |
| 670 | NM_001101 |
| 671 | NM_001084819 |
| 672 | NM_002046 |
| 673 | NM_000570 |
| 674 | NM_002123 |
| 675 | NR_003286 |
| 676 | NM_002209 |
| 677 | NM_001114380 |
| 678 | NM_021009 |
| 679 | NM_003082 |
| 680 | NM_001562 |
| 681 | NM_001228 |
| 682 | NM_033355 |
| 683 | NM_033356 |
| 684 | NM_001080124 |
| 685 | NM_033358 |
| 686 | NM_001080125 |

LITERATURE

ACCP/SCCM (1992), Crit. Care Med 20, 864-74

Alberti C, Brun-Buisson C, Goodman S V, Guidici D, Granton J, Moreno R, Smithies M, Thomas O, Artigas A, Le Gall J R; European Sepsis Group (2003) Influence of systemic inflammatory response syndrome and Sepsis on outcome of critically ill infected patients. Am J Respir Crit Care Med 168, 77-84.

Amin K, Kauffman C A (2003), Fever of unknown origin. Postgrad med 114(3), 69-75

Baker S G, and Kramer B (2006), Identifying genes that contribute most to good classification in microarray. BMC Bioinformatics 7, 407

Bone R C, Balk R A, Cerra F B, Dellinger E P, Fein A M, Knaus W A, Schein R M, Sibbald W J, the ACCP/SCCM Consensus Conference Committee (1992) Definitions for Sepsis and organ failure and guidelines for the use of innovative therapies in Sepsis. Chest 101, 1656-1662

Box G E P, Cox D R (1964) An analysis of transformations (with discussion). J Roy Stat Soc B 26, 211-252

Buneβ A, Huber W, Steiner K, Sültmann H, Poustka A (2005) ArrayMagic: two-colour cDNA microarray quality control and preprocessing. Bioinformatics 21, 554-556.

Breiman L (2001) Random Forests. Machine Learning 45(1), 5-32

Brun-Buisson C, Doyon F, Carlet J, Dellamonica P, Gouin F, Lepoutre A, Mercier J C, Offenstadt G, Regnier B (1995) Incidence, risk factors, and outcome of severe Sepsis and septic shock in adults. A multicenter prospective study in intensive care units. French ICU Group for Severe Sepsis. JAMA 274, 968-974

Brun-Buisson C, Roudot-Thoraval F, Girou E, Grenier-Sennelier C, Durand-Zaleski I (2003) The costs of septic syndromes in the intensive care unit and influence of hospital-acquired Sepsis. Intensive Care Med 29, 1464-1471

Bustin S A (2002) Quantification of mRNA using real-time reverse transcription PCR (RT-PCR): trends and problems. J Mol Endicronol 29, 23-29

Calandra T, Cohen J. (2005) International Sepsis Forum Definition of Infection in the ICU Consensus Conference. Critical Care Med 33(7), 1538-48.

Carrigan S D Scott G Tabrizian M (2004) Toward resolving the challenges of Sepsis. Clin Chem 50(8), 1301-1314

DE 10 2007 036 678 Verwendung von Polynukleotiden zur Erfassung von Genaktivitäten für die Unterscheidung zwischen lokaler and systemischer Infektion DE 102007036678.9 (nicht veröffentlicht)

Ding B Y and Gentleman R (2004) Classification using generalized partial least squares. Bioconductor Project Working Papers. Paper 5. http://wvvw.begress.com/bioconductor/paper5 9

Efron B (1979) Bootstrap Methods: Another Look at the Jackknife. The Annals of Statistics 7(1), 1-26

FDA: In Vitro Diagnostic Multivariate Index Assays. Draft Guidance for Industry, Clinical Laboratories, and FDA Staff (2003) http://www.fda.gov/cdrh/oivd/guidance/1610.pdf Feezor R J, Baker H V, Xiao W et al. (2004) Genomic and Proteomic Determinants of Outcome in Patients Untergoing Thoracoabdominal Aortic Aneurysm Repair. J Immun 172, 7103-7109

Klein D (2002) Quantification using real-time PCR technology: applications and limitations. Trends Mol Med 8(6), 257-260

Mayhall G (2001) Ventilator-Associated Pneumonia or Not? Contemporary Diagnosis. Emerging Infection Disease CDC 7(2)

Golub T R, Slonim D K, Tamayo P, et al. (1999) Molecular classification of cancer: class discovery and class prediction by gene expression monitoring. Science 286, 531-537

Hastie T, Tibshirani R, Friedman J. (2001) The Elements of Statistical Learning: Data Mining, Inference, and Prediction. Springer Series in Statistics.

Hollander M., Wolfe D., (1973), Nonparametric statistical inference. New York: John Wiley & Sons.

Huber W, von Heydebreck A, Sueltmann H, Poustka A, Vingron M (2003) Parameter estimation for the calibration and variance stabilization of microarray data. Stat Appl in Genetics and Mol Biology 2(1), Article 3

Huggett J, Dheda K, Bustin S et al. (2005) Real-time RT-PCr normalisation; strategies and considerations Genes Immun 6(4), 279-284

Increase in National Hospital Discharge Survey rates for septicemia—United States, 1979-1987. MMWR Morb Mortal Wkly Rep 1990 39, 31-34

Johnson S B, Lissauer M, Bochicchio G V, Moore R, Cross A S, Scales T M. (2007) Gene Expression Profiles Differentiate Between Sterile SIRS and Early Sepsis Annals of Surgery 245(4), 611-621

Knaus W A, Draper E A, Wagner D P, Zimmermann J E (1985) Prognosis in acute organ-system failure. Ann Surg 202, 658-693

Kofoed K, Andersen O, Kronborg G, Tvede M, Petersen J, Eugen-Olsen J, Larsen K (2007), Use of plasma C-reactive protein, procalcitonin, neutrophils, macrophage migration inhibitory factor, soluble urokinase-type plasminogen activator receptor, and soluble triggering receptor expressed on myeloid cells-1 in combination to diagnose infections: a prospective study. Critical Care 11, R38

Kubista M, Andrade J M, Bengtsson M et al. (2006) The real-time polymerase chain reaction. Mol Aspects Med 27, 95-125

Kumar A, Roberts D, Wood K E et al. (2006) Duration of hypotension before initiation of effective antimicrobial therapy is the critical determinant of survival in human septic shock. Crit Care Med 34(6), 1589-1596

Le-Gall J R, Lemeshow S, Leleu G, Klar J, Huillard J, Rue M, Teres D, Artigas A (1995) Customized probability models for early severe Sepsis in adult intensive care patients. Intensive Care Unit Scoring Group. JAMA 273, 644-650

Levy M M, Fink M P, Marshall J C, Abraham E, Angus D, Cook D, Cohen J, Opal S M, Vincent J L, Ramsay G et al. (2003) 2001 SCCM/ESICM/ACCP/ATS/SIS International Sepsis Definitions Conference. Intensive Care Med 29, 530-538

Liu H, Li J, Wong L (2005) Use of extreme patient samples for outcome prediction from gene expression data. Bioinformatics 21(16), 3377-3384

MAQC Consortium. The MicroArray Quality Control (MAQC) project shows inter- and intraplatform reproducibility of gene expression measurements. Nat Biotechnol 2006, 24: 1151-61

Mathiak G, Kabir K, Grass G, et al. (2003) Lipopolysaccharides from different bacterial sources elicit disparate cytokine responses in whole blood assays. Int J Mol Med 11(1), 41-44

Marshall J C, Vincent J L, Fink M P et al, Measures, markers, and mediators: toward a staging system for clinical sepsis. A report of the Fifth Toronto Sepsis Roundtable, Toronto, Ontario, Canada, Oct. 25-26, 2000 and Crit Care Med. 2003, 31: 1560-1567

Mayhall C G (2001) Ventilator-Associated Pneumonia or Not? Contemporary Diagnosis. Emerg Infect Dis 7(2), 200-204

Nolan T, Hands R E, Bustin S A (2006) Quantification of mRNA using real-time RT-PCR. Nat Protoc 1(3), 1559-1582

Opal S M, Lim Y-P, Siryaporn E, et al. (2005) Longitudinal studies of inter-alpha inhibitor proteins in severely septic patients: A potential clinical marker and mediator of severe sepsis. Clin Invest 35(2), 387-292

Pachot A, Lepape A, Vey S, et al. (2006) Systemic transcriptional analysis in survivor and non-survivor septic shock patients: a preliminary study. Immunol Lett 106(1), 63-71. Epub 2006 May 17

Pile J C (2006) Evaluating postoperative fever: a focused approach. Clev Clin J Med. 73 (supp. 1) 62-66

Ramilo O, Allman W, Chung W, Mejias A, Ardura M, Glaser C, Wittkowski K M, Piqueras P, Bancherau J, Palucka K A, Chaussabel D, (2007) Gene expression patterns in blood leukocytes discriminate patients with acute infections. Blood 109, 2066-2077

R Development Core Team (2006) R: A language and environment for statistical computing. R Foundation for Statistical Computing, Vienna, Austria. ISBN 3-900051-07-0, URL http://www.R-project.org Rocke D M, Durbin B. (2001) A model for measurement error for gene expression arrays. J Comput Biol 8, 557-569

Roth A R, Basello D O, (2003) Approach to the adult patient with fever of unknown origin. Am Fam Phys 68(11) 2223-2228

Ruokonen E et al. (1999) Procalcitonin concentrations in patients with neutropenic fever. Eur J Clin Microbiol Infect Dis 18(4), 283-5

Ruokonen E et al. (2002) Procalcitonin and neopterin as indicators of infection in critically ill patients. Acta Anaesthesiol Scand 46(4), 398-404

Simon L, Gauvin F, Amre D K, Saint-Lois P, Lacroix J, (2004) Serum procalcitonin and C-reactive protein levels as marker of bacterial infection: A systematic review and meta analysis. Clin Infec Dis 39, 206-217

Simon R. (2005) Roadmap for Developing and Validating Therapeutically Relevant Genomic Classifiers. J Olin Oncol 23, 7332-7341

Sponholz C, Sakr Y, Reinhart K, Brunkhorst F, (2006) Diagnostic value and prognostic implications of serum procalcitonin after cardiac surgery: a systematic review of the literature, Critical Care 10, 8145

Suprin E et al. (2000) Procalcitonin: a valuable indicator of infection in a medical ICU? Intensive Care Med 26(9), 1232-1238

Tang B M P, Eslick G D, Craig J C et al. (2007a) Accuracy of procalcitonin for sepsis diagnosis in critically ill patients: systematic review and meta-analysis. Lancet Infect Dis 7, 210-217

Tang B M P, McLean A S, Dawes I W, Huang S J, Lin R C Y (2007b) The Use of Gene-Expression Profiling to Identify Candidate Genes In Human Sepsis. American Journal of Respiratory and Critical Care Medicine 176(7), 676-684

US 20060246495 Diagnosis of sepsis

U.S. Pat. No. 6,960,439 Identification, monitoring and treatment of disease and characterization of biological condition using gene expression profiles Vandesompele J, Preter De K, Pattyn F, et al. (2002) Accurate normalisation of real-time quantitative PCR data by geometric averaging of multiple internal control genes. Genome Biology 3(7), research0034.1-0034.11

Valasek M A, Repa J J (2005) The power of real-time PCR. Advan Physiol Educ 29, 151-159

Vapnik V., (1999). The Nature of Statistical Learning Theory. Springer, New York.

Whitcombe D, Theaker J, Guy S P et al. (1999) Detection of PCR products using selfprobing amplicons and fouorescence. Nat Biotechnol 17, 904-907

WO 2006/100203 Verwendung von Genaktivitäts-Klassifikatoren für die in vitro Klassifizierung von Genexpressionsprofilen von Patienten mit infektiösem/nichtinfektiösem Multiorganversagen WO 2004/087949 Verfahren zur Erkennung akuter, generalisierter entzündlicher Zustände (SIRS), Sepsis, sepsisähnlichen Zuständen and systemischen Infektionen WO 2005/083115 Verfahren zur Erkennung von Sepsis WO 2005/106020 Verfahren zur Erstellung von Kriterien zur Vorhersage des Krankheitsverlaufs bei Sepsis WO 2006/042581 Verfahren zur Unterscheidung zwischen nichtinfektiösen and infektiösen Ursachen eines Multiorganversagens WO 2007/144105 Verfahren zur Feststellung der lokalen Entzündung eines Fiebers unklarer Genese WO 2007/124820 Verfahren zur in vitro-Überwachung postoperativer Veränderungen nach Lebertransplantation WO 2003/084388 Early detection of sepsis Wong M L, Medrano J F (2005) Real-time PCR for mRNA quantification. Biotechniques 39(1) 1-11

Zeni F, Freeman B, Natanson C (1997) Anti-inflammatory therapies to treat sepsis and septic shock: A reassessment. Crit Care Med 25(7), 1095-1100

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08765371B2). An electronic copy of the "Sequence Listing" will also be available from the USPTO upon request and payment of the fee set forth in 37 CFR 1.19(b)(3).

The invention claimed is:

1. A kit for carrying out a method for preparing a multigene biomarker, wherein the multigene biomarker is characterized for the in vitro detection, differentiation or progress observation of a pathophysiological condition selected from the group consisting of: systemic inflammatory response syndrome (SIRS), sepsis (and their degrees of severity), sepsis-type conditions, septic shock, infectious/non-infectious multiple organ failure, survival probability in sepsis, focus of an infection, responders/non-responders to a particular therapy and cause of the pathophysiological condition, wherein the cause is associated with gram-positive or gram-negative bacteria, the method including the following steps:

a) isolating sample nucleic acids from a sample originating from a patient;

b) determining gene activities by means of polynucleotide sequences represented by SEQ ID NO: 1 to SEQ ID NO: 669 or their gene loci or transcripts thereof for forming at least one multigene biomarker that is characterized for the detection, differentiation or progress of the pathophysiological condition of the patient;

c) determining gene activities of internal reference genes to which the gene activities determined under b) are related, in particular normalized; and d) forming an index value from the determined normalized gene activities of the multigene biomarker indicating the pathophysiological condition, wherein the interpretation of the index value results in the diagnosis of a pathophysiological condition in a patient, wherein the kit contains the polynucleotide sequences represented by SEQ ID NO: 1 to SEQ ID NO: 669 or their gene loci or transcripts thereof, and further wherein the multigene biomarker is specific for the patient's pathophysiological condition.

2. The kit according to claim 1, characterized in that the polynucleotide sequences also include gene loci, sense/antisense strands of pre-mRNA, mRNA, small RNA, scRNA, snoRNA, micro RNA, siRNA, dsRNA, ncRNA or transposable elements.

3. The kit according to claim 2, characterized in that the gene loci, sense/antisense strands of pre-mRNA, mRNA, small RNA, scRNA, snoRNA, micro RNA, siRNA, dsRNA, ncRNA or transposable elements are used as the polynucleotide sequences for detecting the gene expression profiles.

* * * * *

UNITED STATES PATENT AND TRADEMARK OFFICE
CERTIFICATE OF CORRECTION

| | | |
|---|---|---|
| PATENT NO. | : 8,765,371 B2 | Page 1 of 2 |
| APPLICATION NO. | : 12/933169 | |
| DATED | : July 1, 2014 | |
| INVENTOR(S) | : Russwurm | |

It is certified that error appears in the above-identified patent and that said Letters Patent is hereby corrected as shown below:

In the Specification

Col. 1, line 51: The word "begin" should read "beginning";

Col. 3, line 5: The word "syndrom" should read "syndrome";

Col. 4, line 27: Insert a space between the words "amino" and "acids";

Col. 6, line 47: Delete the second occurrence of the word "a";

Col. 7, line 23: The word "Texan" should read "Texas";

Col. 7, line 51: Delete Lines 51-55;

Col. 8, line 49: The word "next" should read "nearest";

Col. 8, line 50: Delete the phrase "k-next neighbor";

Col. 9, line 67: Delete the phrase "of a";

Col. 10, line 24: Insert the word --physicians-- after the word "allows";

Col. 11, line 16: The word "syndrom" should read "syndrome";

Col. 12, line 7: The word "desoxyribonucleic" should read "deoxyribonucleic";

Col. 12, line 32: The word "des" should read "designating";

Col. 20, line 6: The word "provides" should read "provide";

Col. 20, line 26: Insert a --.-- after the first occurrence of the word "selection";

Col. 21, line 3: The word "application" should read "publication";

Signed and Sealed this
Sixth Day of January, 2015

Michelle K. Lee
*Deputy Director of the United States Patent and Trademark Office*

CERTIFICATE OF CORRECTION (continued)
U.S. Pat. No. 8,765,371 B2

Col. 25, line 53: The word "als" should read "as";

Col. 25, line 62: Delete the word "a";

Col. 25, line 63: The word "(a)" should read "(b)";

Col. 25, line 64: The word "(b)" should read "(a)";

Col. 26, line 7: Delete the word "a";

Col. 26, line 8: Insert a --)-- after the word "diagnosis";

Col. 26, line 9: Delete the word "a";

Col. 26, line 19: The number "11" should read "12";

Col. 26, line 22: The number "12" should read "11";

Col. 42, line 36: Capitalize "University Hospital";

Col. 46, line 34: The word "and" should read "or";

Col. 46, line 36: The word "and" should read "or";

Col. 57, line 66: The word "Illumine" should read "Illumina";

Col. 58, line 21: Each occurrence of the word "Illumine" should read "Illumina";

Col. 59, line 2: The word "ix" should read "mix";

Col. 67, line 10: The "," should be replaced with a ".";

Col. 73, line 24: Capitalize "University Hospital";

Col. 74, line 13: Insert a second --)-- after "207)".